US010485459B2

(12) United States Patent
Arita et al.

(10) Patent No.: US 10,485,459 B2
(45) Date of Patent: Nov. 26, 2019

(54) SENSOR INSERTION DEVICE AND REPLACEMENT PART

(71) Applicant: TERUMO KABUSHIKI KAISHA, Tokyo (JP)

(72) Inventors: Eiji Arita, Hadano (JP); Takeshi Tsubouchi, Yokosuka (JP); Hideyuki Momoki, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 226 days.

(21) Appl. No.: 15/697,036

(22) Filed: Sep. 6, 2017

(65) Prior Publication Data

US 2017/0367630 A1 Dec. 28, 2017

Related U.S. Application Data

(63) Continuation of application No. PCT/JP2016/000024, filed on Jan. 5, 2016.

(30) Foreign Application Priority Data

Mar. 11, 2015 (JP) ................ 2015-048437

(51) Int. Cl.
- *A61B 5/00* (2006.01)
- *A61B 5/145* (2006.01)
- *A61B 5/157* (2006.01)

(52) U.S. Cl.
CPC ........ *A61B 5/14503* (2013.01); *A61B 5/0031* (2013.01); *A61B 5/14532* (2013.01);
(Continued)

(58) Field of Classification Search
CPC .......... A61M 5/158; A61M 2005/1585; A61M 2005/14252; A61B 5/6849; A61B 5/14865

See application file for complete search history.

(56) References Cited

U.S. PATENT DOCUMENTS 6,584,335 B1    6/2003  Haar et al.
7,381,184 B2 *  6/2008  Funderburk ....... A61B 5/14532
                                                600/300

(Continued)

FOREIGN PATENT DOCUMENTS

EP    3 251 596 A1    12/2017
JP    2013-523217      6/2013

(Continued)

OTHER PUBLICATIONS

International Search Report issued in International Patent Application No. PCT/JP2016/000024 dated Mar. 29, 2016.

(Continued)

*Primary Examiner* — Eric J Messersmith

(74) *Attorney, Agent, or Firm* — Foley & Lardner LLP

(57) ABSTRACT

A sensor insertion device includes a first elastic member; a second elastic member; an elastic energy variable mechanism configured to elastically deform the first elastic member and the second elastic member to achieve an energy accumulated state; a first holding mechanism configured to hold a position of the first elastic member in the energy accumulated state; and a second holding mechanism configured to hold a position of the second elastic member in the energy accumulated state for a period of time during which, after the release of the first elastic member from the first holding mechanism in the energy accumulated state, the needle member is moved to the insertion position by the first elastic energy.

15 Claims, 23 Drawing Sheets

(52) U.S. Cl.
CPC .............. *A61B 5/157* (2013.01); *A61B 5/688* (2013.01); *A61B 5/72* (2013.01)

(56) References Cited

U.S. PATENT DOCUMENTS

| | | | | |
|---|---|---|---|---|
| 8,409,145 | B2* | 4/2013 | Raymond | A61M 5/14244 604/157 |
| 2008/0319414 | A1* | 12/2008 | Yodfat | A61B 5/6849 604/506 |
| 2010/0217105 | A1* | 8/2010 | Yodfat | A61B 5/14503 600/365 |
| 2011/0288574 | A1* | 11/2011 | Curry | A61B 5/15194 606/185 |
| 2012/0150123 | A1* | 6/2012 | Lawrence | A61M 5/158 604/180 |
| 2012/0190942 | A1 | 7/2012 | Donnay et al. | |
| 2013/0110047 | A1* | 5/2013 | Gyrn | A61M 25/0612 604/164.08 |
| 2016/0058344 | A1* | 3/2016 | Peterson | A61B 5/14532 600/347 |
| 2016/0243302 | A1* | 8/2016 | Gyrn | A61M 5/158 |

FOREIGN PATENT DOCUMENTS

| | | |
|---|---|---|
| WO | WO-2002/056769 | 7/2002 |
| WO | WO-2004/110275 | 12/2004 |
| WO | WO-2013/035455 | 3/2013 |

OTHER PUBLICATIONS

Extended European Search Report dated Sep. 14, 2019 in corresponding application No. 16761213.4.

* cited by examiner

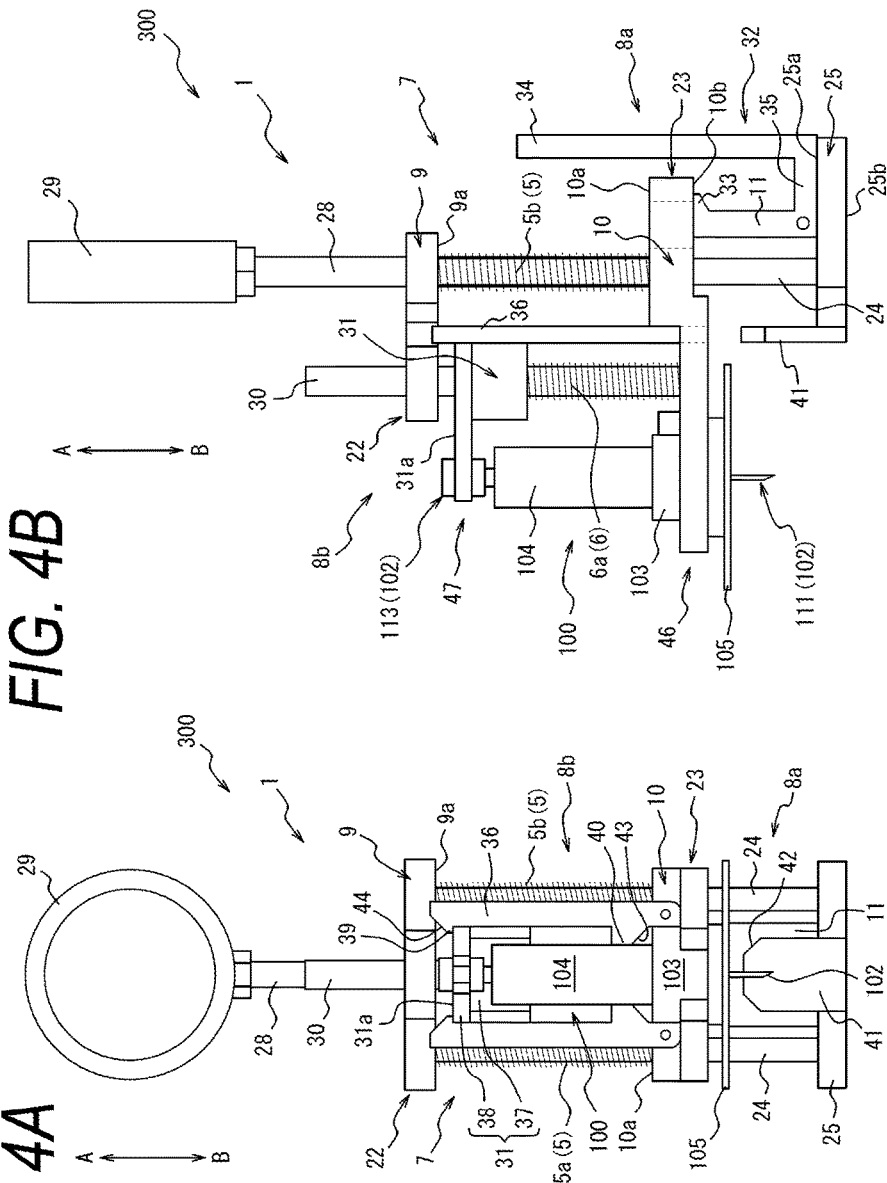

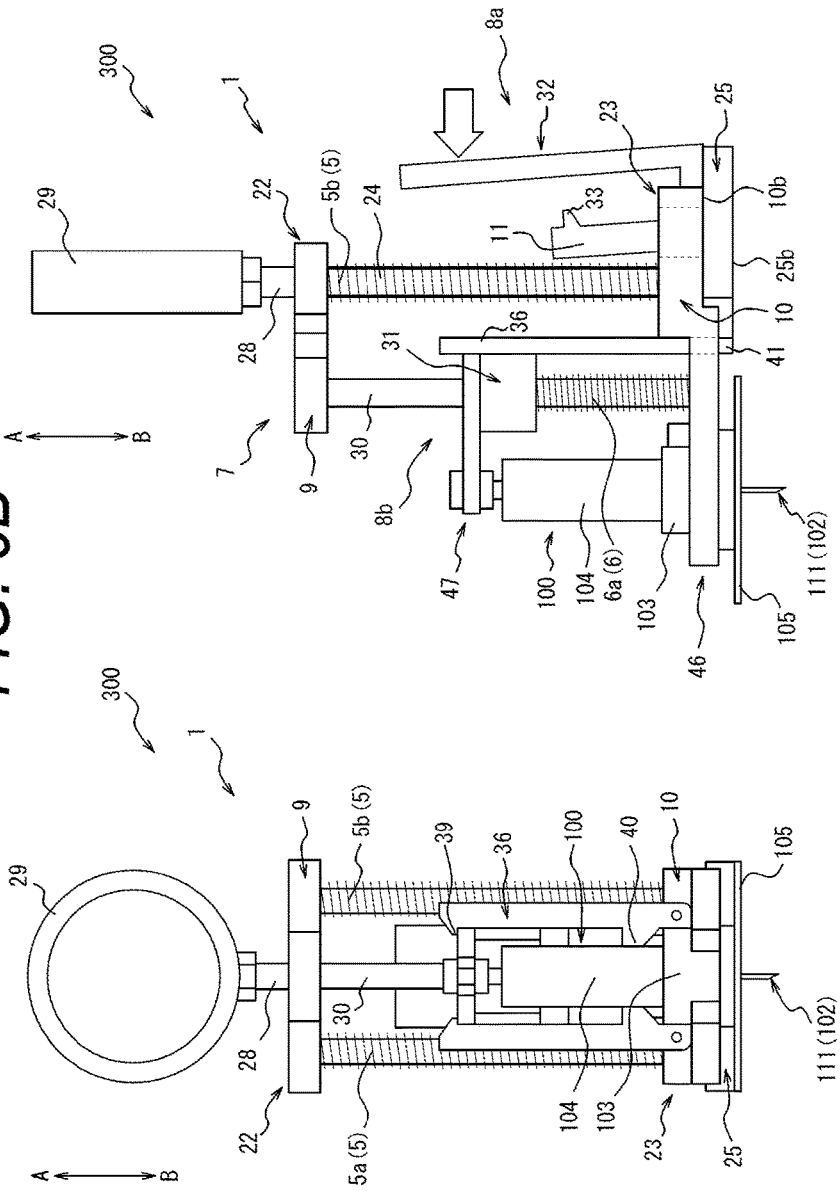

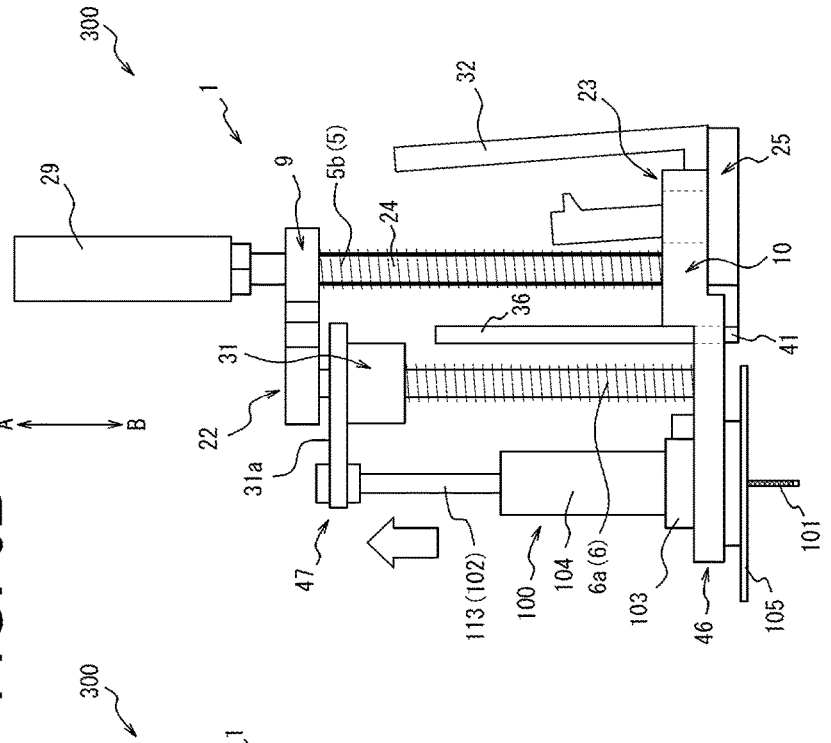
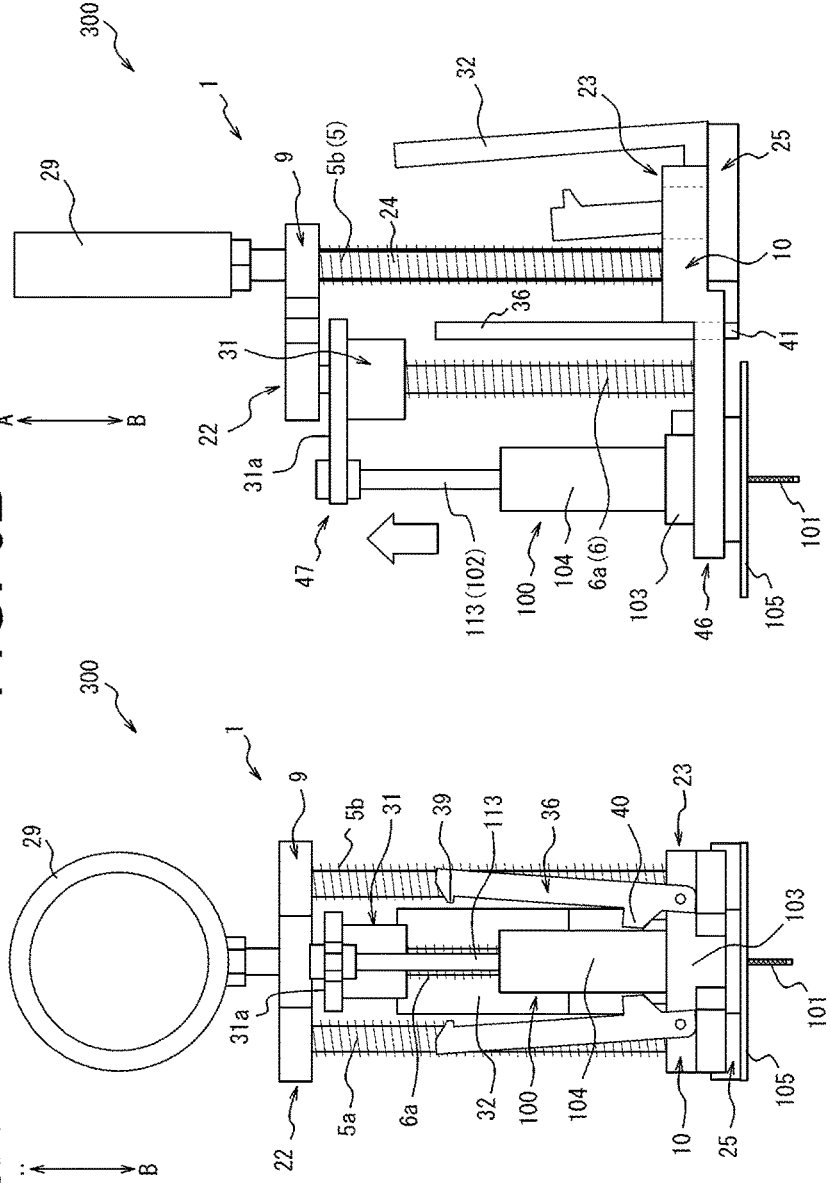

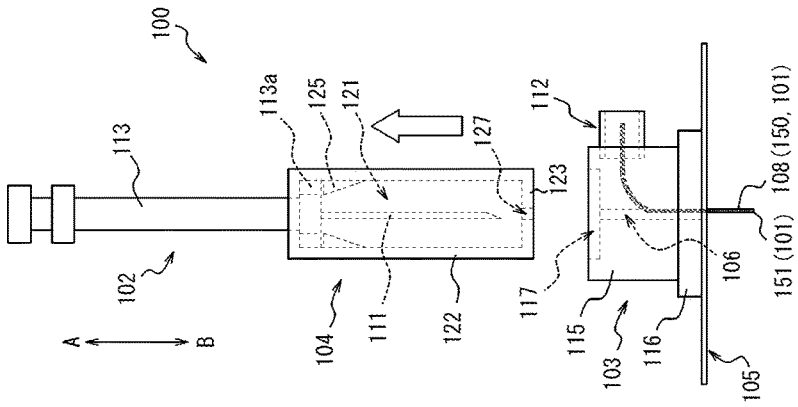
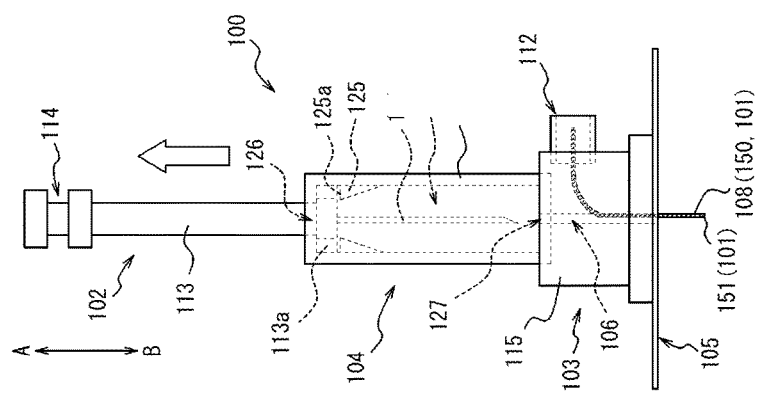
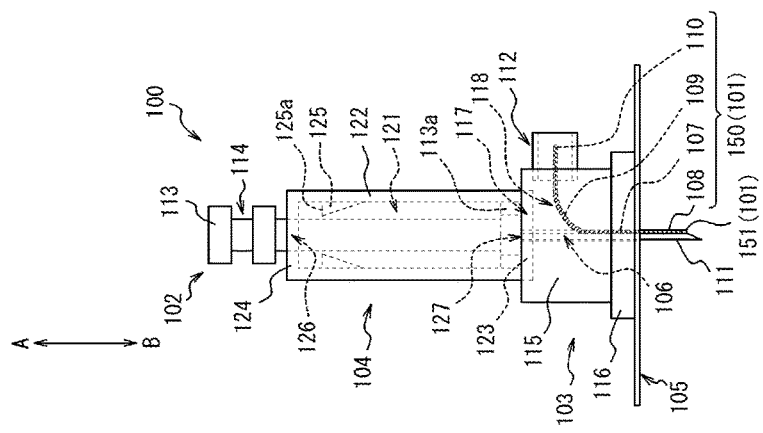

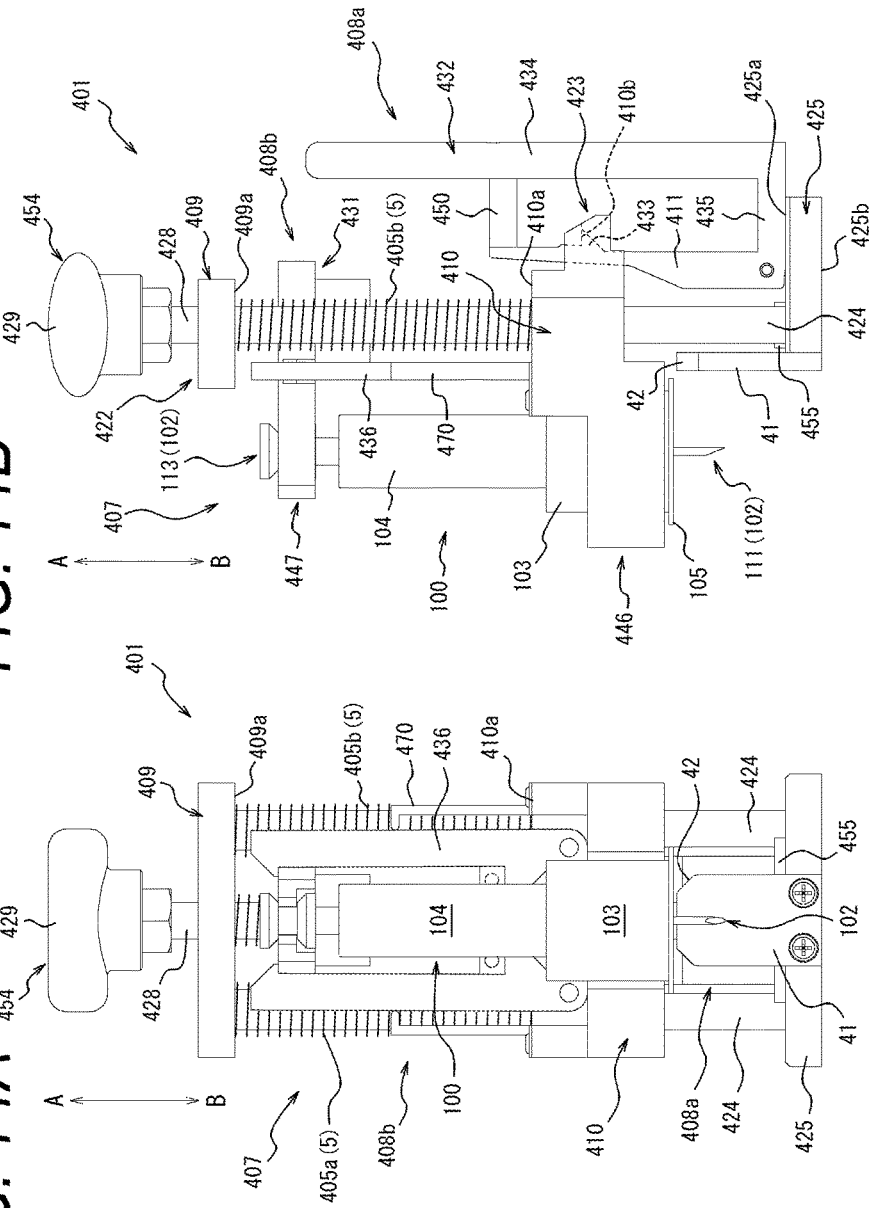

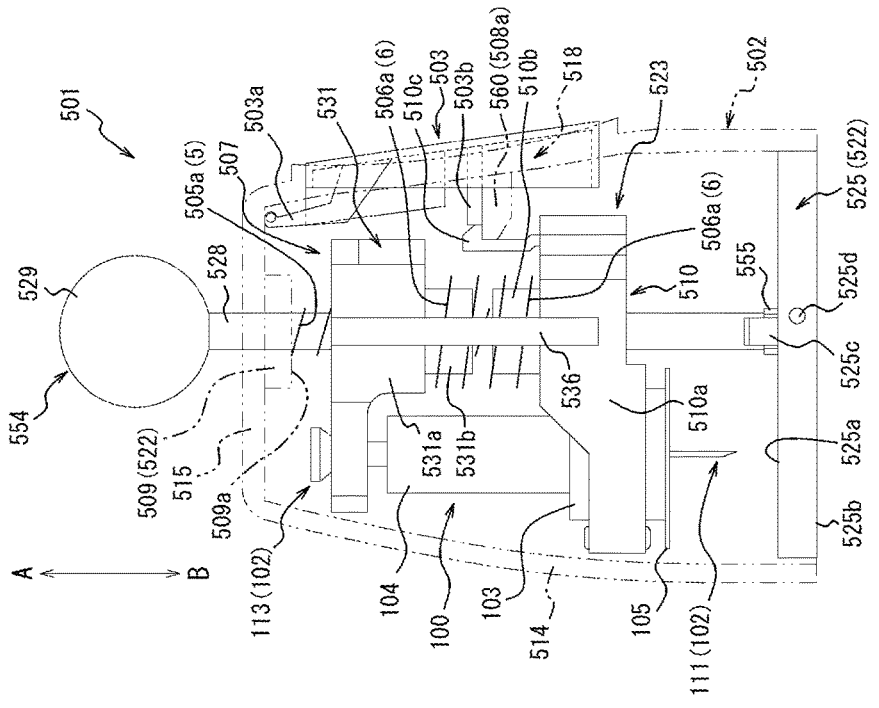
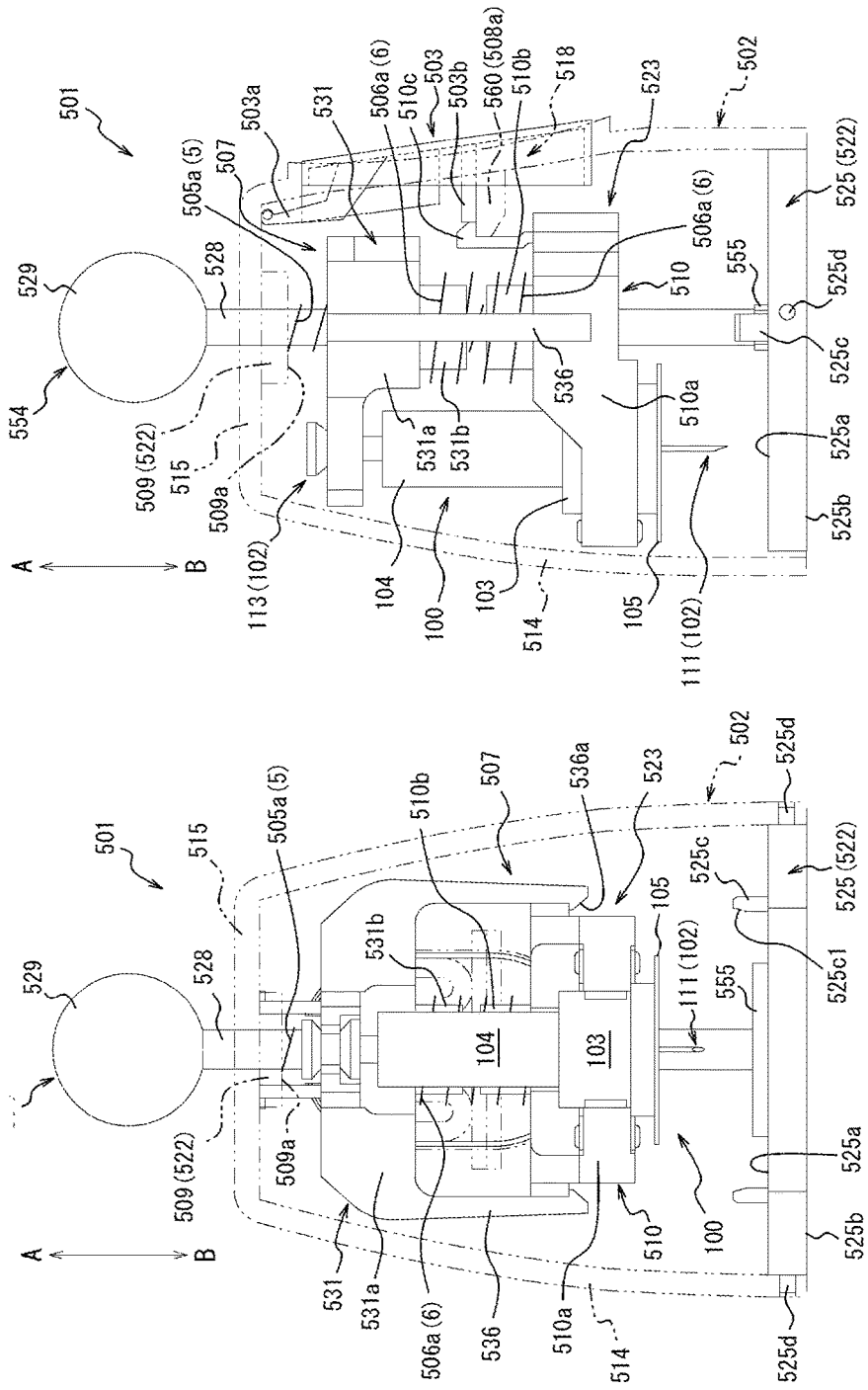
FIG. 20A
FIG. 20B

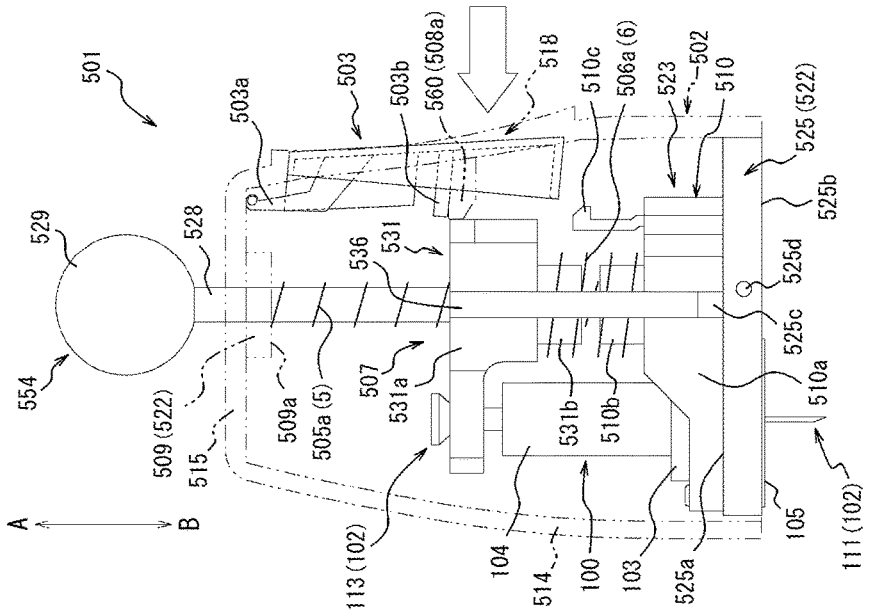
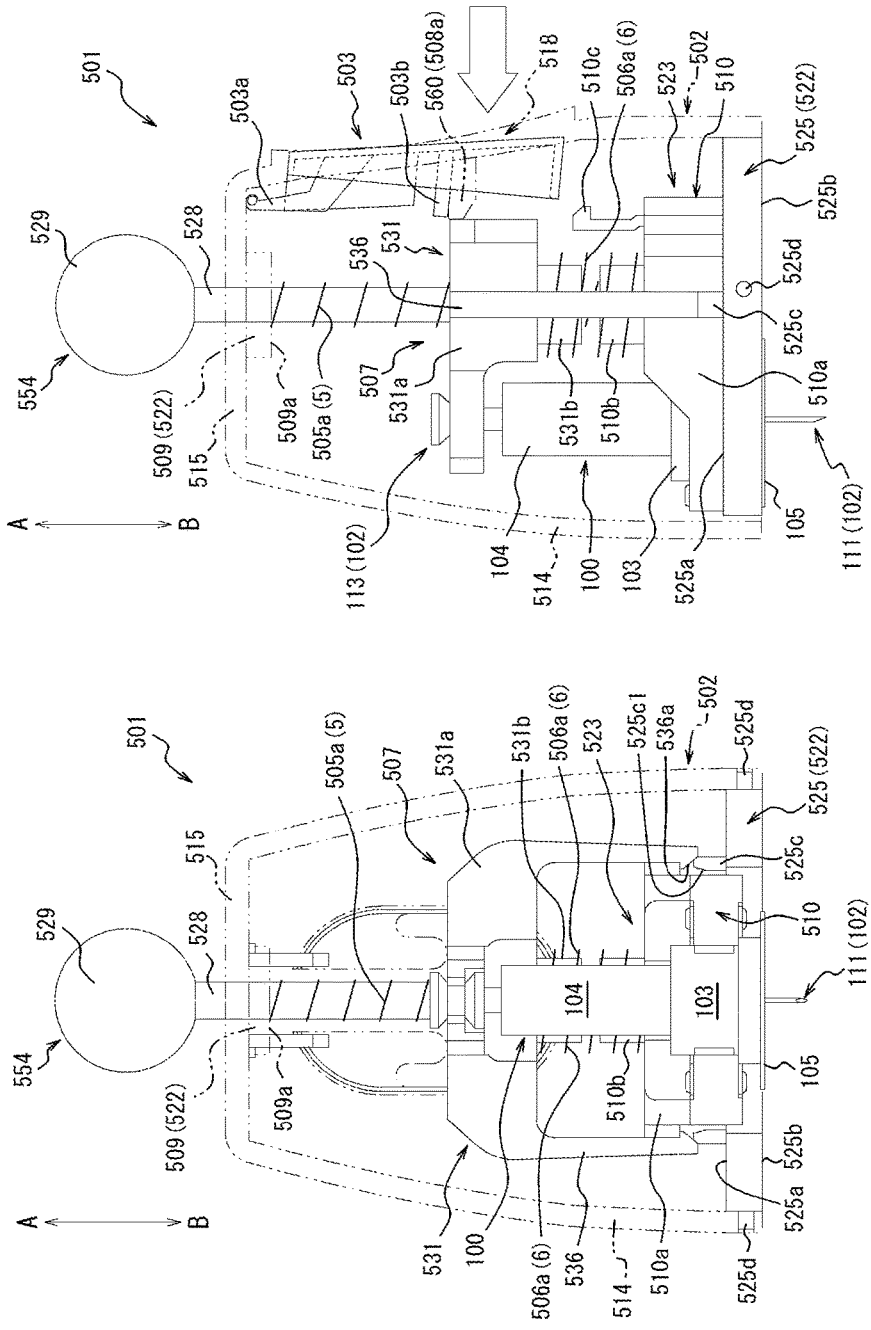
FIG. 21A
FIG. 21B

SENSOR INSERTION DEVICE AND REPLACEMENT PART

CROSS-REFERENCE TO RELATED APPLICATIONS

The present application is a bypass continuation of PCT Application No. PCT/JP2016/000024, filed on Jan. 5, 2016, which claims priority to Japanese Application No. 2015-048437, filed on Mar. 11, 2015. The contents of these applications are hereby incorporated by reference in their entireties.

BACKGROUND

The present disclosure relates to a sensor insertion device for inserting a sensor detecting biological information of a living body, such as a patient, into the living body, and a replacement part that is attachable to the sensor insertion device.

It is known to insert or embed a sensor in a body of a person to be measured, such as a patient, and detect analytes (for example, glucose, pH, cholesterol, protein, etc.) in blood or body fluid of the patient by using the sensor. In this case, a sensor insertion device is used for quickly and easily disposing the sensor through the skin of the patient (refer to JP 2013-523217 A).

JP 2013-523217 A describes a sharp member (needle member) that is inserted into a living body together with the sensor and a plunger that moves the sensor and the sharp member to perform puncture. According to the configuration described in JP 2013-523217 A, an assembly portion can be left in the living body along with the sensor inserted into the living body. The assembly portion includes a wearable electronic device that stores acquired biological information such as blood sugar level.

SUMMARY

In the above-described kind of sensor insertion device, it is preferably that the time taken for insertion and removal of the needle member is short, to reduce the pain of a person to be measured, such as a patient, during the insertion and removal of the needle member.

In the sensor insertion device described in JP 2013-523217, the plunger is biased by a drive spring in the insertion direction of the needle member to insert the needle member into a living body, and the plunger is biased by a return spring in the removal direction of the needle member to remove the needle member from the living body.

According to this configuration, the biasing force of the return spring acts to reduce the biasing force of the drive spring at the insertion of the needle member, and the biasing force of the drive spring acts to reduce the biasing force of the return spring at the removal of the needle member. Therefore, the sensor insertion device needs to be designed with consideration given to the balance between the drive spring and the return spring. This makes it difficult to achieve a sensor insertion device that enables further shortening of the time taken for insertion and removal of the needle member.

In addition, it is preferably that a portion of the member to be inserted into a living body is a disposable replacement part and the other portions are reusable.

To address this, embodiments described herein aim to provide a sensor insertion device that makes it possible to shorten the time taken for insertion and removal of a needle member, and to reuse the needle member, and a replacement part attachable to the sensor insertion device.

According to one embodiment, a sensor insertion device is configured for insertion of a needle member together with a sensor capable of detecting biological information into a living body, and for removal the needle member from the living body after leaving a distal end side of the sensor in the living body. The sensor insertion device includes a first elastic member that can accumulate first elastic energy to move the sensor and the needle member to an insertion position where the sensor and the needle member are insertable into the living body; a second elastic member that can accumulate second elastic energy to move the needle member from the insertion position to a removal position where the needle member is removable from the living body; an elastic energy variable mechanism that can elastically deform the first elastic member and the second elastic member to achieve an energy accumulated state in which the first elastic energy is accumulated in the first elastic member and the second elastic energy is accumulated in the second elastic member; a first holding mechanism that holds the posture of the first elastic member in the energy accumulated state; and a second holding mechanism that holds the posture of the second elastic member in the energy accumulated state and for a period of time during which, after the release of the first elastic member from the first holding mechanism in the energy accumulated state, the needle member is moved to the insertion position by the first elastic energy.

According to an embodiment, the elastic energy variable mechanism includes a fixed member and a movable member that is movable with respect to the fixed member, which sandwich the first elastic member and the second elastic member therebetween.

According to an embodiment, the fixed member includes a movement restriction portion that is positioned on a removal direction side of the needle member with respect to the first elastic member and the second elastic member, the movable member includes a main body portion that is positioned on an insertion direction side of the needle member with respect to the first elastic member and the second elastic member, and the main body portion is moved in the removal direction to elastically deform the first elastic member and the second elastic member at the same time between the main body portion and the movement restriction portion, thereby to achieve the energy accumulated state.

According to an embodiment, the first holding mechanism includes a retaining portion that retains the movable member in the energy accumulated state.

According to an embodiment, a plurality of first elastic members is provided, and the second elastic member is disposed between the plurality of first elastic members.

According to an embodiment, it is preferable that the second elastic member defines a hollow portion, the movable member includes a bar-like portion that is connected to an operation portion capable of being operated from the outside, and the bar-like portion extends in the hollow portion of the second elastic member.

According to an embodiment, one of the first elastic member and the second elastic member defines a hollow portion, and the other of the first elastic member and the second elastic member extends in the hollow portion of the one elastic member.

According to an embodiment, the other elastic member defines a hollow portion, the movable member includes a bar-like portion that is connected to an operation portion capable of being operated from the outside, and the bar-like portion extends in the hollow portion of the other elastic member.

According to an embodiment, when the movable member is set as a first movable member, the second holding mechanism includes: a second movable member that is sandwiched between the fixed member and the second elastic member and is movable with respect to the fixed member and the first movable member; and a lock portion that engages with the second movable member biased by the second elastic member toward the fixed member while the second elastic energy is accumulated in the second elastic member to fix the position of the second movable member with respect to the first movable member.

According to an embodiment, the sensor insertion device includes a disengagement portion that disengages the lock portion from the second movable member when the needle member reaches the insertion position.

According to an embodiment, the sensor insertion device includes an attachment portion to which a replacement part with the sensor and the needle member is attachable from the outside in the energy accumulated state.

According to a second aspect, a replacement part includes the sensor and the needle member and attachable to the above described sensor insertion device.

According to an embodiment, the replacement part further includes a sensor housing that defines an insertion hole in which the needle member can be moved by the sensor insertion device from the insertion position to the removal position, wherein the sensor includes a portion that extends outward from a clearance (i.e, slit) formed in the needle member in the sensor housing.

According to an embodiment, the sensor includes: a light guiding member that has a distal end left in a living body and a proximal end extending outside of the living body; and a detection portion that is provided at the distal end portion of the light guiding member and can detect biological information, and the light guiding member includes a curve portion that extends outward from the clearance (i.e. slit) in the needle member.

According to an embodiment, the replacement part further includes a hollow member that accommodates the needle member when the needle member moves to the removal position, wherein the hollow member includes a one-way lock portion that, after the movement of the needle member from the insertion position to the removal position, restricts the movement of the needle member back to the insertion position.

Certain embodiments described herein make it possible to shorten the time taken for insertion and removal of a needle member, and to reuse the needle member, and provide a replacement part attachable to the sensor insertion device.

BRIEF DESCRIPTION OF THE DRAWINGS

FIGS. 4A and 4B are front and side views illustrating the state in which the replacement part is attached to the sensor insertion device in an energy accumulated state.

FIGS. 5A and 5B are front and side views illustrating the state in which a needle member in the replacement part illustrated in FIGS. 4A and 4B reaches an insertion position by the action of the sensor insertion device illustrated in FIGS. 4A and 4B.

FIGS. 6A and 6B are front and side views illustrating the state in which the needle member in the replacement part illustrated in FIGS. 4A and 4B reaches a removal position by the action of the sensor insertion device illustrated in FIGS. 4A and 4B.

FIGS. 8A through 8C illustrate form changes of the replacement part illustrated in FIGS. 4A and 4B.

FIGS. 14A and 14B are front and side views illustrating the state in which the replacement part is attached to the sensor insertion device in the energy accumulated state.

FIGS. 20A and 20B are front and side views illustrating the state in which the replacement part is attached to the sensor insertion device in the energy accumulated state.

FIGS. 21A and 21B are front and side views illustrating the state in which a needle member in the replacement part illustrated in FIGS. 20A and 20B reaches an insertion position by the action of the sensor insertion device illustrated in FIGS. 20A and 20B.

DETAILED DESCRIPTION

Figure 1:
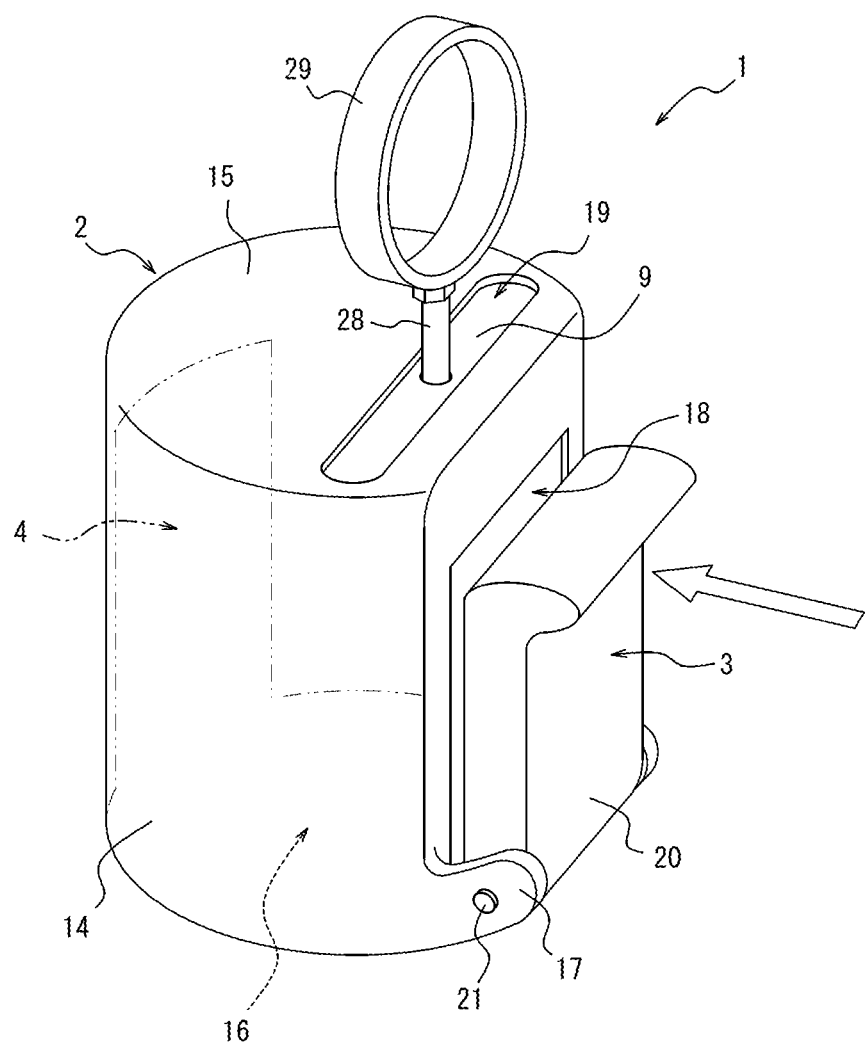
FIG. 1 is a perspective view of a sensor insertion device according to one embodiment of the present invention.

Embodiments of a sensor insertion device and a replacement part attachable to the sensor insertion device will be described below with reference to the figures. The same members illustrated in the drawings are given the same reference signs.

Figure 2:
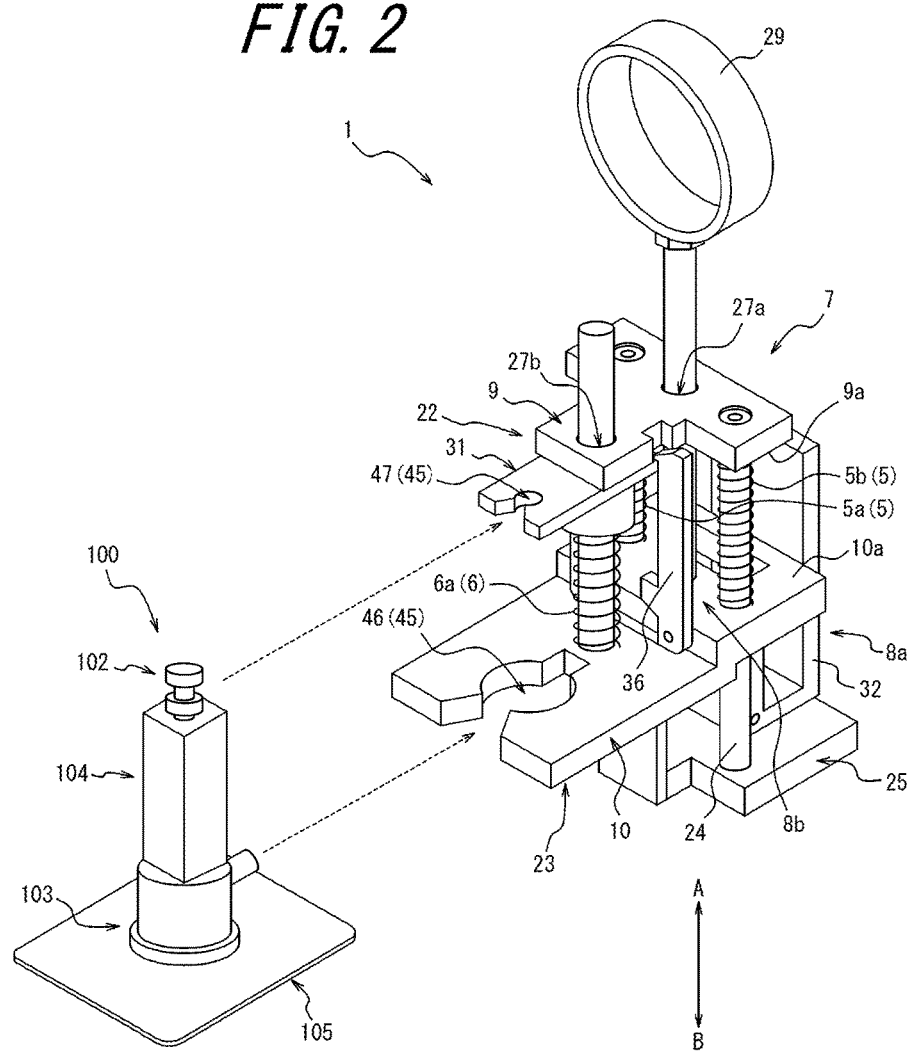
FIG. 2 is a perspective view of the sensor insertion device illustrated in FIG. 1 and a replacement part according to the embodiment of the present invention, which are shown separately.
Figure 3:
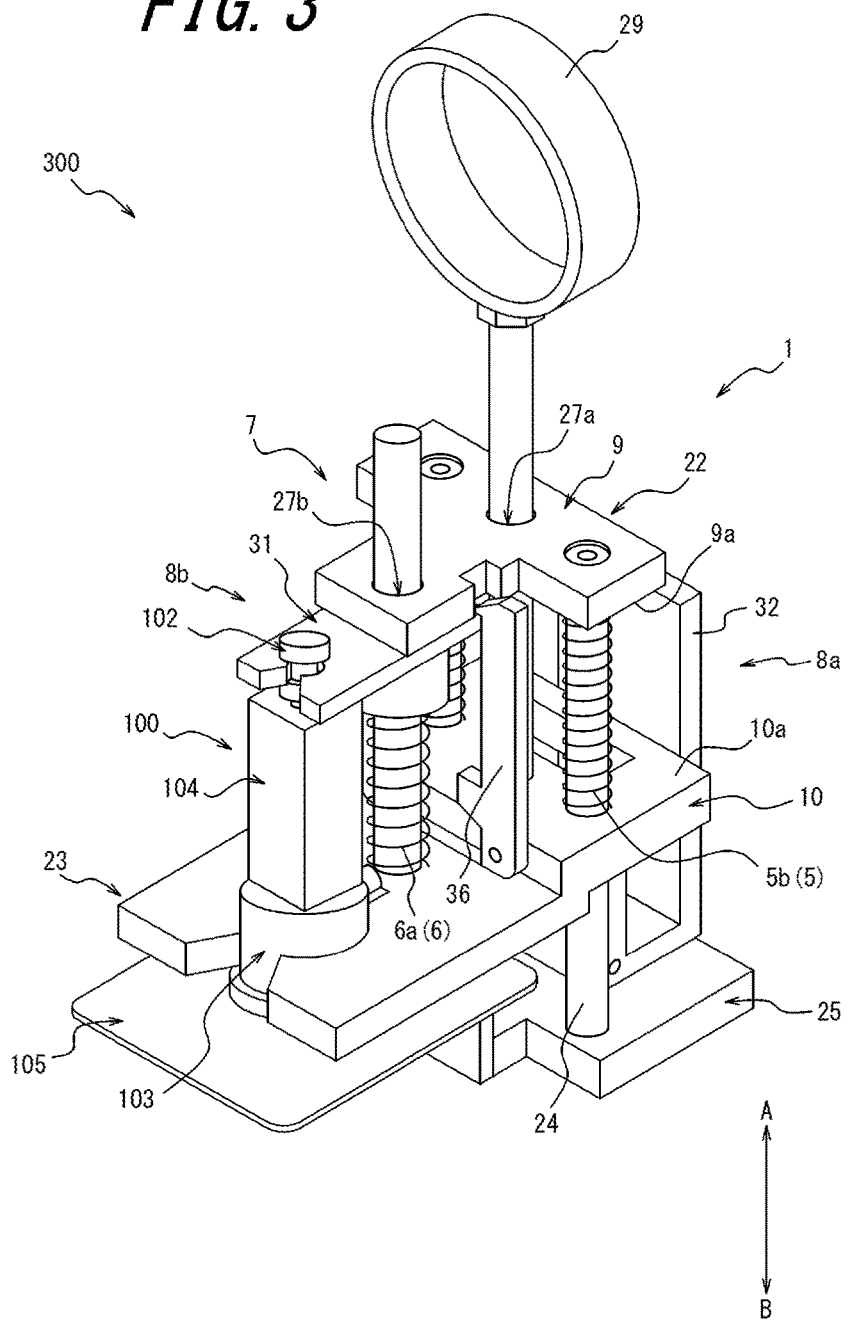
FIG. 3 is a perspective view of a sensor insertion device assembly in which the replacement part illustrated in FIG. 2 is attached to the sensor insertion device illustrated in FIG. 2.

FIG. 1 is a perspective view of a sensor insertion device 1 according to one embodiment of the present invention. FIG. 2 is a perspective view of the sensor insertion device 1 illustrated in FIG. 1 and a replacement part 100 attachable to the sensor insertion device 1 according to the embodiment of the present invention, which are separately illustrated. FIG. 3 is a perspective view of a sensor insertion device assembly 300 in which the replacement part 100 illustrated in FIG. 2 is moved (see the dashed arrows in FIG. 2) and attached to the sensor insertion device 1. For the convenience of description, FIGS. 2 and 3 do not illustrate a housing 2 in the sensor insertion device 1 and an operation member 3 rotatably attached to the housing 2 illustrated in FIG. 1. Therefore, to attach the replacement part 100 to the sensor insertion device 1 (to change from the state illustrated in FIG. 2 to the state illustrated in FIG. 3), the replacement part 100 is attached to the sensor insertion device 1 through a side wall opening 4 in the housing 2 shown by a two-dot chain line (virtual line) illustrated in FIG. 1.

The sensor insertion device assembly 300 illustrated in FIG. 3 includes the sensor insertion device 1 and the replacement part 100 attached to the sensor insertion device 1.

The sensor insertion device 1 is designed to move and insert a sensor 101 and a needle member 102 in the attached replacement part 100 (see FIGS. 8A through 8C and others) into a living body by operating the operation member 3. The sensor insertion device 1 is also designed to, after leaving the distal end of the sensor 101 in the living body, remove the needle member 102 from the living body. Further, after the removal of the needle member 102 from the living body, the sensor insertion device 1 is detached from the replacement part 100 and is reused to insert a sensor 101 and a needle member 102 in another replacement part 100 into a living body and remove the needle member 102 after leaving the sensor 101. Reusing the sensor insertion device 1 makes it possible to lighten the burden of costs borne by a person to be measured such as a patient and medical personnel.

The sensor insertion device 1 illustrated in FIGS. 1 to 3 includes the housing 2, the operation member 3, a first elastic member 5, a second elastic member 6, an elastic energy variable mechanism 7, and a holding mechanism. The holding mechanism includes a first holding mechanism 8a and a second holding mechanism 8b.

The replacement part 100 has a member to be left in a living body together with the sensor 101 and a discarded member after the detachment from the sensor insertion device 1.

The replacement part 100 illustrated in FIGS. 1 to 3 includes the sensor 101 (see FIGS. 8A through 8C and others), the needle member 102 (see FIGS. 8A through 8C and others), a sensor housing 103, a hollow member 104, and a sheet member 105. In the replacement part 100 of the embodiment, the sensor 101, the sensor housing 103, and the sheet member 105 are members that are to be left in a living body to detect and measure analytes (for example, glucose, pH, cholesterol, protein, etc.) as biological information after the detachment of the replacement part 100 from the sensor insertion device 1, and the needle member 102 and the hollow member 104 are members that are to be discarded after the detachment of the replacement part 100 from the sensor insertion device 1.

<Sensor Insertion Device 1>

The sensor insertion device 1 and the replacement part 100 will be described below in detail. First, the sensor insertion device 1 will be described below in detail.

The housing 2 is an exterior member of the sensor insertion device 1 as illustrated in FIG. 1 and covers the circumference of the internal components illustrated in FIGS. 2 and 3. As illustrated in FIG. 1, the housing 2 has the side wall opening 4 (see the two-dot chain lines in FIG. 1) through which the replacement part 100 can be attached to and detached from the internal structure of the sensor insertion device 1 (the components except for the housing 2 and the operation member 3 of the sensor insertion device 1, which are illustrated in FIGS. 2 and 3) positioned in the hollow portion of the housing 2. One end of the hollow portion of the housing 2 (the lower end in FIG. 1) is opened and the sensor 101 and the needle member 102 puncture a living body through the opened portion. Therefore, when the sensor 101 and the needle member 102 are inserted from the sensor insertion device 1 into the living body, the sensor 101 and the needle member 102 are inserted into the living body by operating the operation member 3 in the state in which the end surface of the one end of the housing 2 (the lower end in FIG. 1) is pressed against the surface of the living body.

The material for the housing 2 may be a resin material, for example. Examples of the resin material include thermoplastic resins used for injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate, and thermosetting resins such as phenol resin, epoxy resin, silicone resin, and unsaturated polyester.

The operation member 3 is rotatably attached to the housing 2. The person to be measured such as a patient and the medical personnel can insert the attached sensor 101 and the needle member 102 into the living body by rotating and operating the operation member 3 with the end surface of one end of the housing 2 pressed against the surface of the living body.

The operation member 3 can be formed from the same material as that for the housing 2 described above. Alternatively, the operation member 3 may be formed from a ceramic material, a metallic material, or the like.

The first elastic member 5 can accumulate first elastic energy for moving the needle member 102 in the replacement part 100 to an insertion position where the needle member 102 is insertable into a living body. In the embodiment, two insertion springs 5a and 5b are used as the first elastic member 5. The insertion springs 5a and 5b are formed from coil springs. The "insertion position" means the position where at least the distal end of the needle member is insertable into a living body.

The second elastic member 6 can accumulate second elastic energy for moving the needle member 102 in the replacement part 100 from the insertion position to a removal position where the needle member 102 is removable from a living body. In the embodiment, one return spring 6a is used as the second elastic member 6. The return spring 6a is formed from a coil spring. The "removal position" means the position where the needle member is removable from a living body.

The elastic energy variable mechanism 7 can elastically deform the first elastic member 5 and the second elastic member 6 to achieve the energy accumulated state in which the first elastic energy is accumulated in the first elastic member 5 and the second elastic energy is accumulated in the second elastic member 6. FIGS. 1 to 3 illustrate the sensor insertion device 1 in the energy accumulated state. In addition, the elastic energy variable mechanism 7 of the embodiment achieves the energy accumulated state by elastically deforming the first elastic member 5 and the second elastic member 6 at the same time. The "achieving the energy accumulated state by elastically deforming the first elastic member 5 and the second elastic member 6 at the same time" means having a process of elastically deforming the first elastic member 5 and the second elastic member 6 at the same time before achieving the energy accumulated state, which may include a process of elastically deforming either one of them.

The elastic energy variable mechanism 7 includes a fixed member 22 and a movable member 23 movable with respect to the fixed member 22, which sandwich the first elastic member 5 and the second elastic member 6 therebetween.

The fixed member 22 in the elastic energy variable mechanism 7 of the embodiment includes a movement restriction portion 9 that is positioned on a removal direction A side of the needle member 102 with respect to the first elastic member 5 and the second elastic member 6. The movable member 23 in the elastic energy variable mechanism 7 of the embodiment includes a main body portion 10 that is positioned on an insertion direction B side of the needle member 102 with respect to the first elastic member 5 and the second elastic member 6. Therefore, the elastic energy variable mechanism 7 of the embodiment can achieve the energy accumulated state by moving the main body portion 10 in the removal direction A and subjecting the first elastic member 5 and the second elastic member 6 to compressive deformation at the same time between the main body portion 10 and the movement restriction portion 9.

Examples of the material for the fixed member 22 and the movable member 23 constituting the elastic energy variable mechanism 7 include metallic materials such as stainless steel, aluminum, aluminum alloy, titanium, and titanium alloy, and the resin materials usable for the housing 2 described above.

The first holding mechanism 8a holds the posture of the first elastic member 5 in the energy accumulated state. The first holding mechanism 8a of the embodiment includes a retaining member 32 as a retaining portion that retains the movable member 23 in the energy accumulated state.

Examples of the material for the retaining member 32 of the first holding mechanism 8a include the resin materials usable for the housing 2 described above.

The second holding mechanism 8b holds the posture of the second elastic member 6 in the energy accumulated state and for the period of time between the release of the first elastic member 5 from the first holding mechanism 8a in the energy accumulated state and the movement of the needle member 102 to the insertion position by the first elastic energy.

The second holding mechanism 8b includes a movable member 31 and lock members 36 as lock portions. To differentiate between the movable member 23 in the elastic energy variable mechanism 7 and the movable member 31 in the second holding mechanism 8b, for the sake of the convenience, the movable member 23 in the elastic energy variable mechanism 7 will be referred to as "first movable member 23" and the movable member 31 in the second holding mechanism 8b will be referred to as "second movable member 31."

The second movable member 31 of the embodiment is sandwiched between the fixed member 22 and the second elastic member 6 and is movable with respect to the fixed member 22 and the first movable member 23. Specifically, the second movable member 31 of the embodiment is positioned between the movement restriction portion 9 in the fixed member 22 and the second elastic member 6 and can change the opposing distance to the movement restriction portion 9 in the fixed member 22 and the main body portion 10 in the first movable member 23. More specifically, the second movable member 31 is movable with respect to the movement restriction portion 9 in the removal direction A and the insertion direction B, and is also movable with respect to the main body portion 10 in the removal direction A and the insertion direction B.

The lock members 36 of the embodiment can engage with the second movable member 31 biased by the second elastic member 6 to the movement restriction portion 9 side of the fixed member 22, that is, in the removal direction A, in the energy accumulated state, to fix the position of the second movable member 31 with respect to the first movable member 23. Therefore, when the lock members 36 engage with the second movable member 31, the positional relationship between the first movable member 23 and the second movable member 31 is fixed. Accordingly, at the time of insertion of the sensor 101 and the needle member 102, even though the main body portion 10 moves in the insertion direction B to be distant from the movement restriction portion 9 by the resilience of the first elastic member 5, the positional relationship between the first movable member 23 and the second movable member 31 is maintained by the lock members 36 in the energy accumulated state. This will be described later in detail.

Examples of material for the second movable member 31 and the lock members 36 of the second holding mechanism 8b include the resin materials usable for the housing 2 and the metallic materials usable for the fixed member 22 and the movable member 23 described above.

The members, mechanisms, and other characteristic portions of the sensor insertion device 1 will be described below in detail.

[Housing 2]

The housing 2 is an exterior member of the sensor insertion device 1 that defines the hollow portion. As illustrated in FIG. 1, the housing 2 includes a cylindrical side wall portion 14 that defines the side wall opening 4 and a top wall portion 15 that is integrally formed at one end of the side wall portion 14 oriented in the removal direction A. The housing 2 does not have a bottom wall at a position opposed to the top wall portion 15 but defines an open portion 16 that communicates with the hollow portion in the housing 2.

As illustrated in FIG. 1, the side wall portion 14 of the embodiment has shaft support portions 17 protruding radially outward and opposed to each other with the side wall opening 4 and the hollow portion in the housing 2 sandwiched therebetween. A rotation shaft portion 21 in the operation member 3 is rotatably attached to the shaft support portions 17. The two shaft support portions 17 of the embodiment are provided at positions opposed to each other with the operation member 3 sandwiched therebetween in the circumferential direction of the side wall portion 14. In addition, as illustrated in FIG. 1, the side wall portion 14 of the embodiment defines an opening 18 at positions opposed to each other with the side wall opening 4 and the hollow portion in the housing 2 sandwiched therebetween such that the operation member 3 rotating around the rotation shaft portion 21 acts on the retaining member 32 of the first holding mechanism 8a positioned in the housing 2.

As illustrated in FIG. 1, the top wall portion 15 of the embodiment defines a top wall opening 19. An annular operation portion 29 for the person to be measured or the like to achieve the energy accumulated state (charge the first elastic member 5 and the second elastic member 6) protrudes toward the outside of the housing 2 through the top wall opening 19.

The internal structure of the sensor insertion device 1 is put into the housing 2 from the open portion 16 defined by the one end of the side wall portion 14 of the housing 2 oriented in the insertion direction B. In addition, the internal structure of the sensor insertion device 1 put into the housing 2 can be caught in the housing 2, for example, by sliding part of the fixed member 22 constituting the elastic energy variable mechanism 7 described later onto a projection portion formed on the inner surface of the side wall portion 14 of the housing 2 and crossing over the projection portion. Accordingly, providing the convex-concave retaining portion or the like between the internal structure of the sensor insertion device 1 and the housing 2 makes it possible to prevent the internal structure of the sensor insertion device 1 from coming off the open portion 16 of the housing 2.

[Operation Member 3]

The operation member 3 includes a main body portion 20 that is to be operated by a person to be measured such as a patient or medical personnel, and the rotation shaft portion 21 that is integrated with the main body portion 20 or is fixed to the main body portion 20 and is attached to the shaft support portions 17 of the housing 2 such that the main body portion 20 is rotatable.

The main body portion 20 of the embodiment is almost rectangular plate-like in shape and has the rotation shaft portion 21 on opposed end surfaces oriented in the direction perpendicular to the thickness direction. The person to be measured and the medical personnel pushes the main body portion 20 of the operation member 3 (see the hollow arrow in FIG. 1) to insert the sensor 101 and the needle member 102 into the living body of the person to be measured. Performing the operation allows the main body portion 20 of the operation member 3 to rotate around the rotation shaft portion 21 and act on the retaining member 32 of the first holding mechanism 8a through the opening 18 defined by the side wall portion 14 of the housing 2. When the main body portion 20 acts on the retaining member 32, the first elastic member 5 can be released from hold of the first holding mechanism 8a. This will be described later in detail. The operation member 3 of the embodiment is rotatably attached to the housing 2, but the operation member 3 is not limited to this configuration as far as the operation member 3 is capable of releasing the first elastic member 5 from the held state.

[Elastic Energy Variable Mechanism 7]

Figure 7A:
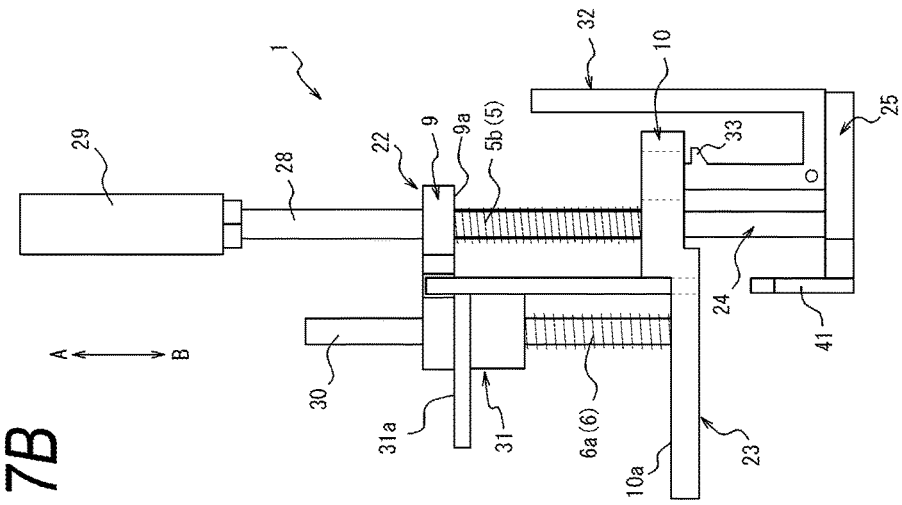
FIGS. 7A and 7B are front and side views illustrating the sensor insertion device illustrated in FIGS. 4A and 4B removed from the replacement part illustrated in FIGS. 4A and 4B and brought into the energy accumulated state in which another replacement part is attachable.
Figure 7B:
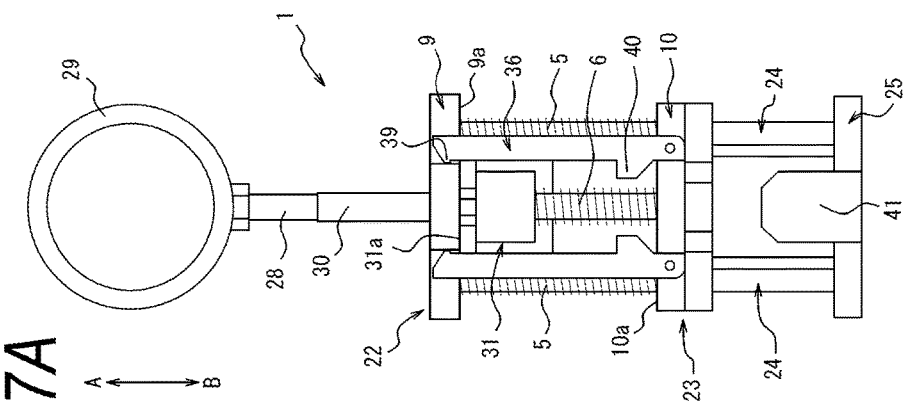

FIGS. 4A to 7B illustrate respectively the state in which the replacement part 100 is attached to the sensor insertion device 1 in the energy accumulated state (see FIGS. 4A and 4B), the state in which the first elastic energy accumulated in the first elastic member 5 is used while the second elastic energy is accumulated in the second elastic member 6 so that the needle member 102 reaches the insertion position (see FIGS. 5A and 5B), the state in which the second elastic energy accumulated in the second elastic member 6 is used so that the needle member 102 reaches the removal position (see FIGS. 6A and 6B), and the state in which the sensor insertion device 1 detached from the replacement part 100 is brought into the energy accumulated state again such that another replacement part 100 is attachable (see FIGS. 7A and 7B). FIGS. 4A, 5A, 6A, and 7A are front views of these states, FIGS. 4B, 5B, 6B, and 7B are side views of these states. FIGS. 4 to 7 do not illustrate the housing 2 and the operation member 3 as well as FIGS. 2 and 3. The "front view" of the sensor insertion device 1 here means the view of the side on which the side wall opening 4 of the housing 2 is formed, of the sensor insertion device 1, and the "side view" of the sensor insertion device 1 here means the view of the right or left side of the sensor insertion device 1.

First, referring to FIGS. 1 to 7, the members of the elastic energy variable mechanism 7 of the embodiment will be described. As illustrated in FIGS. 1 to 7, the elastic energy variable mechanism 7 of the embodiment includes the fixed member 22 that is fixed in position with respect to the housing 2 and the first movable member 23 that is movable with respect to the fixed member 22.

The fixed member 22 includes a bar-like guide portion 24 that extends in the removal direction A (or the insertion direction B), a support base portion 25 that is provided at one end of the guide portion 24 oriented in the insertion direction B, and the movement restriction portion 9 that is provided at one end of the guide portion 24 oriented in the removal direction A.

A plurality of (two in the embodiment) guide portions 24 is provided between the support base portion 25 and the movement restriction portion 9, and insertion springs 5a and 5b as the first elastic member 5 are attached to the circumference of each of the guide portions 24. In other words, the guide portion 24 extends in the hollow portion defined by the insertion springs 5a and 5b as the first elastic member 5.

Both ends of the guide portion 24 are coupled to the support base portion 25 and the movement restriction portion 9 while penetrating through insertion holes defined by the main body portion 10 of the first movable member 23.

The support base portion 25 of the embodiment is plate-like in shape with the thickness direction oriented in the extension direction of the guide portion 24 (the removal direction A and the insertion direction B). At the time of insertion of the needle member 102, a bottom surface 25b of the support base portion 25 oriented in the insertion direction B abuts with the surface of the living body.

The movement restriction portion 9 of the embodiment is positioned in the removal direction A with respect to the first elastic member 5 and the second elastic member 6 to restrict the movement in the removal direction A of the end portions of the first elastic member 5 and the second elastic member 6 oriented in the removal direction A. The movement restriction portion 9 of the embodiment is plate-like in shape with the thickness direction oriented in the extension direction of the guide portion 24 (the removal direction A and the insertion direction B). Further, the movement restriction portion 9 of the embodiment has a first guide hole 27a and a second guide hole 27b penetrating through the movement restriction portion 9 in the thickness direction at positions different from the positions to which the guide portions 24 are coupled (see FIGS. 2 and 3).

The fixed member 22 of the embodiment includes bar-like members constituting the guide portions 24, a bottom plate member that is coupled to ends of the bar-like members and constitutes the support base portion 25, and a top plate member that is coupled to ends of the bar-like members and constitutes the movement restriction portion 9. However, the fixed member 22 is not limited to this configuration as far as the fixed member 22 includes a guide portion, a support base portion, and a movement restriction portion. Therefore, for example, one or two members may constitute the guide portion, the support base portion, and the movement restriction portion, or four or more members may constitute these portions in combination.

The first movable member 23 includes the plate-like main body portion 10 that changes the opposing distance to the movement restriction portion 9, a bar-like protrusion portion 28 that protrudes from the main body portion 10 in the removal direction A and extends outward through the first guide hole 27a in the movement restriction portion 9 (see FIG. 2 and others) and the top wall opening 19 of the top wall portion 15 in the housing 2, the annular operation portion 29 that is provided at the distal end of the bar-like protrusion portion 28 oriented in the removal direction A, and a bar-like guide portion 30 that protrudes from the main body portion 10 in the removal direction A at a position different from the position of the bar-like protrusion portion 28 and is movable in the second guide hole 27b of the movement restriction portion 9.

The main body portion 10 of the embodiment is plate-like in shape with the thickness direction oriented in the extension direction of the guide portion 24 (the removal direction A and the insertion direction B). More specifically, the main body portion 10 of the embodiment is a plate member that includes a first plate portion that is in abutment with the first elastic member 5, and a second plate portion that is integrally formed with the first plate portion via a step and is in abutment with the second elastic member 6.

Further, the main body portion 10 is positioned in the insertion direction B with respect to the first elastic member 5 and the second elastic member 6, and is movable along the guide portion 24 between the movement restriction portion 9 of the fixed member 22 and the support base portion 25. Therefore, the main body portion 10 is movable along the guide portion 24 of the fixed member 22 to change the opposing distance to the movement restriction portion 9 of the fixed member 22. Moving the main body portion 10 in the removal direction A and the insertion direction B allows the first elastic member 5 and the second elastic member 6 to elastically deform at the same time between the main body portion 10 and the movement restriction portion 9.

The bar-like protrusion portion 28 protrudes from the main body portion 10 in the removal direction A, penetrates through the first guide hole 27a in the movement restriction portion 9 (see FIG. 2 and others) and extends to the outside of the housing 2. The bar-like protrusion portion 28 has the operation portion 29 at the distal end. That is, the bar-like protrusion portion 28 couples together the main body portion 10 and the operation portion 29. The person to be measured and medical personnel can move the main body portion 10 in the removal direction A by pulling and operating the operation portion 29 in the removal direction A.

The guide portion 30 protrudes from the main body portion 10 in the removal direction A at the position different from the position of the bar-like protrusion portion 28 and is movable in the second guide hole 27b of the movement restriction portion 9 (see FIG. 2 and others) in the removal direction A and the insertion direction B. The return spring 6a as the second elastic member 6 and the second movable member 31 are attached to the guide portion 30 between the movement restriction portion 9 and the main body portion 10. In other words, the guide portion 30 extends through the hollow portion defined by the return spring 6a as the second elastic member 6 and the insertion hole defined by the second movable member 31. The second elastic member 6 and the second movable member 31 are disposed in this order along the removal direction A.

A top surface 10a of the main body portion 10 positioned in the removal direction A constitutes the surface for receiving the insertion springs 5a and 5b as the first elastic member 5 and the return spring 6a as the second elastic member 6. Specifically, the ends of the insertion springs 5a and 5b as the first elastic member 5 oriented in the insertion direction Bare in abutment with the top surface 10a of the main body portion 10. In addition, one end of the return spring 6a as the second elastic member 6 oriented in the insertion direction B is in abutment with the top surface 10a of the main body portion 10 as well.

Further, a bottom surface 9a of the movement restriction portion 9 positioned in the insertion direction B constitutes the surface for receiving the insertion springs 5a and 5b as the first elastic member 5. That is, ends of the insertion springs 5a and 5b as the first elastic member 5 oriented in the removal direction are in abutment with the bottom surface 9a of the movement restriction portion 9. The second movable member 31 is interposed between the bottom surface 9a of the movement restriction portion 9 positioned in the insertion direction B and the end of the return spring 6a as the second elastic member 6 oriented in the removal direction A as described above. The second movable member 31 constitutes the surface for receiving the end of the return spring 6a as the second elastic member 6 oriented in the removal direction A, and the second movable member 31 can be in abutment with the second elastic member 6. That is, the end of the return spring 6a as the second elastic member 6 oriented in the removal direction A is not in abutment with the bottom surface 9a of the movement restriction portion 9.

The first movable member 23 of the embodiment includes a plate member constituting the main body portion 10, a bar-like member constituting the bar-like protrusion portion 28 that is attached to the plate member, an annular member constituting the annular operation portion 29 that is attached to the distal end of the bar-like member, and a bar-like member constituting the guide portion 30 that is attached to the plate member constituting the main body portion 10 at a position different from the position of the bar-like member constituting the bar-like protrusion portion 28. However, the first movable member 23 is not limited to this configuration as far as the first movable member 23 includes a main body portion, a bar-like protrusion portion, an operation portion, and a guide portion. Therefore, one to three members may constitute the main body portion, the bar-like protrusion portion, the operation portion, and the guide portion, or five or more members may constitute these portions in combination.

In the embodiment, the fixed member 22 and the first movable member 23 constitute the elastic energy variable mechanism 7. The elastic energy variable mechanism 7 can change the sensor insertion device 1 from the state in which the first elastic energy is not accumulated in the first elastic member 5 and the second elastic energy is not accumulated in the second elastic member 6 (see FIGS. 6A and 6B) to the energy accumulated state (see FIGS. 4 and 7). The operation of charging the first elastic member 5 and the second elastic member 6 to turn the sensor insertion device 1 into the energy accumulated state will be described below.

The elastic energy variable mechanism 7 of the embodiment can achieve the energy accumulated state in which the first elastic energy is accumulated in the first elastic member 5 and the second elastic energy is accumulated in the second elastic member 6 by moving the main body portion 10 in the removal direction A such that the opposing distance to the movement restriction portion 9 becomes short and subjecting the first elastic member 5 and the second elastic member 6 to compressive deformation between the main body portion 10 and the movement restriction portion 9. FIGS. 1 to 4 and 7 illustrate the sensor insertion device 1 in the energy accumulated state.

More specifically, the operation portion 29 positioned outside of the housing 2 (see FIG. 1) is held and moved in the removal direction A with an application of force. Since the main body portion 10 is coupled to the operation portion 29 via the bar-like protrusion portion 28, the main body portion 10 can move in the removal direction A against the resilience of the first elastic member 5 and the second elastic member 6 by the force applied to the operation portion 29 in the removal direction A. That is, when the main body portion 10 moves in the removal direction A, the opposing distance between the main body portion 10 and the movement restriction portion 9 becomes short, and the insertion springs 5a and 5b as the first elastic member 5 undergo compressive deformation between the top surface 10a of the main body portion 10 and the bottom surface 9a of the movement restriction portion 9. In addition, the return spring 6a as the second elastic member 6 undergoes compressive deformation between the top surface 10a of the main body portion 10 and the bottom surface 9a of the movement restriction portion 9, more specifically, between the top surface 10a of the main body portion 10 and the second movable member 31.

Then, when the opposing distance between the main body portion 10 and the movement restriction portion 9 is equal to or less than a predetermined distance, the energy accumulated state is achieved.

When the main body portion 10 moves in the removal direction A, the guide portion 30 of the first movable member 23 moves in the removal direction A as well through the second guide hole 27b in the movement restriction portion 9 (see FIG. 2 and others). However, the second movable member 31 abuts with the bottom surface 9a of the movement restriction portion 9 and does not move from the position of the bottom surface 9a of the movement restriction portion 9 in the removal direction A. That is, the bottom surface 9a of the movement restriction portion 9 does not directly abut with the second elastic member 6. However, when the main body portion 10 is moved in the removal direction A, the bottom surface 9a of the movement restriction portion 9 applies reaction force to the second elastic member 6 via the second movable member 31. Therefore, when the main body portion 10 is moved in the removal direction A, the bottom surface 9a of the movement restriction portion 9 acts as a reaction wall to apply reaction force to the first elastic member 5 and the second elastic member 6. Accordingly, the first elastic member 5 and the second elastic member 6 can undergo compressive deformation between a top surface 10a of the main body portion 10 and the bottom surface 9a of the movement restriction portion 9.

When the main body portion 10 of the first movable member 23 moves in the removal direction A, the insertion springs 5a and 5b as the first elastic member 5 undergo compressive deformation while sliding on the outer walls of the guide portions 24. That is, the deforming directions of the first elastic member 5 are limited by the guide portions 24 to the removal direction A and the insertion direction B. In addition, the return spring 6a as the second elastic member 6 undergoes compressive deformation while sliding on the outer wall of the guide portion 30, and the deforming directions of the return spring 6a as the second elastic member 6 are limited to the removal direction A and the insertion direction B as well. Further, the main body portion 10 moves while the inner wall of the main body portion 10 defining the insertion hole slides on the outer walls of the guide portions 24 and the outer wall of the guide portion 30 slides on the inner wall of the movement restriction portion 9 defining the second guide hole 27b. Accordingly, the main body portion 10 is guided by the guide portions 24 and the second guide hole 27b such that the main body portion 10 is moved in the removal direction A and the insertion direction B. That is, in the embodiment, the deformation directions of the first elastic member 5 and the second elastic member 6 and the moving directions of the first movable member 23 are limited by the fixed member 22 to the removal direction A and the insertion direction B.

As described above, according to the elastic energy variable mechanism 7 of the embodiment, moving the operation portion 29 in the removal direction A makes it possible to subject the first elastic member 5 and the second elastic member 6 to compressive deformation and charge the first elastic member 5 and the second elastic member 6. That is, moving the operation portion 29 in the removal direction A makes it possible to bring the sensor insertion device 1 into the energy accumulated state.

Further, it is preferable that moving the operation portion 29 in the removal direction A to allow the first elastic member 5 and the second elastic member 6 to undergo compressive deformation at the same time and be charged at the same time as in the elastic energy variable mechanism 7 of the embodiment. According to this configuration, it is possible to achieve the energy accumulated state by fewer operations.

[First Holding Mechanism 8a]

As illustrated in FIGS. 2 to 7, the first holding mechanism 8a includes the retaining member 32 constituting the retaining portion to retain the main body portion 10 of the first movable member 23 in the energy accumulated state. Specifically, the first holding mechanism 8a of the embodiment is formed from the fixed member 22, the first movable member 23, and the retaining member 32. More specifically, the first holding mechanism 8a of the embodiment includes the support base portion 25 of the fixed member 22, the main body portion 10 of the first movable member 23 and the retaining member 32 that is changeable in position between the state in abutment with the main body portion 10 and the state not in abutment with the main body portion 10 depending on the movement of the main body portion 10 with respect to the support base portion 25.

The retaining member 32 of the embodiment includes a claw portion 33 that is rotatable with respect to the support base portion 25 and is changeable in position between the state in abutment with a bottom surface 10b of the main body portion 10 and the state not in abutment with the bottom surface 10b of the main body portion 10 by rotating with respect to the support base portion 25. As illustrated in FIGS. 4A and 4B, in the energy accumulated state, the claw portion 33 is in abutment with the bottom surface 10b of the main body portion 10 to restrict the movement of the main body portion 10 in the insertion direction B. When the retaining member 32 in the state illustrated in FIGS. 4A and 4B rotates, the claw portion 33 and the bottom surface 10b of the main body portion 10 are disengaged from each other, and the main body portion 10 moves in the insertion direction B by the resilience of the first elastic member 5 (see FIGS. 5 and 6).

More specifically, the retaining member 32 of the embodiment is U-shaped and is formed from three plate portions. That is, the retaining member 32 of the embodiment includes a retaining plate portion 11 having the claw portion 33, an engagement plate portion 34 that engages with the operation member 3 by operation of the operation member 3 positioned outside of the housing 2, and a coupling plate portion 35 that transfers the force acting on the engagement plate portion 34 to the retaining plate portion 11 by operation of the operation member 3.

The retaining plate portion 11 includes the claw portion 33 positioned at one end oriented in the removal direction A and the rotation shaft portion 21 that is positioned at one end oriented in the insertion direction B to guide the retaining plate portion 11 in such a manner as to be rotatable with respect to the support base portion 25. The main body portion 10 has the insertion hole in which the retaining plate portion 11 is movable. Therefore, when the claw portion 33 is in abutment with the bottom surface 10b of the main body portion 10 (see FIGS. 4A and 4B) and the operation member 3 is operated to apply force to the engagement plate portion 34, the retaining plate portion 11 rotates around the rotation shaft portion 21. When the claw portion 33 and the bottom surface 10b of the main body portion 10 are disengaged from each other, the main body portion 10 moves in the insertion direction B by the resilience of the elastic member 5, and the retaining plate portion 11 penetrates through the insertion hole in the main body portion 10 at that time. Then, the needle member 102 is placed in the insertion position, that is, the bottom surface 10b of the main body portion 10 is brought into abutment with a top surface 25a of the support base portion 25 in the embodiment (see FIGS. 5 and 6). The rotation shaft portion 21 of the retaining plate portion 11 may be attached to the support base portion 25 or may be attached to the housing 2.

In addition, the retaining member 32 is subjected to the biasing force under its own weight or by the action of a biasing means not illustrated so that the retaining plate portion 11 is rotationally returned from the state illustrated in FIGS. 5A and 5B (in which the retaining plate portion 11 is not perpendicular to the top surface 25a of the support base portion 25 but is inclined with respect to the top surface 25a of the support base portion 25) to the state illustrated in FIGS. 4A and 4B (in which the retaining plate portion 11 is almost perpendicular to the top surface 25a of the support base portion 25). Accordingly, to recharge the first elastic member 5 and the second elastic member 6 by the elastic energy variable mechanism 7 (to change the sensor insertion device 1 from the state illustrated in FIGS. 6A and 6B to the state illustrated in FIGS. 7A and 7B), once the bottom surface 10b of the main body portion 10 reaches the position nearer the removal direction A than the claw portion 33, the retaining plate portion 11 returns to the posture illustrated in FIGS. 4A and 4B (see FIGS. 7A and 7B). Therefore, even though the person to be measured or the like releases a hand from the operation portion 29 in this state, the bottom surface 10b of the main body portion 10 abuts with the claw portion 33 of the retaining plate portion 11 and the main body portion 10 is caught in the retaining plate portion 11 in the energy accumulated state (see FIGS. 4A and 4B).

In the embodiment, the first holding mechanism 8a is formed from the support base portion 25 of the fixed member 22, the main body portion 10 of the first movable member 23, and the retaining member 32. However, the present invention is not limited to the configuration of the embodiment as far as the first holding mechanism 8a is configured to hold the posture of the first elastic member 5 in the energy accumulated state and release the first elastic member 5 from the holding state. For example, in the case of using the elastic energy variable mechanism 7 of the embodiment, the first holding mechanism includes at least a retaining portion that is deformable or movable between the retaining position where the main body portion 10 is caught and the release position where the main body portion 10 is released from the caught state. Therefore, the retaining member 32 and the fixed member 22 are not necessarily separate members but the retaining portion may be integrated with the fixed member so that the fixed member also acts as the retaining member. Alternatively, the housing may be provided with the retaining portion to retain the first movable member in the energy accumulated state or the housing may be provided with a retaining member including a retaining portion to retain the first movable member in the energy accumulated state. Further, the retaining member 32 of the embodiment is a single member formed from three plate portions but the retaining member 32 is not limited to the shape and the number of members described above. For example, the shape and the number of members of the retaining member 32 can be changed as appropriate depending on the configuration of the elastic energy variable mechanism, for example.

[Second Holding Mechanism 8b]

The second holding mechanism 8b includes the first movable member 23, the second movable member 31, and the lock members 36. More specifically, the second holding mechanism 8b of the embodiment includes the main body portion 10 and the guide portion 30 of the first movable member 23, the second movable member 31 that is sandwiched between the movement restriction portion 9 and the second elastic member 6 and is movable with respect to the movement restriction portion 9 and the main body portion 10 along the guide portion 30, and the lock members 36 that engage with the second movable member 31 biased by the second elastic member 6 in the removal direction A in the energy accumulated state to fix the position of the second movable member 31 with respect to the main body portion 10.

The second movable member 31 of the embodiment includes a cylindrical main body portion 37 that defines a insertion hole and a plate-like protrusion portion 38 that extends radially outward from one end of the main body portion 37 oriented in the removal direction A. As illustrated in FIGS. 2 to 7, the guide portion 30 of the first movable member 23 extends through the insertion hole defined by the main body portion 37 of the second movable member 31 and the hollow portion defined by the return spring 6a as the second elastic member 6. The protrusion portion 38 has a second sandwich portion 47 described later to sandwich the needle member 102 of the replacement part 100.

Ends of the lock members 36 of the embodiment are rotatably attached to the main body portion 10 of the first movable member 23, and other ends of the lock members 36 extend from the main body portion 10 in the removal direction A. The other ends of the lock members 36 have claw portions 39 engageable with the second movable member 31. The lock members 36 have other claw portions 40 that engage with a disengagement member 41 on the support base portion 25 of the fixed member 22 to disengage the claw portions 39 and the second movable member 31 when the needle member 102 reaches the insertion position.

First, in the energy accumulated state illustrated in FIGS. 4A and 4B, while the second movable member 31 is biased by the second elastic member 6 in the removal direction A, a top surface 31a of the second movable member 31 is in abutment with the claw portions 39 of the lock members 36. That is, the second movable member 31 is kept in abutment with the claw portions 39 of the lock members 36 by the biasing force of the second elastic member 6.

When the main body portion 10 in the state illustrated in FIGS. 4A and 4B is released from the first holding mechanism 8a, the main body portion 10 can move in the insertion direction B by the first elastic energy of the first elastic member 5 to move the needle member 102 of the attached replacement part 100 to the insertion position (see FIGS. 5A and 5B). Then, when the needle member 102 reaches the insertion position, the disengagement member 41 on the support base portion 25 is brought into abutment with the claw portions 40 of the lock members 36, and the lock members 36 are pressed by the disengagement member 41 in the direction perpendicular to the insertion direction B (the horizontal direction in FIGS. 5A and 5B). Therefore, the lock members 36 rotate around ends rotatably attached to the main body portion 10 of the first movable member 23 (see FIG. 6A). Accordingly, the second movable member 31 and the claw portions 39 of the lock members 36 are disengaged from each other, and the second movable member 31 moves in the removal direction A with respect to the main body portion 10 by the second elastic energy accumulated in the second elastic member 6 (see FIGS. 6A and 6B). Along with the movement of the second movable member 31 in the removal direction A with respect to the first movable member 23, the needle member 102 sandwiched in the second sandwich portion 47 at the protrusion portion 38 of the second movable member 31 moves to the removal position (see FIGS. 6A and 6B).

The disengagement member 41 is rectangular plate-like in shape and is fixed to the support base portion 25 of the fixed member 22. In the front view of FIG. 4A, the disengagement member 41 has tapered portions 42 slidable on the claw portions 40 of the lock members 36, which are formed on the right and left sides of the end portions oriented in the removal direction A. In addition, in the front view of FIG. 4A, the lock members 36 are opposed to each other on the right and left sides with the second movable member 31 sandwiched therebetween. The claw portions 40 of the lock members 36 have tapered portions 43 slidable on the tapered portions 42 of the disengagement member 41. In the front view of FIG. 4A, the tapered portions 42 of the disengagement member 41 positioned on the right and left sides are inclined in the removal direction A such that the opposing distance between the right and left sides gradually decreases. Similarly, in the front view of FIG. 4A, the tapered portions 43 of the claw portions 40 on the right and left lock members 36 are inclined in the removal direction A such that the opposing distance between the right and left sides gradually decreases.

Accordingly, when the main body portion 10 moves in the insertion direction B and the disengagement member 41 enters between the opposed lock members 36, the tapered portions 42 of the disengagement member 41 slide on the claw portions 40 of the lock members 36 and press the tapered portions 43 in the direction that increases the opposing distance between the two opposed lock members 36. The opposed lock members 36 are rotated around the rotation shaft fixed to the main body portion 10 by the pressing force such that the opposing distance becomes longer. As a result, the claw portions 39 at the ends of the lock members 36 oriented in the removal direction A separate from the second movable member 31, and the second movable member 31 moves in the removal direction A by the resilience of the second elastic member 6 (see FIGS. 6A and 6B). As illustrated in FIGS. 2 to 7, the main body portion 10 has the insertion hole through which the disengagement member 41 attached to the support base portion 25 is insertable.

As described above, the sensor insertion device 1 of the embodiment includes a switch mechanism that, when the needle member 102 reaches the insertion position (see FIGS. 5A and 5B), can switch alternatively from the movement of the needle member 102 in the insertion direction B by the biasing force of the first elastic member 5 (the resilience of the insertion springs 5a and 5b having undergone compressive deformation in the embodiment) to the movement of the needle member 102 in the removal direction A by the biasing force of the second elastic member 6 (the resilience of the return spring 6a having undergone compressive deformation in the embodiment).

The alternative switching here means that switching takes place between the movement of the needle member 102 to the insertion position at the time of insertion and the movement of the needle member 102 to the removal position at the time of removal under the influence of different elastic members. In the embodiment, the alternative switching means that switching takes place between the movement of the needle member 102 at the time of insertion under the influence of the resilience of the insertion springs 5a and 5b and under no influence of the resilience of the return spring 6a and the movement of the needle member 102 at the time of removal under the influence of the resilience of the return spring 6a and under no influence of the resilience of the insertion springs 5a and 5b.

Specifically, the switch mechanism of the embodiment includes the claw portions 40 of the lock members 36 and the disengagement member 41 attached to the support base portion 25. According to this configuration of the sensor insertion device 1 of the embodiment, it is possible to allow the insertion of the sensor 101 and the needle member 102 and the removal of the needle member 102 to be automatically performed in conjunction with each other. Therefore, as compared to the configuration in which the insertion of the sensor 101 and the needle member 102 and the removal of the needle member 102 are performed by separate operations, it is possible to shorten the time from the insertion to the removal of the needle member 102, thereby lessening the pain of the person to be measured such as a patient.

As described above, according to the second holding mechanism 8b of the embodiment, the posture of the second elastic member 6 is held in the energy accumulated state (see FIGS. 4A and 4B) and for a period of time during which, after the release of the first elastic member 5 from the state held by the first holding mechanism 8a in the energy accumulated state, the needle member 102 is moved to the insertion position by the first elastic energy (see FIGS. 5A and 5B). Then, after the needle member 102 reaches the insertion position, the switch mechanism releases the second elastic member 6 from the state held by the second holding mechanism 8b, and the needle member 102 moves to the removal position.

Next, the operation of the second holding mechanism 8b for changing from the state in which the second elastic energy is not accumulated in the second elastic member 6 to the energy accumulated state will described.

As described above, the energy accumulated state can be achieved by the elastic energy variable mechanism 7 moving the main body portion 10 in the removal direction A. First, when the main body portion 10 starts to move in the removal direction A, the claw portions 40 of the lock members 36 separate from the disengagement member 41. Accordingly, the lock members 36 turn to the states illustrated in FIGS. 4 and 5. Then, when the main body portion 10 further moves in the removal direction A against the elastic force of the first elastic member 5 and the second elastic member 6, tapered portions 44 of the claw portions 39 of the lock members 36 start to slide on the second movable member 31 in abutment with the bottom surface 9a of the movement restriction portion 9. The opposed lock members 36 are subjected to the pressing force by the sliding of the tapered portions 44 of the claw portions 39 and the second movable member 31 such that the opposing distance becomes longer. The opposed lock members 36 are rotated by the pressing force around the rotation shaft attached to the main body portion 10. Then, the lock members 36 return to the original posture when the claw portions 39 come over the second movable member 31, and the claw portions 39 are caught in the second movable member 31. Accordingly, the second holding mechanism 8b can hold the posture of the second elastic member 6 in the energy accumulated state (see FIGS. 4 and 7).

The second holding mechanism 8b of the embodiment is formed from the first movable member 23, the second movable member 31, and the lock members 36. However, the second holding mechanism 8b is not limited to this configuration as far as the second holding mechanism 8b can hold the posture of the second elastic member in the energy accumulated state and for the period of time during which the needle member moves to the insertion position. For example, the second holding mechanism 8b of the embodiment holds the posture of the second elastic member 6 by engaging the claw portions 39 of the lock members 36 with the second movable member 31 in the energy accumulated state (see FIGS. 4A and 4B) and for the period of time during which the needle member 102 moves to the insertion position (see FIGS. 5A and 5B). Alternatively, the second holding mechanism 8b may hold the posture of the second elastic member 6 in which the second elastic energy is accumulated by not engaging the claw portions 39 with the second movable member 31 but engaging the movement restriction portion 9 of the fixed member 22 with the second movable member 31 in the energy accumulated state and by not engaging the movement restriction portion 9 with the second movable member 31 but engaging the claw portions 39 with the second movable member 31 for the period of time during which the needle member 102 moves to the insertion position. In other words, the lock members 36 may hold the second elastic member 6 with the second elastic energy accumulated at least for the period of time during which the needle member 102 moves to the insertion position, and another member constituting the second holding mechanism (for example, the movement restriction portion 9 of the fixed member 22) may hold the posture of the second elastic member 6 in the energy accumulated state. To achieve this configuration, the second holding mechanism is formed from the other member described above (for example, the movement restriction portion 9 of the fixed member 22), the main body portion 10 and the guide portion 30 of the first movable member 23, the second movable member 31, and the lock members 36.

The second holding mechanism 8b of the embodiment includes the lock members 36 separate from the first movable member 23 and the second movable member 31. Alternatively, the lock members may be integrated with the first movable member or the second movable member so that the first movable member or the second movable member also acts as the lock members, for example, as far as the lock members are configured to hold the posture of the second elastic member with the second elastic energy accumulated.

In the embodiment, the disengagement member 41 is attached to the support base portion 25 of the fixed member 22. However, the disengagement member 41 is not limited to this configuration but may be attached to another portion of the fixed member 22, for example. In addition, the disengagement member 41 of the embodiment is formed from a member separate from the fixed member 22, but the disengagement portion may be integrated with the fixed member so that the fixed member also acts as the disengagement member. That is, the disengagement member only includes the disengagement portion that disengages the lock portion from the second movable member when the needle member reaches the insertion position.

[Attachment Portion 45]

The sensor insertion device 1 includes an attachment portion 45 to which the replacement part 100 is detachably attached. Specifically, the attachment portion 45 of the embodiment includes a first sandwich portion 46 that is formed from the first movable member 23 and sandwiches the sensor housing 103 of the replacement part 100 and the second sandwich portion 47 that is formed from the second movable member 31 and sandwiches the needle member 102 of the replacement part 100.

The first sandwich portion 46 is formed at one end of the main body portion 10 of the first movable member 23 oriented in the direction perpendicular to the insertion direction B. Specifically, the first sandwich portion 46 is formed at the second plate portion of the main body portion 10 receiving one end of the second elastic member 6 oriented in the insertion direction B in the vicinity of the portion receiving the second elastic member 6. More specifically, the second plate portion of the main body portion 10 has a cutout at the outer edge and the sensor housing 103 is fitted into the cutout and sandwiched in the second plate portion. That is, the first sandwich portion 46 is formed from an inner wall defining the cutout. The inner wall of the main body portion 10 defining the cutout of the embodiment is formed in the order of a guide portion, a constricted portion, and the first sandwich portion 46 from the outer edge of the main body portion 10. The guide portion constitutes an entrance portion into which the sensor housing 103 is attached from the outside, and is tapered with decrease in the opposing distance with increasing proximity to the first sandwich portion 46. The first sandwich portion 46 is shaped in correspondence with the outer shape of the sensor housing 103 and can sandwich the sensor housing 103 by pressing the circumference of the sensor housing 103. The constricted portion between the guide portion and the first sandwich portion 46 suppresses the movement of the sensor housing 103 sandwiched in the first sandwich portion 46 toward the guide portion.

The second sandwich portion 47 is formed at one end of the protrusion portion 38 of the second movable member 31 oriented in the direction perpendicular to the insertion direction B. Specifically, the second sandwich portion 47 is positioned in the removal direction A with respect to the first sandwich portion 46 and is formed from an inner wall defining a cutout as the first sandwich portion 46 described above.

As described above, the attachment portion 45 of the embodiment is formed from the first sandwich portion 46 in the first movable member 23 and the second sandwich portion 47 in the second movable member 31. The replacement part 100 can be attached to the attachment portion 45 while the postures of the first elastic member 5 and the second elastic member 6 in the energy accumulated state are held by the first holding mechanism 8a and the second holding mechanism 8b (see FIGS. 4A and 4B).

<Replacement Part 100>

Next, the replacement part 100 according to one embodiment of the present invention will be described. FIGS. 8A and 8B illustrate form changes of the replacement part 100. FIG. 8A illustrates the state of the replacement part 100 that is attachable to the sensor insertion device 1. FIG. 8B illustrates the state of the replacement part 100 in which, after the movement of the needle member 102 to the insertion position by the sensor insertion device 1, the needle member 102 is moved to the removal position by the sensor insertion device 1. FIG. 8C illustrates the state of the replacement part 100 in which the sensor insertion device 1 in the state illustrated in FIG. 8B is removed and the replacement part 100 is split into two portions.

As illustrated in FIGS. 8A through 8C, the replacement part 100 of the embodiment includes the sensor 101, the needle member 102, the sensor housing 103, the hollow member 104, and the sheet member 105 as described above.

[Sensor 101]

The sensor 101 of the embodiment is inserted and left in a living body to detect biological information. Specifically, the sensor 101 of the embodiment includes an optical fiber 150 as a light guiding member that has a distal end left in the living body and a proximal end extending outside of the living body and a detection portion 151 that is provided at a distal end portion 108 of the optical fiber 150 and left in the living body to detect biological information. As the light guiding member, a light waveguide path formed from a light waveguide path film may be used.

The detection portion 151 of the embodiment includes a fluorescent gel including a fluorescent pigment generating fluorescent light by excitation light. The fluorescent gel generates fluorescent light depending on the analyte amount.

The optical fiber 150 is a light guiding path that transfers the excitation light to be applied to the detection portion 151 and the measurement light detected by the detection portion 151. Specifically, a processing device 200 described later is disposed at the proximal end side of the optical fiber 150. The excitation light is generated by a light emission portion 201 of the processing device 200 disposed at the proximal end side of the optical fiber 150 and is applied to the detection portion 151 through the optical fiber 150. The measurement light generated from the excitation light and detected by the detection portion 151 is received by a light receiving portion 202 of an optical detection portion 203 in the processing device 200 through the optical fiber 150.

The optical fiber 150 of the embodiment is held in the sensor housing 103. Specifically, the optical fiber 150 includes a straight portion 107 that extends in an insertion hole 106 defined by the sensor housing 103, a distal end portion 108 that continues from the distal end side of the straight portion 107 and extends outward from the insertion hole 106, a curve portion 109 that continues from the proximal end side of the straight portion 107, and a proximal end portion 110 that continues from the proximal end side of the curve portion 109.

In the state illustrated in FIG. 8A, the straight portion 107 and the distal end portion 108 are positioned in a needle portion 111 of the needle member 102. The detection portion 151 provided at the distal end portion 108 is positioned in the needle portion 111 of the needle member 102 as well in the state illustrated in FIG. 8A. The distal end portion 108 of the optical fiber 150 and the detection portion 151 provided at the distal end portion 108 are inserted and left in a living body by the sensor insertion device 1.

The curve portion 109 extends from the proximal end of the straight portion 107 to the outside of the needle portion 111 through a clearance (i.e. slit) formed in the needle portion 111 of the needle member 102.

[Needle Member 102]

The needle member 102 is inserted together with the sensor 101 into a living body, the distal end side of the sensor 101 (the detection portion 151 and the distal end portion 108 of the optical fiber 150 in the embodiment) is left in the living body, and then the needle member 102 is removed from the living body. Specifically, the needle member 102 includes the needle portion 111 U-shaped in cross section that defines the hollow portion and has a clearance (i.e. slit) in the transverse section, and a needle support portion 113 that supports the needle portion 111.

The needle portion 111 is movable in the insertion hole 106 of the sensor housing 103. Specifically, the needle portion 111 extends in the insertion hole 106 in the state illustrated in FIG. 8A, and moves in the insertion hole 106 in the removal direction A at the time of transition from the state illustrated in FIG. 8A to the state illustrated in FIG. 8B (see the hollow arrow in FIG. 8B). The needle portion 111 accommodates the distal end side of the sensor 101 therein in the state illustrated in FIG. 8A.

The needle support portion 113 is bar-like in shape and has the proximal end portion of the needle portion 111 fixed to the distal end portion thereof. More specifically, the needle support portion 113 extends in the removal direction A and the insertion direction B, and the needle portion 111 protrudes in the insertion direction B from a flange portion 113a provided at the end portion of the needle support portion 113 oriented in the insertion direction B. In addition, the needle support portion 113 has at the end portion thereof oriented in the removal direction A an annular groove portion 114 into which the second sandwich portion 47 formed in the second movable member 31 of the sensor insertion device 1 enters. The flange portion 113a is movable in a hollow portion 121 of the hollow member 104. The flange portion 113a is larger in outer diameter than an insertion hole 126 defined by a top wall portion 124 of the hollow member 104. This prevents the flange portion 113a from coming off the hollow member 104 through the insertion hole 126. Therefore, it is also possible to prevent the needle portion 111 protruding from the flange portion 113a in the insertion direction B from coming off the hollow member 104 through the insertion hole 126.

[Sensor Housing 103]

The sensor housing 103 defines the insertion hole 106 in which the needle member 102 can be moved by the sensor insertion device 1 from the insertion position to the removal position. The sensor housing 103 also defines a guide path 118 that communicates with the insertion hole 106 for the optical fiber 150 that extends from the clearance (i.e. slit) in the needle portion 111 of the needle member 102 to the outside of the needle portion 111.

More specifically, the sensor housing 103 of the embodiment includes a trunk portion 115 columnar in outer shape, a disc-shaped base portion 116 that is integrated with the trunk portion 115 on the insertion direction B side, and a circular cylindrical connection portion 112 that protrudes radially outward from the side wall of the trunk portion 115. The insertion hole 106 is defined by the trunk portion 115 and the base portion 116 and penetrates through the top surface of the trunk portion 115 (the upper surface in FIGS. 8A through 8C) to the bottom surface of the base portion 116 (the lower surface in FIGS. 8A through 8C). A disc-shaped elastic member is disposed in the insertion hole 106. Examples of material for the elastic member include vulcanized rubbers such as butyl rubber, isoprene rubber, silicone rubber, and natural rubber, and thermoplastic elastomers such as styrene elastomer, urethane elastomer, and olefin elastomer. The elastic member seals the sensor housing 103 even after the removal of the needle portion 111 to prevent infection. The guide path 118 is defined by the trunk portion 115 and the connection portion 112. The curve portion 109 and the proximal end portion 110 of the optical fiber 150 extend in the guide path 118.

Further, the top surface of the trunk portion 115 has a fitting groove 117 into which the end portion of the hollow member 104 oriented in the insertion direction B is fitted. When the trunk portion 115 is seen from the top surface side, the fitting groove 117 is square in shape and the insertion hole 106 is positioned in the center of the fitting groove 117. That is, the bottom wall of the fitting groove 117 defines in the center thereof an end opening in the insertion hole 106 oriented in the removal direction A. The shape of the fitting groove 117 in the trunk portion 115 seen from the top surface side is not limited to square but may be circular or polygonal shape other than square.

The connection portion 112 is connectable to the processing device 200 that emits the excitation light and receives the measurement light. The distal end surface of the connection portion 112 defines an end opening of the guide path 118. The guide path 118 extends from the end opening in the connection portion 112 and the trunk portion 115 and communicates with the insertion hole 106.

[Hollow Member 104]

The hollow member 104 of the embodiment is almost rectangular in outer shape and defines the hollow portion 121 that accommodates the needle portion 111 when the needle member 102 moves to the removal position. As illustrated in FIGS. 8A and 8B, the hollow member 104 can be fitted into the fitting groove 117 formed in the top surface of the trunk portion 115 of the sensor housing 103. In addition, as illustrated in FIG. 8C, the hollow member 104 can be easily detached from the fitting groove 117 by moving in the removal direction A.

Specifically, the hollow member 104 of the embodiment includes a rectangular cylinder-shaped side wall portion 122, a bottom wall portion 123 positioned at one end of the side wall portion 122 oriented in the insertion direction B, and a top wall portion 124 positioned at one end of the side wall portion 122 oriented in the removal direction A. The hollow portion 121 is defined by the side wall portion 122, the bottom wall portion 123, and the top wall portion 124.

The hollow member 104 includes a one-way lock portion that, after the movement of the needle member 102 from the insertion position to the removal position, restricts the movement of the needle member 102 back to the insertion position. Specifically, claw portions 125 as the one-way lock portion protruding toward the hollow portion 121 are provided on the inner surface of the side wall portion 122 of the hollow member 104 of the embodiment. As illustrated in FIGS. 8A and 8B, when the needle member 102 moves to the removal position, the flange portion 113a at the needle support portion 113 of the needle member 102 slides on the claw portions 125 and comes over the claw portions 125. As a result, the surface of the flange portion 113a on the insertion direction B side (the lower surface in FIGS. 8A through 8C) abuts with the retaining surfaces 125a of the claw portions 125 (the upper surfaces of the claw portions 125 in FIGS. 8A through 8C) to restrict the return of the needle member 102 in the insertion direction B. Then, the distal end of the needle portion 111 remains in the hollow portion 121 without protruding from an insertion hole 127 in the bottom wall portion 123. Accordingly, as illustrated in FIG. 8C, after the detachment of the replacement part 100 from the sensor insertion device 1, even though the needle member 102 and the hollow member 104 are moved and separated from the sensor 101, the sensor housing 103, and the sheet member 105 (see the hollow arrow in FIG. 8C), the needle portion 111 of the needle member 102 is positioned in the hollow portion 121 of the hollow member 104 to prevent the person to be measured and the medical personnel from touching the needle portion 111 piercing the living body or removed from the living body.

The two claw portions 125 of the embodiment are provided on the two inner surfaces of the side wall portion 122 opposed to each other. However, the number of the wall portions on which the claw portions 125 are provided is not limited to this. For example, the claw portions 125 may be provided on three or four wall portions or only one wall portion.

The bottom wall portion 123 defines the insertion hole 127 in the center thereof. When the bottom wall portion 123 of the hollow member 104 is fitted into the fitting groove 117 in the trunk portion 115 of the sensor housing 103, the insertion hole 127 in the bottom wall portion 123 communicates with the insertion hole 106 in the sensor housing 103. Therefore, when the bottom wall portion 123 of the hollow member 104 is fitted into the fitting groove 117, the needle portion 111 of the needle member 102 can be moved into the hollow portion 121 at the removal position through the insertion hole 106 in the sensor housing 103 and the insertion hole 127 in the bottom wall portion 123. The force of the fit between the fitting groove 117 and the hollow member 104 is larger than the force of sliding and moving the needle support portion 113 in the removal direction. By moving the needle member 102 to the removal position where the needle member 102 is removable from the living body (see FIG. 8B), the flange portion 113a in the needle support portion 113 of the needle member 102 slides on the claw portions 125 on the side wall portion 122 and comes over the claw portions 125, thereby to restrict the movement of the flange portion 113a in the insertion direction B. The force of the fit between the fitting groove 117 and the hollow member 104 is larger than the force of resistance necessary for the flange portion 113a to come over the claw portions 125.

The top wall portion 124 defines the insertion hole 126 in which the needle support portion 113 is movable. As described above, the inner diameter of the insertion hole 126 is smaller than the outer diameter of the flange portion 113a of the needle support portion 113. This prevents the needle member 102 from coming off the hollow member 104 through the insertion hole 126.

[Sheet Member 105]

The sheet member 105 is a thin-walled member with the thickness direction oriented in the removal direction A or the insertion direction B. The surface of the sheet member 105 oriented in the insertion direction B (the lower surface in FIGS. 8A through 8C) is in abutment with the living body and is left together with the sensor 101 and the sensor housing 103 in the living body.

Therefore, a gluing agent may be provided on the lower surface of the sheet member 105 for adhesion to the surface of the living body, for example. According to this configuration, when the needle member 102 is moved by the sensor insertion device 1 to the insertion position, the gluing agent adheres to the surface of the living body. Accordingly, it is possible to prevent the sensor 101 and the sensor housing 103 left in the living body from moving due to body motion or the like. Release paper may be provided on the gluing surface of the sheet-like member.

<Processing Device 200>

Figure 9A:
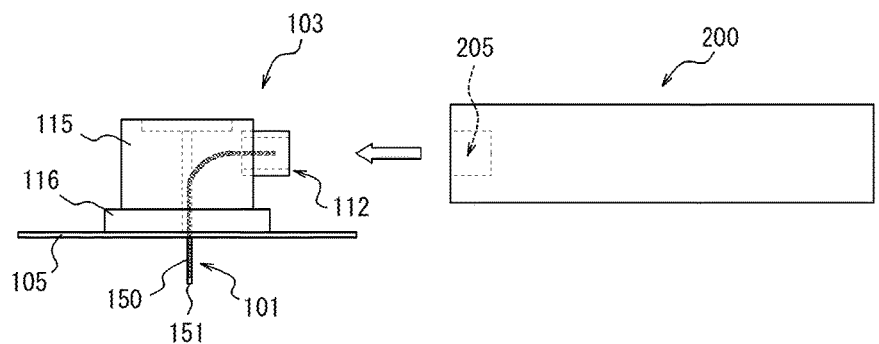
FIG. 9A is a illustrates the state before connection of a sensor housing and a processing device.
Figure 9B:
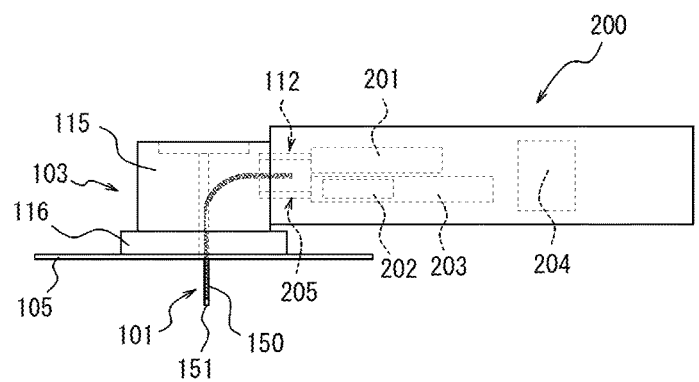
FIG. 9B is a illustrates the state after the connection.

Next, the measurement of biological information using the sensor 101, the sensor housing 103, and the sheet member 105 of the replacement part 100, three of which are left in the living body, will be described. First, the processing device 200 is connected to the connection portion 112 of the sensor housing 103. FIGS. 9A and 9B illustrate the action of connecting the processing device 200 to the connection portion 112. FIG. 9A illustrates the state before the connection, and FIG. 9B illustrates the state in which the processing device 200 in the state of FIG. 9A is moved to the connection portion 112 (see the hollow arrow in FIG. 9A) and the processing device 200 is connected to the connection portion 112. FIG. 9B illustrates the internal configuration of the processing device 200 in a simplified manner.

As illustrated in FIG. 9B, the processing device 200 of the embodiment includes the light emission portion 201 that generates the excitation light to be applied to the detection portion 151 of the sensor 101, the optical detection portion 203 that has the light receiving portion 202 to receive the measurement light (fluorescent light in the embodiment) generated by the detection portion 151 according to the analyte amount, and a processing portion 204 that processes a signal obtained from the optical detection portion 203.

The connection portion 112 has a groove portion in the outer surface to facilitate the positioning of the connection portion 112 and the processing device 200, and the processing device 200 has a protrusion portion that fits into the groove portion in the outer surface of the connection portion 112, for example, thereby to allow connection of the connection portion 112 and the processing device 200. A simplified connection configuration can be used. The processing device 200 illustrated in FIGS. 9A and 9B defines a connection opening 205 to accommodate the circular cylindrical connection portion 112 at the time of connection with the connection portion 112.

[About the Insertion and Removal Actions by the Sensor Insertion Device Assembly 300]

Finally, with reference to FIGS. 1 to 8, the insertion of the sensor 101 and the needle member 102 by the sensor insertion device assembly 300 including the sensor insertion device 1 and the replacement part 100 attached to the sensor insertion device 1 (see FIGS. 3 to 6) and the removal of the needle member 102 by the sensor insertion device assembly 300 will be briefly described.

First, the replacement part 100 is attached by the first holding mechanism 8a and the second holding mechanism 8b to the sensor insertion device 1 that is kept in the energy accumulated state in which the first elastic energy is accumulated in the first elastic member 5 and the second elastic energy is accumulated in the second elastic member 6 (see FIGS. 4A and 4B). The replacement part 100 is attached to the sensor insertion device 1 such that the annular groove portion 114 in the needle support portion 113 of the needle member 102 is sandwiched in the second sandwich portion 47 of the second movable member 31 and the trunk portion 115 of the sensor housing 103 is sandwiched in the first sandwich portion 46 of the first movable member 23 (see FIGS. 4A and 4B).

Next, one end of the side wall portion 14 defining the open portion 16 of the housing 2 in the sensor insertion device 1 is pressed against the surface of the living body of the person to be measured such as a patient. In this state, the operation member 3 is rotationally pushed into the housing 2 (see FIG. 1). By this operation, the retaining member 32 constituting the first holding mechanism 8a and the main body portion 10 of the first movable member 23 are disengaged from each other, the first movable member 23 and the second movable member 31 are moved in the insertion direction B by the first elastic energy accumulated in the first elastic member 5 to move the needle member 102 of the replacement part 100 to the insertion position where the needle member 102 is insertable into the living body (see FIGS. 5A and 5B). At that time, the first movable member 23 and the second movable member 31 are moved by the equal distance in the insertion direction B to keep the posture of the replacement part 100 in the state illustrated in FIG. 8A. Therefore, a portion of the sensor 101 and the needle portion 111 of the needle member 102 protruding from the lower surface of the sheet member 105 is inserted into the living body.

Then, when the needle member 102 reaches the insertion position, the lock members 36 and the disengagement member 41 are engaged with each other to disengage the second movable member 31 from the lock members 36. Accordingly, the second movable member 31 is moved in the removal direction A with respect to the first movable member 23 by the second elastic energy in the second elastic member 6 (see FIGS. 6A and 6B). Therefore, the needle support portion 113 sandwiched in the second sandwich portion 47 of the second movable member 31 is moved in the removal direction A with respect to the sensor housing 103 sandwiched in the first sandwich portion 46 of the first movable member 23 (see FIG. 8B). Accordingly, the needle member 102 is removed from the living body and moved to the removal position. The needle portion 111 of the needle member 102 moved to the removal position is accommodated in the hollow portion 121 of the hollow member 104. Further, the movement of the needle member 102 in the insertion direction B is restricted by the claw portions 125 provided on the side wall portion 122 of the hollow member 104, and the needle portion 111 remains within the hollow portion 121 (see FIG. 8B).

Next, the sensor insertion device 1 is detached from the replacement part 100. The detached sensor insertion device 1 can be brought into the energy accumulated state again by moving the operation portion 29 positioned outside of the housing 2 in the removal direction A (see FIGS. 7A and 7B) and another replacement part 100 can be attached. That is, according to the sensor insertion device 1, the energy accumulated state can be achieved by a simple operation, and the sensor insertion device 1 can be reused only by attaching another replacement part 100.

Meanwhile, in the replacement part 100 from which the sensor insertion device 1 is detached, the needle member 102 and the hollow member 104 are detached from the sensor housing 103. Accordingly, the replacement part 100 is separated into the members that are formed from the sensor 101, the sensor housing 103, and the sheet member 105 and left in the living body and the members that are formed from the needle member 102 and the hollow member 104 and discarded (see FIG. 8C). According to the replacement part 100, it is possible to leave the members for use in the measurement of biological information in the living body by a simple operation, and separate the waste members including the needle portion 111 not to be directly touched by the medical personnel in an easy and safe manner.

The sensor insertion device and the replacement part according to the present invention are not limited to the configurations of the embodiment described above but can be implemented in various configurations without deviating from the contents of the claims. For example, the elastic energy variable mechanism 7 in the foregoing embodiment has the movement restriction portion 9 oriented in the removal direction A and the main body portion 10 oriented in the insertion direction B with respect to the first elastic member 5 and the second elastic member 6. However, the elastic energy variable mechanism 7 is not limited to this configuration but may be configured to have the main body portion oriented in the removal direction A and the movement restriction portion oriented in the insertion direction B. In addition, the elastic energy variable mechanism 7 of the embodiment achieves the energy accumulated state by moving the operation portion 29 in the removal direction A but the elastic energy variable mechanism 7 is not limited to the configuration in which the operation portion is moved in the removal direction. The elastic energy variable mechanism may be configured to achieve the energy accumulated state by moving the operation portion in a predetermined direction different from the removal direction.

A sensor insertion device 401 and a sensor insertion device 501 as modification examples of the sensor insertion device 1 of the foregoing embodiment will be described below with reference to FIGS. 10 to 23. The same components of the sensor insertion device 401 and the sensor insertion device 501 as those of the sensor insertion device 1 are given the same reference signs as those of the sensor insertion device 1.

<Sensor Insertion Device 401>

First, the sensor insertion device 401 will be described with reference to FIGS. 10 to 18. The sensor insertion device 401 includes: a housing 402; the first elastic member 5 that can accumulate the first elastic energy to move the sensor 101 and the needle member 102 to the insertion position where the sensor 101 and the needle member 102 are insertable into a living body; the second elastic member 6 that can accumulate the second elastic energy to move the needle member 102 from the insertion position to the removal position where the needle member 102 is removable from the living body; an elastic energy variable mechanism 407 that elastically deforms the first elastic member 5 and the second elastic member 6 to achieve the energy accumulated state in which the first elastic energy is accumulated in the first elastic member 5 and the second elastic energy is accumulated in the second elastic member 6; a first holding mechanism 408a that holds the posture of the first elastic member 5 in the energy accumulated state; and a second holding mechanism 408b that holds the posture of the second elastic member 6 in the energy accumulated state and for a period of time during which, after the release of the first elastic member 5 from the hold by the first holding mechanism 408a in the energy accumulated state, the needle member 102 is moved to the insertion position by the first elastic energy.

Figure 10:
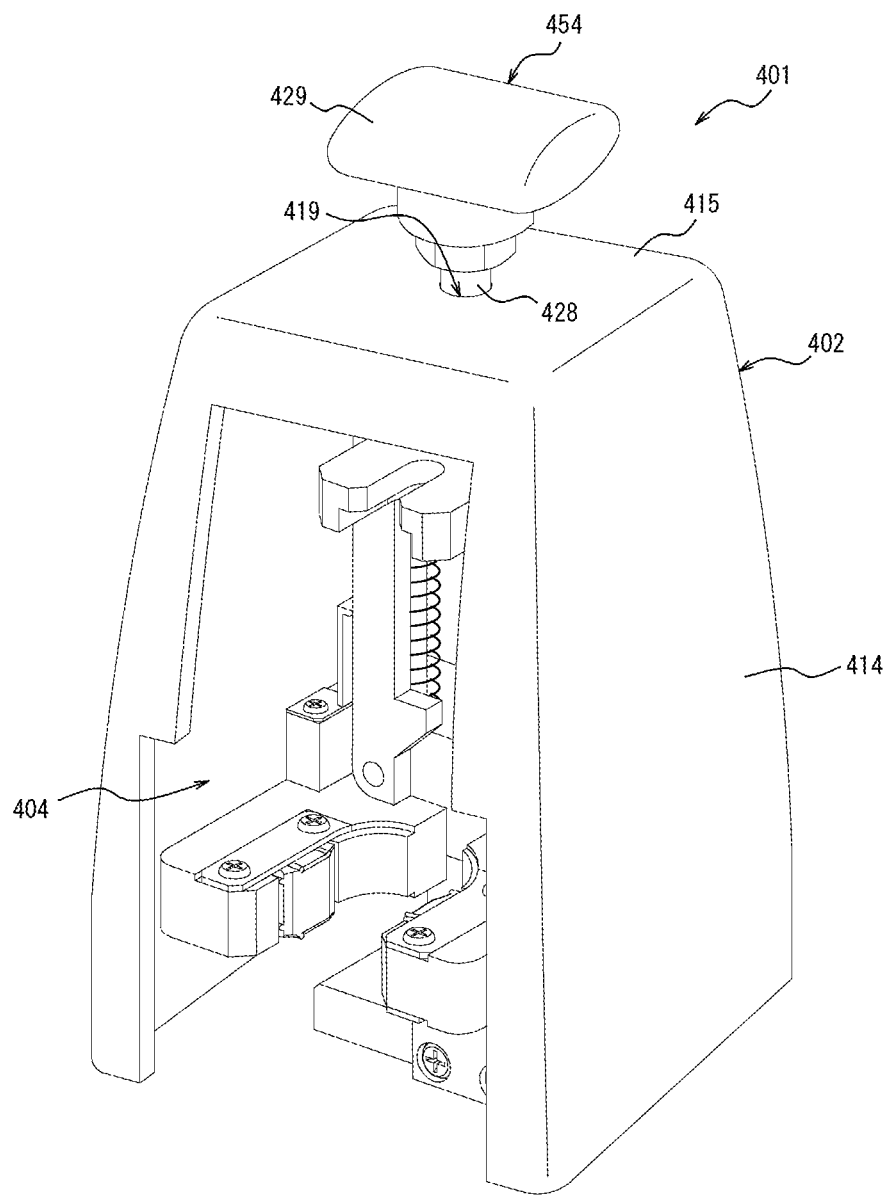
FIG. 10 is a perspective view of a sensor insertion device as a modification example of the sensor insertion device illustrated in FIG. 1.
Figure 11:
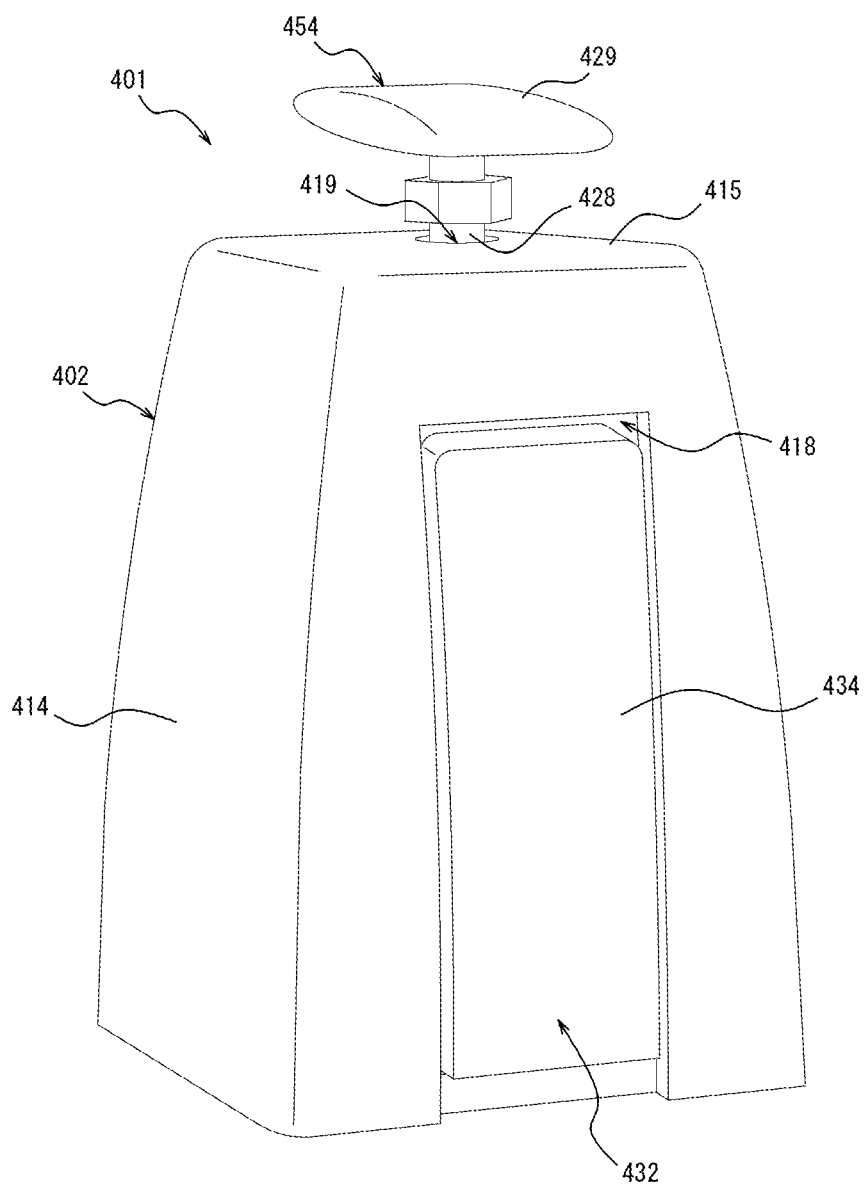
FIG. 11 is a perspective view of the sensor insertion device illustrated in FIG. 10 seen from another direction.
Figure 12:
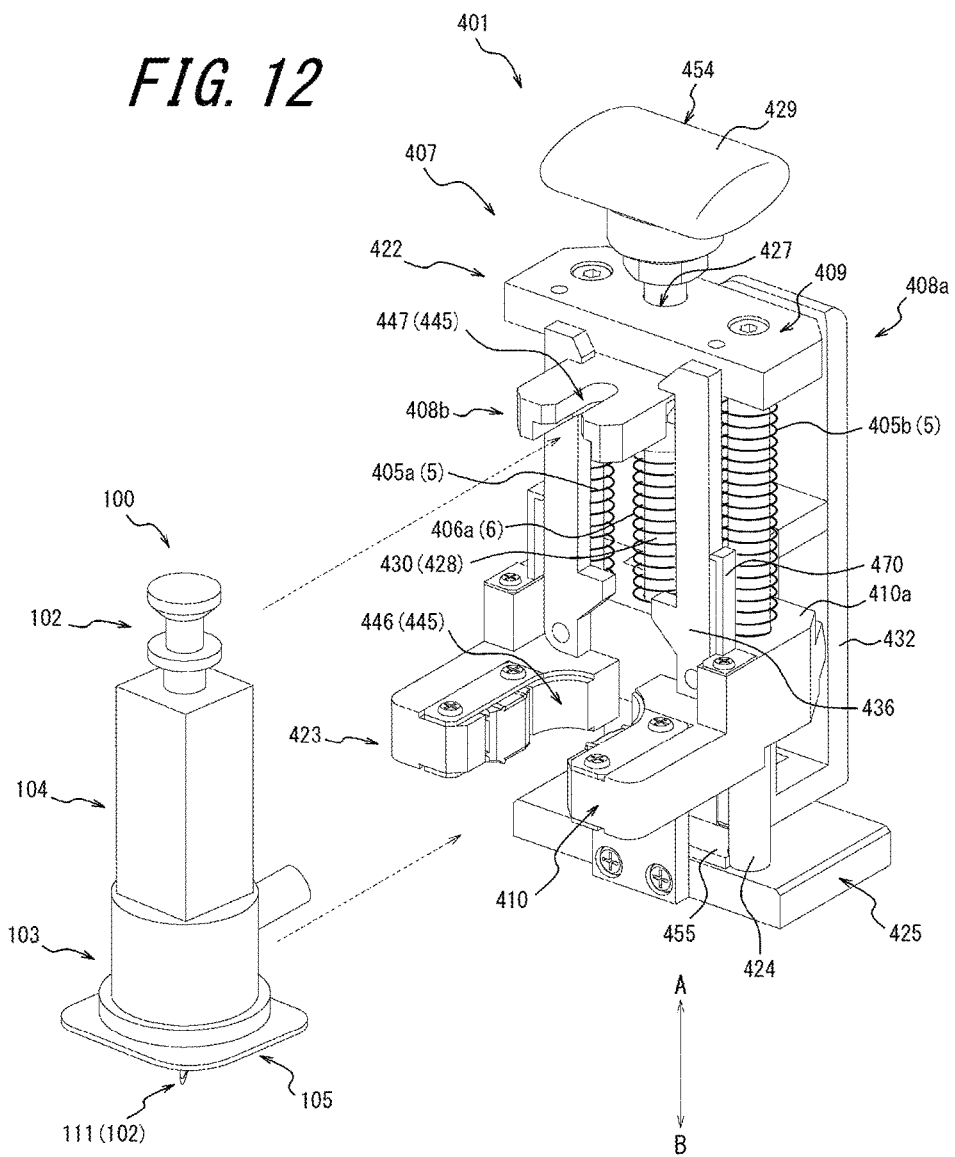
FIG. 12 is a perspective view of the sensor insertion device illustrated in FIGS. 10 and 11 and a replacement part attachable to the sensor insertion device, which are separately illustrated.
Figure 13:
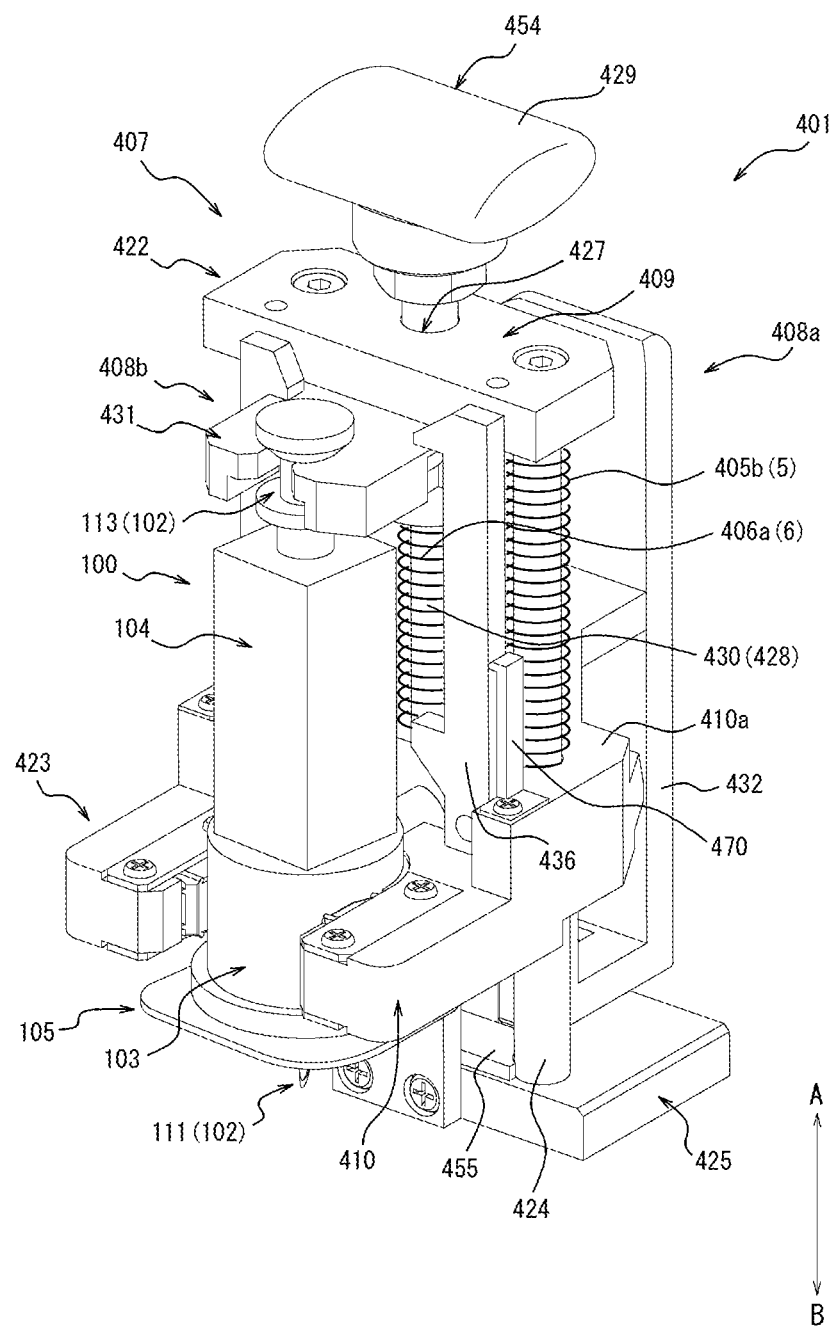
FIG. 13 is a perspective view of a sensor insertion device assembly in which the replacement part illustrated in FIG. 12 is attached to the sensor insertion device illustrated in FIG. 12.

FIGS. 10 and 11 are perspective views of the sensor insertion device 401. FIG. 12 is a perspective view of the sensor insertion device 401 illustrated in FIGS. 10 and 11 and the replacement part 100 attachable to the sensor insertion device 401, which are separately illustrated. FIG. 13 is a perspective view of a sensor insertion device assembly in which the replacement part 100 illustrated in FIG. 12 is moved (see the dash arrow in FIG. 12) and attached to the sensor insertion device 401.

Figure 17A:
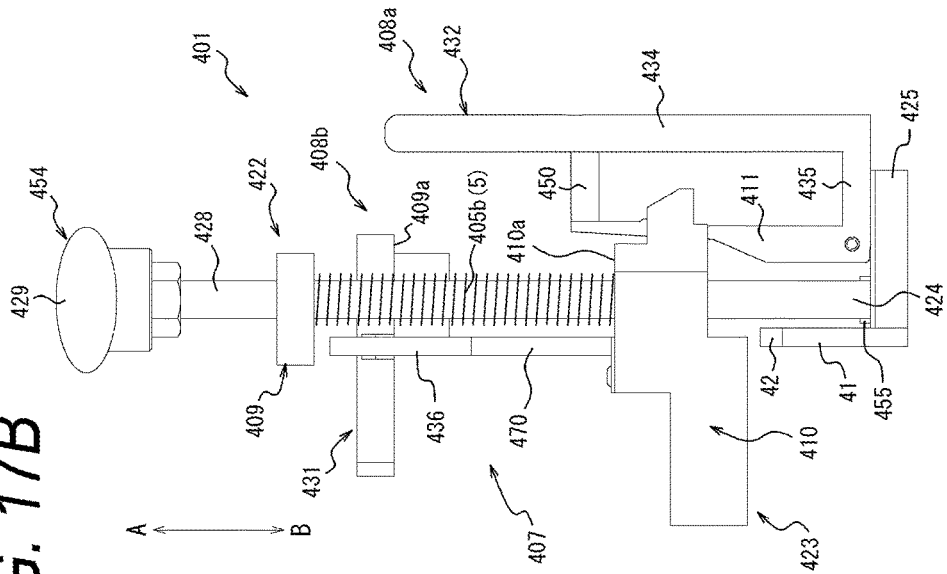
FIGS. 17A and 17B are front and side views illustrating the sensor insertion device illustrated in FIGS. 14A and 14B removed from the replacement part illustrated in FIGS. 14A and 14B and brought into the energy accumulated state in which another replacement part is attachable.
Figure 17B:
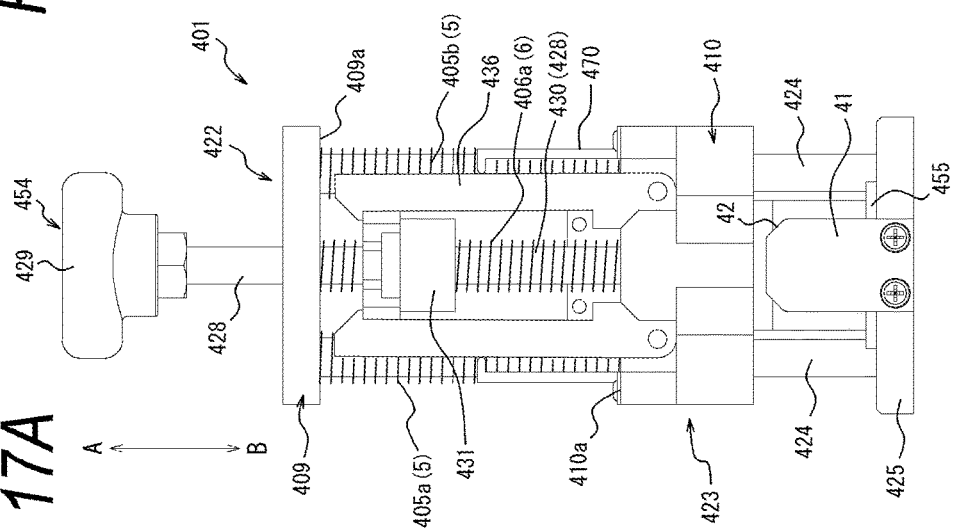

FIGS. 14 to 17 are diagrams respectively illustrating the state in which the replacement part 100 is attached to the sensor insertion device 401 in the energy accumulated state (see FIGS. 14A and 14B), the state in which the first elastic energy accumulated in the first elastic member 5 is used while the second elastic energy is accumulated in the second elastic member 6 so that the needle member 102 reaches the insertion position (see FIGS. 15A and 15B), the state in which the second elastic energy accumulated in the second elastic member 6 is used so that the needle member 102 reaches the removal position (see FIGS. 16A and 16B), and the state in which the sensor insertion device 401 detached from the replacement part 100 is brought into the energy accumulated state again to enable attachment of another replacement part 100 (see FIGS. 17A and 17B). FIGS. 14A, 15A, 16A, and 17A are respective front views of the states, and FIGS. 14B, 15B, 16B, and 17B are respective side views of the states.

FIGS. 12 to 17 do not illustrate the housing 402 illustrated in FIGS. 10 and 11 for the convenience of illustration. The "front view" of the sensor insertion device 401 here means the view of the side on which a side wall opening 404 of the housing 402 is formed, of the sensor insertion device 401, and the "side view" of the sensor insertion device 401 here means the view of the right or left side of the sensor insertion device 401.

In the sensor insertion device 401, the positional relationship between guide portions 424 as shafts of insertion springs 405a and 405b as the first elastic member 5 and a guide portion 430 as a shaft of a return spring 406a as the second elastic member 6 is different from that in the sensor insertion device 1. Specifically, in the sensor insertion device 1, the return spring 6a and the guide portion 30 of the return spring 6a are disposed at positions separated by a predetermined distance or more from the insertion springs 5a and 5b and the guide portion 24 of the insertion springs 5a and 5b (positions separated by a predetermined distance or more so as not to overlap) in a side view (see FIG. 4B and others). Meanwhile, in the sensor insertion device 401, the return spring 406a and the guide portion 430 of the return spring 406a are arranged at positions overlapping the insertion springs 405a and 405b and the guide portion 424 of the insertion springs 405a and 405b in a side view (see FIG. 14B and others) (the guide portions 430 are unseen behind the guide portions 424 in FIG. 14B).

In other words, the separation distance between the guide portion 430 as a shaft that guides the return spring 406a of the sensor insertion device 401 in the deformation direction and the guide portions 424 as shafts that guide the insertion springs 405a and 405b in the deformation direction in a plane oriented perpendicular to the removal direction A and the insertion direction B is shorter than the separation distance between the same portions in the sensor insertion device 1. Bringing the guide portion 430 and the guide portions 424 in the perpendicular plane closer to each other reduces influence on the parallel state of the guide portion 430 and the guide portions 424 by the deformation or tolerance of the portions coupling the guide portion 430 and the guide portions 424 and makes it easy to keep the parallel state of the guide portion 430 and the guide portions 424. As a result, the path of insertion of the needle member 102 and the path of removal of the needle member 102 are likely to coincide with each other to stable the paths of insertion and removal of the needle member 102.

In the sensor insertion device 401 illustrated in FIGS. 10 to 18, the guide portion 430 of the return spring 406*a* is disposed at a position overlapping the guide portions 424 of the insertion springs 405*a* and 405*b* in a side view (see FIG. 14B and others) but the present invention is not limited to this configuration. These guide portions may be disposed in proximity to each other. Therefore, the guide portions may not overlap but be separated from each other by less than a predetermined distance in the same side view as that in FIG. 14B. However, the guide portions are to be close to each other as much as possible. Accordingly, as described above, the guide portions 424 of the insertion springs 405*a* and 405*b* and the guide portion 430 of the return spring 406*a* preferably overlap in the side view (see FIG. 14B and others) as illustrated in FIG. 14B and others. More specifically, in the configuration with the plurality of (two in the sensor insertion device 401) insertion springs 405*a* and 405*b* as in the sensor insertion device 401 illustrated in FIGS. 10 to 18, the return spring 406*a* is preferably interposed between the plurality of insertion springs 405*a* and 405*b*.

Further, as illustrated in FIG. 12 and others, in the sensor insertion device 401, a bar-like portion 428 of a bar-like member 454 used to charge the first elastic member 5 and the second elastic member 6 also acts as the guide portion 430. More specifically, the bar-like member 454 is positioned outside of the housing 402 (see FIGS. 10 and 11) and includes an operation portion 429 capable of being operated from the outside of the housing 402 and the bar-like portion 428 connected to the operation portion 429, and the bar-like portion 428 of the bar-like member 454 extends in the hollow portion of the coil spring as the return spring 406*a*. Accordingly, the center axis line of the return spring 406*a* almost coincides with the center axis line of the bar-like portion 428 also acting as the guide portion 430.

In the sensor insertion device 401, the coil spring as the second elastic member 6 defining the hollow portion is used. However, the second elastic member 6 is not limited to the coil spring as far as it defines the hollow portion.

Configuring the bar-like portion 428 connected to the operation portion 429 to act also as the guide portion 430 of the second elastic member 6 makes it possible to decrease the number of members and makes it easy to achieve the compact sensor insertion device 401. The operation portion 429 may be simply connected to the bar-like portion 428 or may be integrated with the bar-like portion 428.

The components of the sensor insertion device 401 will be described below mainly with regard to the differences from the sensor insertion device 1 except for the foregoing guide portion 430.

[Housing 402]

As illustrated in FIGS. 10 and 11, the housing 402 of the sensor insertion device 401 includes a side wall portion 414 that defines the side wall opening 404 and a top wall portion 415 that is integrated with one end of the side wall portion 414 oriented in the removal direction A and defines a top wall opening 419 as in the housing 2 of the sensor insertion device 1. The housing 402 of the sensor insertion device 401 is mainly different from the housing 2 of the sensor insertion device 1 in that the side wall portion 414 is square cylindrical in shape. However, the side wall portion 414 may have another outer shape such as a circular cylindrical shape. As illustrated in FIGS. 10 and 11, the housing 402 has some portions different in shape from those of the housing 2 of the sensor insertion device 1 in addition to the outer shape of the side wall portion 414. Alternatively, the housing 402 may have these portions identical in shape to those of the housing 2 of the sensor insertion device 1. The housing 402 can be designed as appropriate according to the internal structure of the housing 402.

For example, referring to FIG. 11, the side wall portion 414 has an opening 418 defined at a portion opposed to the side wall opening 404 (see FIG. 10) with the hollow portion of the housing 402 sandwiched therebetween, and an engagement plate portion 434 of a retaining member 432 in the first holding mechanism 408*a* is exposed to the outside of the housing 402 through the opening 418. However, the sensor insertion device 401 is not limited to this configuration. The sensor insertion device 401 may further include an operation member such as the operation member 3 in the sensor insertion device 1.

[Elastic Energy Variable Mechanism 407]

As illustrated in FIGS. 10 to 17, the elastic energy variable mechanism 407 includes a fixed member 422 fixed in position with respect to the housing 402 and a first movable member 423 that is movable with respect to the fixed member 422.

The fixed member 422 includes a bar-like guide portion 424 that extends in the removal direction A (or the insertion direction B), a support base portion 425 that is provided at one end of the guide portion 424 oriented in the insertion direction B, and a movement restriction portion 409 that is provided at one end of the guide portion 424 oriented in the removal direction A. As described above, the sensor insertion device 401 is configured such that the one member acts as both the bar-like protrusion portion 28 and the guide portion 30 in the sensor insertion device 1. Accordingly, the movement restriction portion 409 is smaller in size than the movement restriction portion 9 in the sensor insertion device 1.

The first movable member 423 includes a main body member that constitutes a main body portion 410 to change the opposing distance to the movement restriction portion 409 of the fixed member 422 and the bar-like member 454 that is movable with respect to the main body portion 410 and the movement restriction portion 409 in the removal direction A and the insertion direction B while the main body portion 410 is inserted through a insertion hole penetrating in the removal direction A (and the insertion direction B) and a guide hole 427 in the movement restriction portion 409.

In the sensor insertion device 1, the bar-like protrusion portion 28 connected to the operation portion 29 is fixed to and integrated with the main body portion 10. Meanwhile, in the sensor insertion device 401, the bar-like portion 428 connected to the operation portion 429 is provided on the bar-like member 454 that is movable with respect to the main body portion 410 in the removal direction A and the insertion direction B. That is, the first movable member 423 of the sensor insertion device 401 is formed from the mutually independent and relatively movable main body member and bar-like member 454, in which the first movable member 423 is different in the first movable member 23 of the sensor insertion device 1.

However, besides the operation portion 429 and the bar-like portion 428, the bar-like member 454 includes a flange portion 455 (see FIG. 12 and others) that is provided at one end of the bar-like portion 428 oriented in the insertion direction B and protrudes radially beyond the bar-like portion 428. Accordingly, moving the bar-like member 454 in the removal direction A allows the flange portion 455 to engage with the main body member constituting the main body portion 410 and move the main body member in the removal direction A. Specifically, operating the bar-like member 454 makes it possible to move the main body member constituting the main body portion 410 in the removal direction A, subject the first elastic member 5 and the second elastic member 6 to compressive deformation between the movement restriction portion 409 and the main body portion 410 of the fixed member 422, thereby achieving the energy accumulated state.

As described above, the first movable member 423 is different in configuration from the first movable member 23 of the sensor insertion device 1 but is identical to the first movable member 23 in being movable with respect to the fixed member 422 to change the positional relationship with the fixed member 422 and achieve the energy accumulated state of the first elastic member 5 and the second elastic member 6. The first movable member 423 may be configured in an integrated manner as the first movable member 23 of the sensor insertion device 1.

In the sensor insertion device 401, the bar-like portion 428 of the bar-like member 454 also acts as the bar-like guide portion 430 of the return spring 406a. Accordingly, the main body portion 410 is made smaller in size than the main body portion 10 of the sensor insertion device 1. Further, as illustrated in FIGS. 10 and 11, the operation portion 429 held by the person to be measured or the like to achieve the energy accumulated state (to charge the first elastic member 5 and the second elastic member 6) is plate-like in shape but is no limited to this shape. For example, the operation portion 429 may have another shape such as an annular shape as the operation portion 29 of the sensor insertion device 1.

As described above, the elastic energy variable mechanism 407 of the sensor insertion device 401 is formed from the fixed member 422 and the first movable member 423, and the elastic energy variable mechanism 407 can change the sensor insertion device 401 from the state in which the first elastic energy is not accumulated in the first elastic member 5 and the second elastic energy is not accumulated in the second elastic member 6 (see FIGS. 16A and 16B) to the energy accumulated state (see FIGS. 14 and 17).

[First Holding Mechanism 408a]

The first holding mechanism 408a includes the retaining member 432 that constitutes the retaining portion to retain the main body portion 410 of the first movable member 423 in the energy accumulated state as illustrated in FIGS. 12 to 17. Specifically, the first holding mechanism 408a is formed from the fixed member 422, the first movable member 423, and the retaining member 432. More specifically, the first holding mechanism 408a is formed from the support base portion 425 of the fixed member 422, the main body portion 410 of the first movable member 423, and the retaining member 432 that is changeable in position between the state in abutment with the main body portion 410 and the state not in abutment with the main body portion 410 according to the movement of the main body portion 410 with respect to the support base portion 425.

Figure 15A:
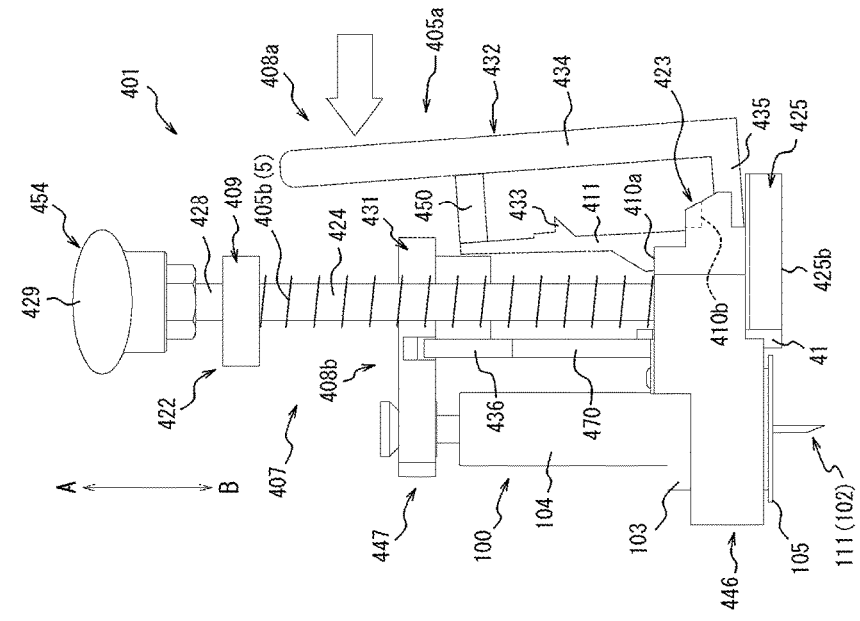
FIGS. 15A and 15B are front and side views illustrating the state in which a needle member in the replacement part illustrated in FIGS. 14A and 14B reaches an insertion position by the action of the sensor insertion device illustrated in FIGS. 14A and 14B.
Figure 15B:
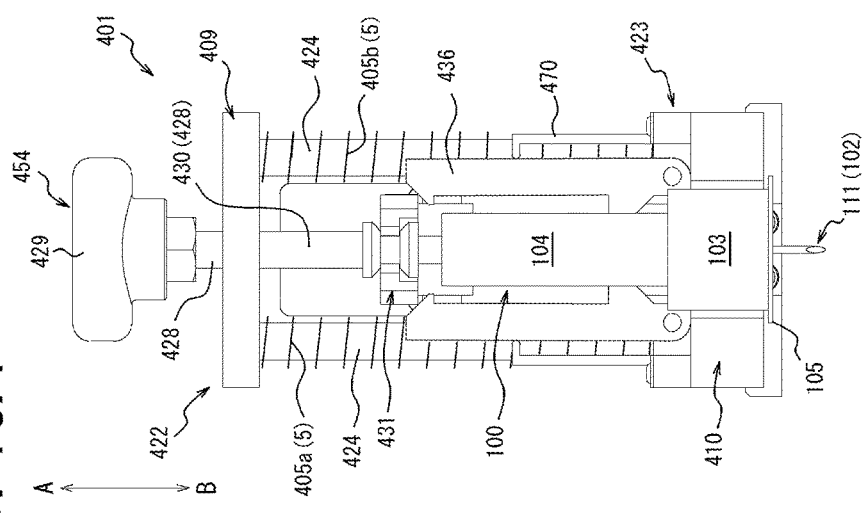
Figure 16A:
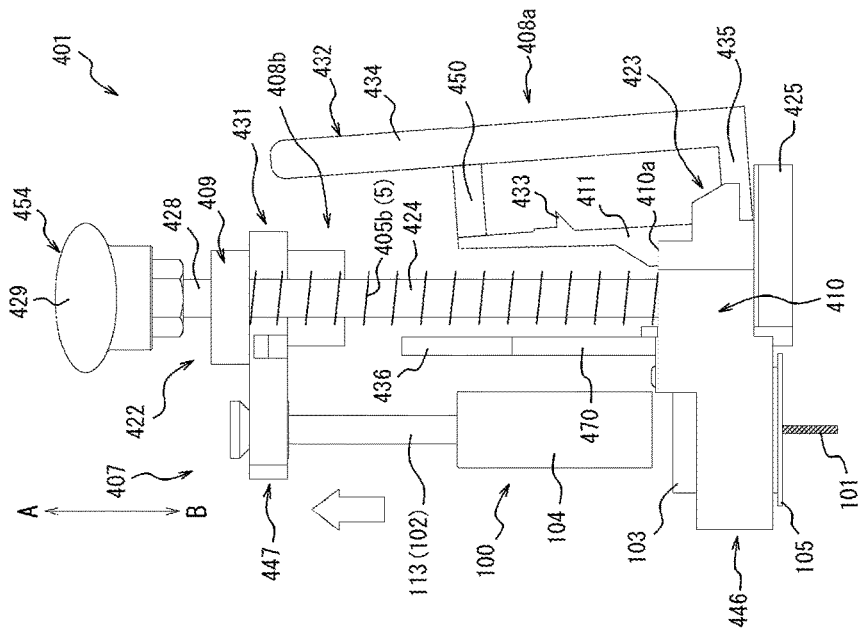
FIGS. 16A and 16B are front and side views illustrating the state in which the needle member in the replacement part illustrated in FIGS. 14A and 14B reaches a removal position by the action of the sensor insertion device illustrated in FIGS. 14A and 14B.
Figure 16B:
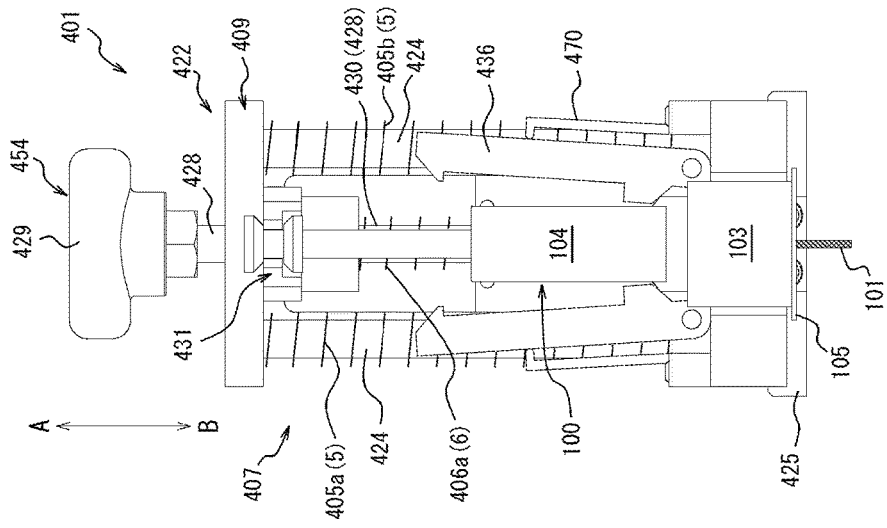

The retaining member 432 is rotatable with respect to the support base portion 425 and includes a claw portion 433 that is changeable in position between the state in abutment with a bottom surface 410b of the main body portion 410 and the state in not abutment with the bottom surface 410b of the main body portion 410 by rotating with respect to the support base portion 425 as illustrated in FIGS. 14B and 15B. In the energy accumulated state, as illustrated in FIGS. 14A and 14B, the claw portion 433 abuts with the bottom surface 410b of the main body portion 410 to restrict the movement of the main body portion 410 in the insertion direction B. When the retaining member 432 in the state illustrated in FIGS. 14A and 14B rotates, the claw portion 433 is disengaged from the bottom surface 410b of the main body portion 410 and the main body portion 410 moves in the insertion direction B by the resilience of the first elastic member 5 (see FIGS. 15A and 15B).

More specifically, the retaining member 432 includes a retaining plate portion 411 having the claw portion 433, the engagement plate portion 434 to be operated from the outside of the housing 402, a coupling plate portion 435 that transfers the force acting on the engagement plate portion 434 to the retaining plate portion 411, and a reinforcement plate portion 450 that couples the retaining plate portion 411 and the engagement plate portion 434 at a different position from the position of the coupling plate portion 435. In other words, the retaining member 432 of the sensor insertion device 401 is configured such that the reinforcement plate portion 450 is added to the retaining member 32 of the sensor insertion device 1. The provision of the reinforcement plate portion 450 makes it possible to suppress the independent elastic deformation of the engagement plate portion 434 and facilitate the transfer of the force acting on the engagement plate portion 434 to the retaining plate portion 411.

The other components of the retaining member 432 are the same as those of the retaining member 32 of the sensor insertion device 1.

[Second Holding Mechanism 408b]

The second holding mechanism 408b includes the first movable member 423, a second movable member 431, and a lock member 436 that constitutes the lock portion. More specifically, the second holding mechanism 408b includes the main body portion 410 of the first movable member 423, the bar-like portion 428 that also acts as the guide portion 430 of the first movable member 423, the second movable member 431 that is sandwiched between the movement restriction portion 409 and the second elastic member 6 and is movable with respect to the movement restriction portion 409 and the main body portion 410 along the guide portion 430, and the lock member 436 that engages with the second movable member 431 biased by the second elastic member 6 in the removal direction A in the energy accumulated state to fix the position of the second movable member 431 with respect to the main body portion 410. The second holding mechanism 408b is different from the second holding mechanism 8b of the sensor insertion device 1 in that the bar-like portion 428 also acts as the guide portion 430 and the movement restriction portion 409 and the second movable member 431 are modified in shape according to this.

Further, in the second holding mechanism 408b, a top surface 410a of the main body portion 410 of the first movable member 423 has a spring member 470 protruding in the removal direction A to provide the resilience to the rotating lock member 436. When the lock member 436 rotates around the rotation shaft, the lock member 436 elastically deforms the spring member 470. When the needle member 102 moves to the removal position by the second elastic energy in the second elastic member 6, the lock member 436 is pushed and returned to the initial position by the resilience of the spring member 470.

The second holding mechanism 408b of the sensor insertion device 401 is configured in the same manner as the second holding mechanism 8b except for the foregoing points. In addition, as illustrated in FIGS. 14 to 17, the operations of the second holding mechanism 408b are the same as those of the second holding mechanism 8b of the sensor insertion device 1 and thus descriptions thereof are omitted here.

[Attachment Portion 445]

The sensor insertion device 401 includes an attachment portion 445 to which the replacement part 100 is detachably attached. Specifically, the attachment portion 445 includes a first sandwich portion 446 that is formed from the first movable member 423 to sandwich the sensor housing 103 of the replacement part 100 and a second sandwich portion 447 that is formed from the second movable member 431 to sandwich the needle member 102 of the replacement part 100.

Figure 18:
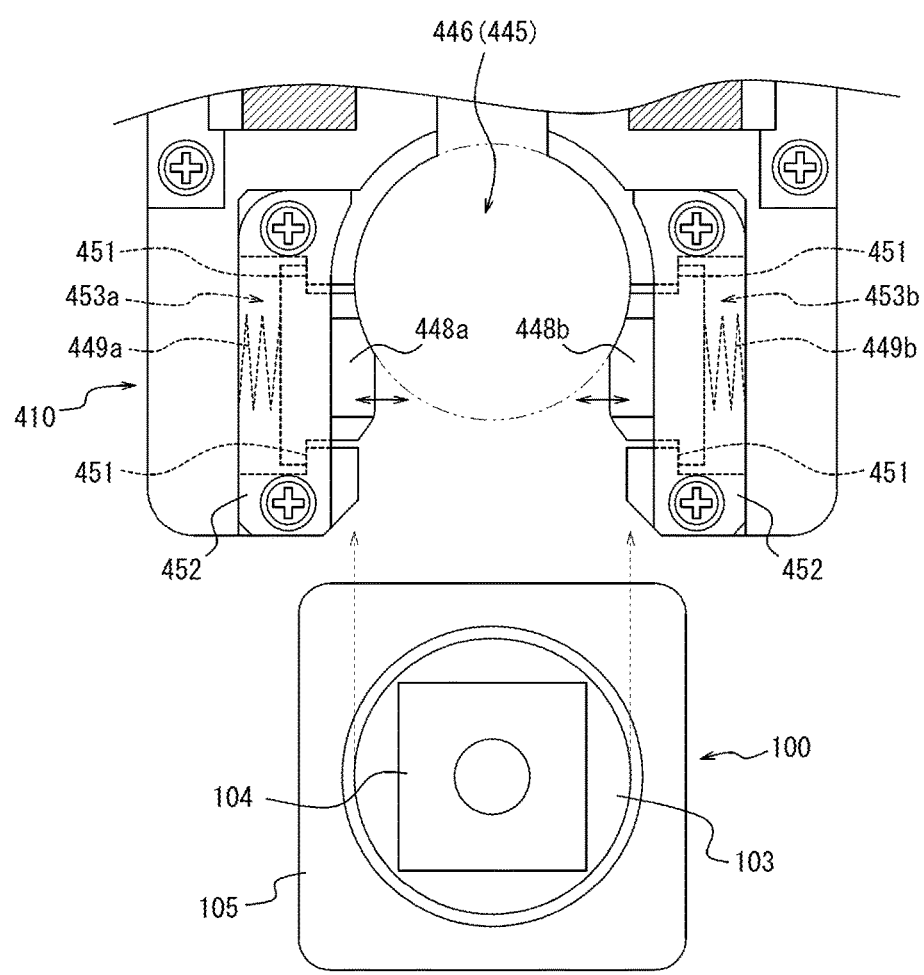
FIG. 18 is a diagram of an upper surface of a first holding portion and its neighborhood.

The first sandwich portion 446 is formed from an inner wall defining a cutout in the outer edge of the main body portion 410 as in the first sandwich portion 46 of the sensor insertion device 1. However, portions of the inner wall defining the cutout adjacent to the first sandwich portion 446 are different in configuration from that of the sensor insertion device 1. FIG. 18 is a top view of the first sandwich portion 446 and its neighborhood of the main body portion 410. As illustrated in FIG. 18, the portions adjacent to the both sides of the first sandwich portion 446 have movement pieces 448a and 448b that change the opposing distance to cause variations in the amount of constriction. The movement pieces 448a and 448b are biased by biasing members 449a and 449b in opposite directions.

The biasing members 449a and 449b are accommodated in recess portions 453a and 453b (see the dashed lines in FIG. 18) formed in the inner wall defining the cutout in the main body portion 410 to bias the movement pieces 448a and 448b in opposite directions. In addition, the recess portions 453a and 453b have abutment portions 451 to abut partially with the movement pieces 448a and 448b to prevent the movement pieces 448a and 448b from coming off the recess portions 453a and 453b. Further, the recess portions 453a and 453b are closed by plate pieces 452 joined to the main body portion 410 on the removal direction A side and the insertion direction B side. Accordingly, the biasing members 449a and 449b accommodated in the recess portions 453a and 453b are configured not to come off the recess portions 453a and 453b by the inner wall of the cutout defining the recess portions 453a and 453b, the plate pieces 452, and the movement pieces 448a and 448b.

When the movement pieces 448a and 448b are provided in the adjacent portions of the first sandwich portion 446, the movement pieces 448a and 448b move toward the inside of the recess portions 453a and 453b at the time of attachment of the sensor housing 103 of the replacement part 100. Accordingly, the sensor housing 103 can be easily moved to the first sandwich portion 446. In addition, when the sensor housing 103 is sandwiched in the first sandwich portion 446, the movement pieces 448a and 448b move and protrude from the recess portions 453a and 453b. This forms a constricted portion in the inner wall of the cutout to suppress return of the sensor housing 103 fitted in the first sandwich portion 446 to the edge side of the cutout.

The second sandwich portion 447 is the same as the second sandwich portion 47 of the sensor insertion device 1 and thus descriptions thereof are omitted here.

<Sensor Insertion Device 501>

Next, a sensor insertion device 501 as another modification example of the sensor insertion device 1 will be described with reference to FIGS. 19 to 23. The sensor insertion device 501 includes: the first elastic member 5 that can accumulate the first elastic energy to move the sensor 101 and the needle member 102 to the insertion position where the sensor 101 and the needle member 102 are insertable into a living body; the second elastic member 6 that can accumulate the second elastic energy to move the needle member 102 from the insertion position to the removal position where the needle member 102 is removable from the living body; an elastic energy variable mechanism 507 that can elastically deform the first elastic member 5 and the second elastic member 6 to achieve the energy accumulated state in which the first elastic energy is accumulated in the first elastic member 5 and the second elastic energy is accumulated in the second elastic member 6; a first holding mechanism 508a that holds the posture of the first elastic member 5 in the energy accumulated state; and a second holding mechanism 508b that holds the posture of the second elastic member 6 in the energy accumulated state and for the period of time between the release of the first elastic member 5 from the first holding mechanism 508a in the energy accumulated state and the movement of the needle member 102 to the insertion position by the first elastic energy.

Figure 19:
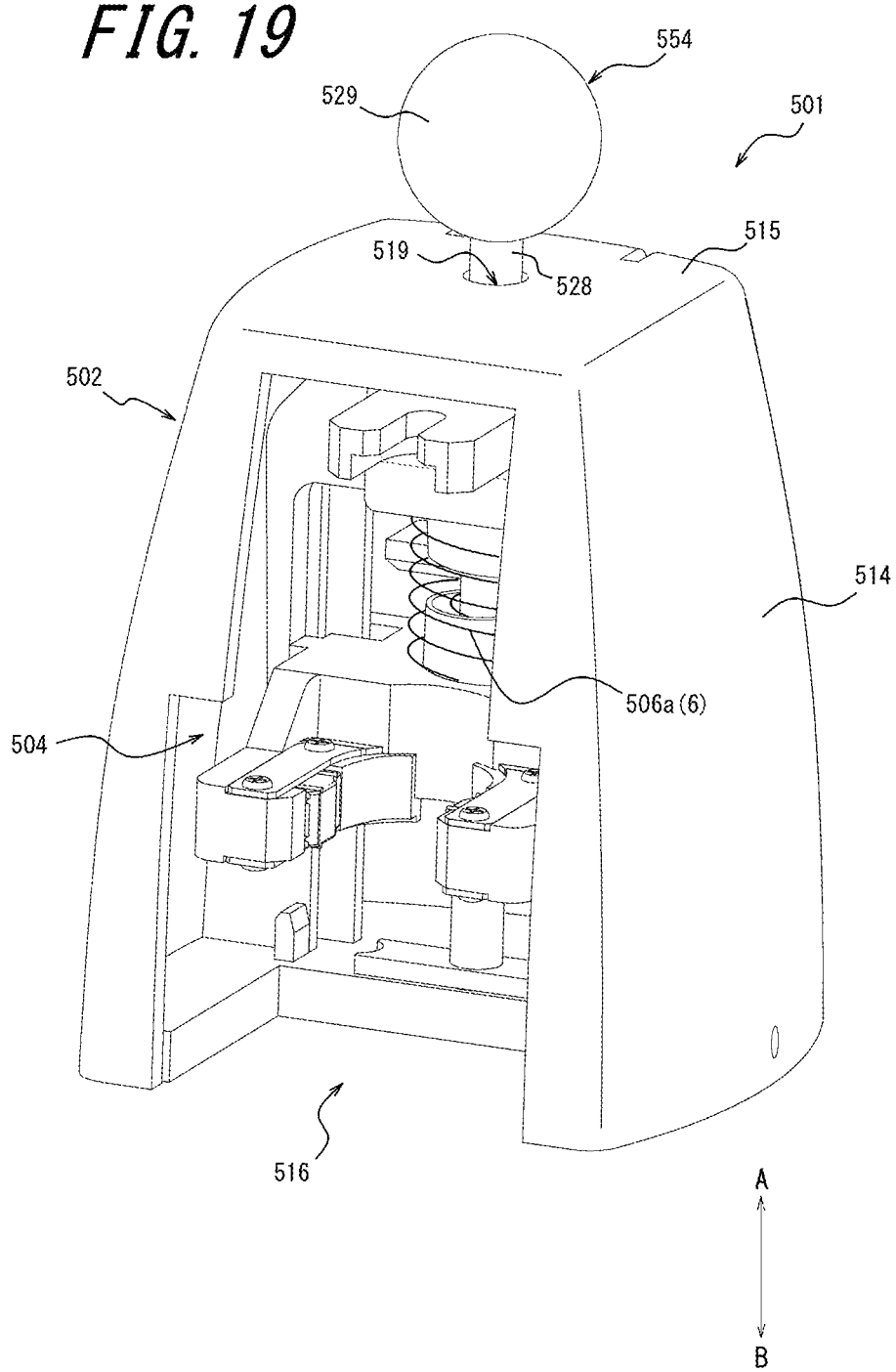
FIG. 19 is a perspective view of a sensor insertion device as another modification example of the sensor insertion device illustrated in FIG. 1.
Figure 22A:
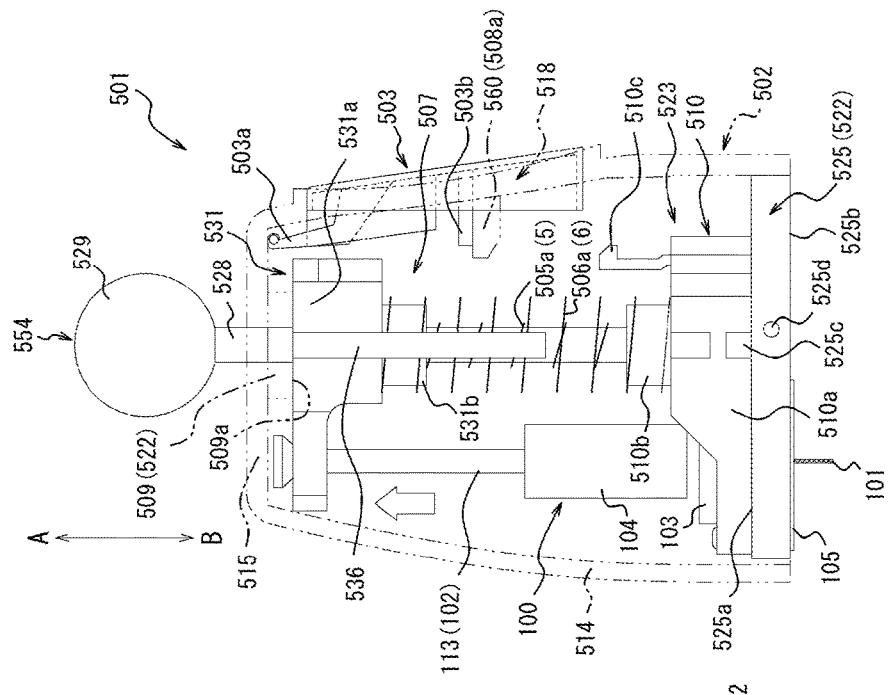
FIGS. 22A and 22B are front and side views illustrating the state in which the needle member in the replacement part illustrated in FIGS. 20A and 20B reaches a removal position by the action of the sensor insertion device illustrated in FIGS. 20A and 20B.
Figure 22B:
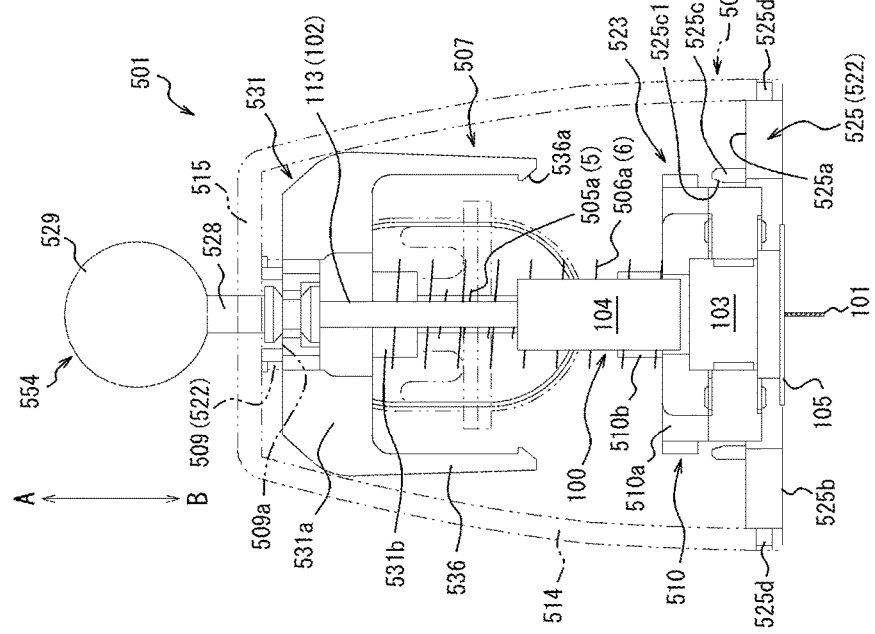

FIG. 19 is a perspective view of the sensor insertion device 501. FIGS. 20 to 23 are diagrams respectively illustrating the state in which the replacement part 100 is attached to the sensor insertion device 501 in the energy accumulated state (see FIGS. 20A and 20B), the state in which the first elastic energy accumulated in the first elastic member 5 is used with the second elastic energy accumulated in the second elastic member 6 so that the needle member 102 reaches the insertion position (see FIGS. 21A and 21B), the state in which the second elastic energy accumulated in the second elastic member 6 is used so that the needle member 102 reaches the removal position (see FIGS. 22A and 22B), and the state in which the sensor insertion device 501 detached from the replacement part 100 is brought into the energy accumulated state again to enable attachment of another replacement part 100 (see FIGS. 23A and 23B). FIGS. 20A, 21A, 22A, and 23A are respective front views of the states, and FIGS. 20B, 21B, 22B, and 23B are respective side views of the states.

FIGS. 20 to 23 illustrate the inner surface and the outer surface of a housing 502 illustrated in FIG. 19 by two-dot chain lines for the convenience of description. The "front surface" of the sensor insertion device 501 here means the surface on which a side wall opening 504 of the housing 502 is formed, of the sensor insertion device 501, and the "side surface" of the sensor insertion device 501 here means the right or left surface of the sensor insertion device 501.

The sensor insertion device 501 is different from the sensor insertion device 1 and the sensor insertion device 401 in the positional relationship between the center axis line of the first elastic member 5 and the center axis line of the second elastic member 6. Specifically, in the sensor insertion device 501, an insertion spring 505a as the first elastic member 5 and a return spring 506a as the second elastic member 6 are coil springs that define the hollow portions extending in the removal direction A and the insertion direction B, and an insertion spring 505a extends in the hollow portion of the return spring 506a. According to this configuration, as compared to the sensor insertion device 1 and the sensor insertion device 401 in which the center axis line of the first elastic member 5 and the center axis line of the second elastic member 6 do not coincide with each other, the center axis line of the insertion spring 505a as the first elastic member 5 and the center axis line of the return spring 506a as the second elastic member 6 can almost coincide with each other in the sensor insertion device 501.

In the sensor insertion device 501, the coil springs as the first elastic member 5 and the second elastic member 6 defining the hollow portions are used. However, the first elastic member 5 and the second elastic member 6 are not limited to the coil springs as far as they define the hollow portions.

In addition, the sensor insertion device 501 is configured such that the first elastic member 5 extends in the hollow portion of the second elastic member 6. Alternatively, either one of the first elastic member 5 and the second elastic member 6 may extend in the hollow portion of the other, and the second elastic member 6 may extend in the hollow portion of the first elastic member 5.

According to the configuration in which either one of the first elastic member 5 and the second elastic member 6 extends in the hollow portion of the other, it is possible to allow the center axis line of the first elastic member 5 and the center axis line of the second elastic member 6 to almost coincide with each other. Accordingly, the insertion path of the needle member 102 and the removal path of the needle member 102 can almost coincide with each other, thereby further stabilizing the insertion and removal paths of the needle member 102 as compared to the sensor insertion device 1 and the sensor insertion device 401.

Further, the sensor insertion device 501 includes a bar-like member 554 having a bar-like portion 528 connected to an operation portion 529 operable from the outside, and the bar-like portion 528 of the bar-like member 554 extends in the hollow portion of the coil spring as the insertion spring 505a and the hollow portion of the coil spring as the return spring 506a. According to the configuration in which the first elastic member 5 and the second elastic member 6 define the hollow portions as coil springs, for example, either one of the elastic members extends in the hollow portion of the other elastic member and the bar-like member 554 extends in the hollow portion of the one elastic member, the center axis line of the first elastic member 5 and the center axis line of the second elastic member 6 can also almost coincide with the center axis line of the bar-like portion 528 that is connected to the operation portion 529 to be held to charge the first elastic member 5 and the second elastic member 6.

In addition, according to the configuration in which the center axis lines of the bar-like member 554, the first elastic member 5, and the second elastic member 6 almost coincide with one another, it is possible to stabilize the paths of the needle member 102 and make the sensor insertion device 501 easy to miniaturize as compared to the sensor insertion device 1 and the sensor insertion device 401.

The components of the sensor insertion device 501 will be described below.

[Housing 502]

The housing 502 includes a side wall portion 514 that defines the side wall opening 504 and a top wall portion 515 that is integrated with one end of the side wall portion 514 oriented in the removal direction A as in the housing 2 of the sensor insertion device 1. The housing 502 has no bottom wall at a position opposed to the top wall portion 515 but defines an open portion 516 that communicates with the hollow portion of the housing 502.

In addition, as illustrated in FIG. 19, the top wall portion 515 defines a top wall opening 519. The ball-like operation portion 529 to be gripped by the person to be measured and the like to achieve the energy accumulated state (to charge the first elastic member 5 and the second elastic member 6) protrudes to the outside of the housing 2 through the top wall opening 519.

The internal structure of the sensor insertion device 501 is put into the housing 502 from the open portion 516 defined by one end of the side wall portion 514 of the housing 502 oriented in the insertion direction B. Fitting holes into which fitting projections 525d of a support base portion 525 described later is formed in the side wall portion 514 in the vicinity of the open portion 516.

As illustrated in FIG. 19, the side wall portion 514 is rectangular cylindrical in outer shape in the housing 502 of the sensor insertion device 501. Alternatively, the side wall portion 514 may have another outer shape such as a circular cylindrical shape as the housing 2 of the sensor insertion device 1.

In addition, as illustrated in FIGS. 20 to 23, an opening 518 is defined in the portions of the side wall portion 514 opposed to each other with the side wall opening 504 and the hollow portion of the housing 502 sandwiched therebetween, and an operation member 503 capable of releasing a main body portion 510 from the first holding mechanism 508a as described later is exposed from the opening 518 to the outside of the housing 502. The operation member 503 includes an arm portion 503a that extends toward the inside of the housing 502, and the distal end portion of the arm portion 503a is rotatably attached to the inner wall of the housing 502. In addition, the operation member 503 includes an engagement projection 503b protruding toward the inside of the housing 502. When the operation member 503 rotates around the distal end portion of the arm portion 503a, the engagement projection 503b engages with a claw portion 510c of the main body portion 510 to release the claw portion 510c from a retaining portion 560 of the first holding mechanism 508a.

The housing 502 of the sensor insertion device 501 constitutes part of a fixed member 522 described later. The details will be provided later.

[Elastic Energy Variable Mechanism 507]

The elastic energy variable mechanism 507 includes the fixed member 522 and a first movable member 523 that is movable with respect to the fixed member 522.

The fixed member 522 includes a movement restriction portion 509 and the support base portion 525. Specifically, the movement restriction portion 509 of the sensor insertion device 501 is formed from the inner surface of the top wall portion 515 of the housing 502. The support base portion 525 of the sensor insertion device 501 is formed from a plate member that is fixed to the housing 502 by fitting the fitting projections 525d to the fitting holes formed in the vicinity of the open portion 516 of the side wall portion 514 of the housing 502 (see FIG. 19). Therefore, the fixed member 522 of the sensor insertion device 501 is formed from the housing 502 with the movement restriction portion 509 and the plate member fixed in position with respect to the housing 502.

The support base portion 525 is plate-like in shape with the thickness direction oriented in the removal direction A and the insertion direction B. When the needle member 102 is inserted, a bottom surface 525b positioned in the insertion direction B abuts with the surface of the living body.

The movement restriction portion 509 is positioned in the removal direction A with respect to the first elastic member 5 and the second elastic member 6 to suppress directly or indirectly the movement in the removal direction A. of the ends of the first elastic member 5 and the second elastic member 6 oriented in the removal direction A.

More specifically, a bottom surface 509a of the movement restriction portion 509 positioned in the insertion direction B constitutes the surface of receiving the insertion spring 505a as the first elastic member 5. That is, one end of the insertion spring 505a as the first elastic member 5 oriented in the removal direction A is in abutment with the bottom surface 509a of the movement restriction portion 509. A second movable member 531 is interposed between the bottom surface 509a of the movement restriction portion 509 positioned in the insertion direction B and one end of the return spring 506a as the second elastic member 6 oriented in the removal direction A. The second movable member 531 constitutes the portion for receiving the one end of the return spring 506a as the second elastic member 6 oriented in the removal direction A and can abut with the second elastic member 6. That is, the one end of the return spring 506a as the second elastic member 6 oriented in the removal direction A does not abut with the bottom surface 509a of the movement restriction portion 509. Accordingly, the movement restriction portion 509 restricts directly the movement in the removal direction A of the end of the first elastic member 5 oriented in the removal direction A and restricts indirectly the movement in the removal direction A of the end of the second elastic member 6 oriented in the removal direction A via the second movable member 531.

The top wall opening 519 (see FIG. 19) is formed in the top wall portion 515 at the position corresponding to the movement restriction portion 509. The top wall opening 519 acts as a guide hole that guides the movement of the bar-like member 554 described later in the removal direction A and the insertion direction B.

The first movable member 523 includes a main body member constituting the main body portion 510 that changes the opposing distance to the movement restriction portion 509, a insertion hole that penetrates through the main body portion 510 in the removal direction A (and the insertion direction B), and the bar-like member 554 that is movable in the removal direction A and the insertion direction B with respect to the main body portion 510 and the movement restriction portion 509 while being inserted through the top wall opening 519 as the guide hole (see FIG. 19).

The main body portion 510 includes a foundation portion 510a and a circular cylindrical receiving portion 510b that protrudes from the foundation portion 510a in the removal direction A.

Figure 23A:
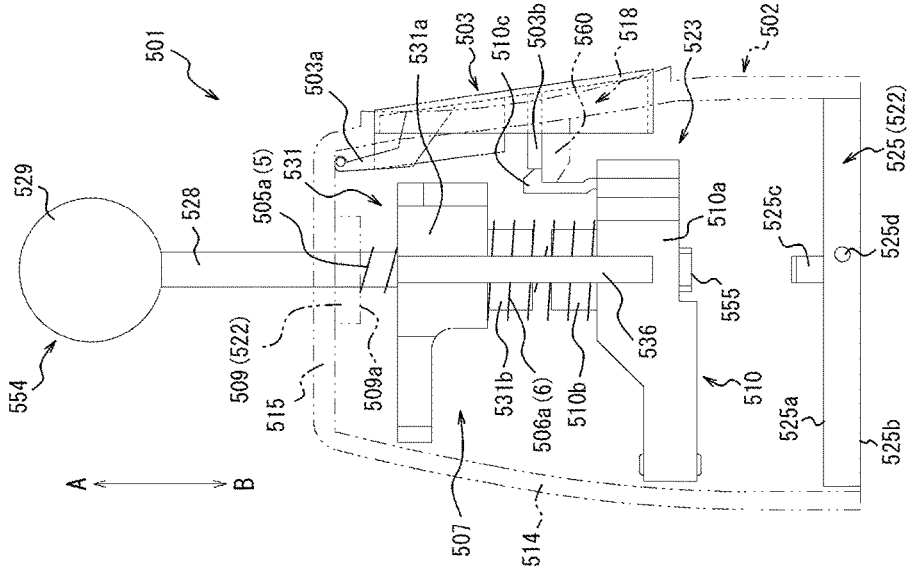
FIGS. 23A and 23B are front and side views illustrating the sensor insertion device illustrated in FIGS. 20A and 20B removed from the replacement part illustrated in FIGS. 20A and 20B and brought into the energy accumulated state in which another replacement part is attachable.
Figure 23B:
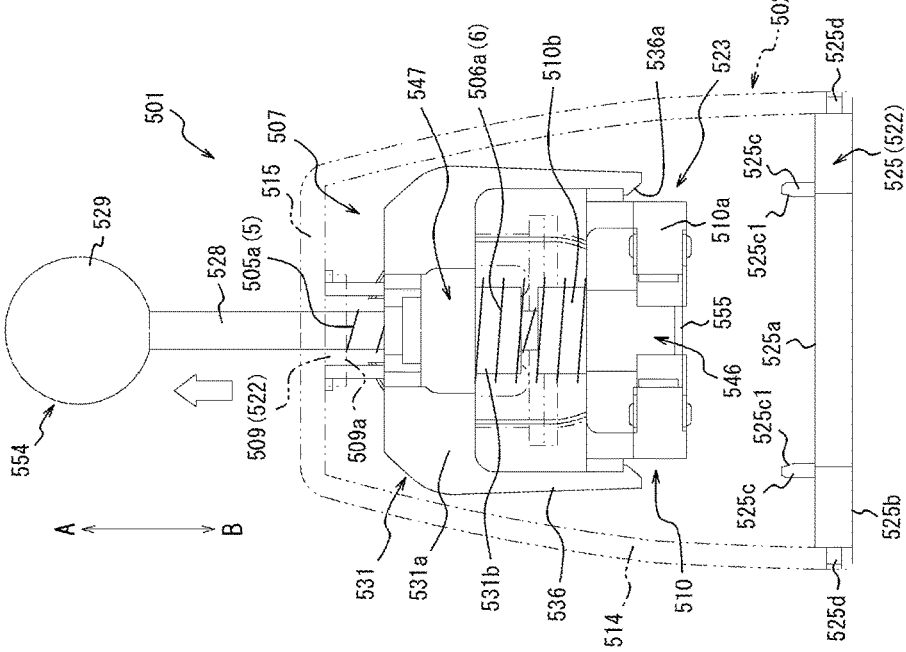

The foundation portion 510a has a first sandwich portion 546 that can sandwich the sensor housing 103 of the replacement part 100 (see FIGS. 23A and 23B).

The receiving portion 510b receives on the top surface one end of the insertion spring 505a as the first elastic member 5 oriented in the insertion direction B. One end portion of the return spring 506a as the second elastic member 6 oriented in the insertion direction B is fitted onto the outer peripheral surface of the receiving portion 510b. The one end of the return spring 506a oriented in the insertion direction B is received by the foundation portion 510a, and a spiral one end portion in the vicinity of the one end of the return spring 506a oriented in the insertion direction B is received by the outer peripheral surface of the receiving portion 510b.

The bar-like member 554 includes the straight bar-like portion 528, the ball-like operation portion 529 that is connected to one end of the bar-like portion 528 oriented in the removal direction A and is positioned outside of the housing 502, and a plate-like flange portion 555 that is connected to one end of the bar-like portion 528 oriented in the insertion direction B and protrudes radially beyond the bar-like portion 528.

The bar-like portion 528 is inserted through all the top wall opening 519 in the housing 502, the insertion hole penetrating through the main body portion 510, and the insertion hole penetrating the second movable member 531 described later.

The bar-like member 554 is not fixed to the housing 502, the main body portion 510, and the second movable member 531. With no application of external force to the bar-like member 554, the flange portion 555 is in abutment with a top surface 525a of the support base portion 525 (see FIGS. 20A and 20B). Moving the operation portion 529 in the removal direction A makes it possible to move the bar-like portion 528 and the flange portion 555 in the removal direction A (see FIGS. 23A and 23B). During the movement, the flange portion 555 and the main body portion 510 engage with each other to move the main body portion 510 together with the bar-like member 554 in the removal direction A. Accordingly, the main body portion 510 is movable to change the opposing distance between the fixed member 522 and the movement restriction portion 509. Moving the main body portion 510 in the removal direction A and the insertion direction B makes it possible to elastically deform the first elastic member 5 and the second elastic member 6 at the same time between the main body portion 510 and the movement restriction portion 509.

In the sensor insertion device 501, as described above, the elastic energy variable mechanism 507 is formed from the fixed member 522 and the first movable member 523. The elastic energy variable mechanism 507 allows the sensor insertion device 501 to change from the state in which the first elastic energy is not accumulated in the first elastic member 5 and the second elastic energy is not accumulated in the second elastic member 6 (see FIGS. 22A and 22B) to the energy accumulated state (see FIGS. 20 and 23). The operation of charging the first elastic member 5 and the second elastic member 6 to achieve the energy accumulated state will be described below.

The elastic energy variable mechanism 507 of the sensor insertion device 501 moves the main body portion 510 in the removal direction A such that the opposing distance to the movement restriction portion 509 becomes shorter, subjects the first elastic member 5and the second elastic member 6 to compressive deformation at the same time between the main body portion 510 and the movement restriction portion 509 to achieve the energy accumulated state in which the first elastic energy is accumulated in the first elastic member 5 and the second elastic energy is accumulated in the second elastic member 6. FIGS. 19, 20, and 23 illustrate the sensor insertion device 501 in the energy accumulated state.

More specifically, first, the operation portion 529 positioned outside of the housing 502 (see FIG. 19 and others) is gripped to move the bar-like member 554 in the removal direction A. When the bar-like member 554 is moved in the removal direction A, the flange portion 555 engages with the main body portion 510 and the main body portion 510 moves in the removal direction A as well. At that time, the main body portion 510 moves in the removal direction A against the resilience of the first elastic member 5 and the second elastic member 6. Accordingly, the opposing distance between the main body portion 510 and the movement restriction portion 509 becomes shorter, and the insertion spring 505a as the first elastic member 5 undergoes compressive deformation between the top surface of the receiving portion 510b of the main body portion 510 and the bottom surface 509a of the movement restriction portion 509. In addition, the return spring 506a as the second elastic member 6 undergoes compressive deformation between the top surface of the foundation portion 510a of the main body portion 510 and the bottom surface 509a of the movement restriction portion 509, more specifically, between the top surface of the foundation portion 510a of the main body portion 510 and the second movable member 531.

Then, when the opposing distance between the main body portion 510 and the movement restriction portion 509 reaches a predetermined distance or less, the energy accumulated state is achieved (see FIGS. 20 and 23).

When the bar-like member 554 is moved in the removal direction A, the main body portion 510 can be moved in the removal direction A but the second movable member 531 abuts with the bottom surface 509a of the movement restriction portion 509 and does not move in the removal direction A from the position of the bottom surface 509a of the movement restriction portion 509. That is, the bottom surface 509a of the movement restriction portion 509 does not abut directly with the second elastic member 6 but applies reaction force to the second elastic member 6 via the second movable member 531 when the main body portion 510 is moved in the removal direction A. Therefore, when the main body portion 510 is moved in the removal direction A, the bottom surface 509a of the movement restriction portion 509 constitutes a reaction force wall to apply reaction force to the first elastic member 5 and the second elastic member 6. This makes it possible to subject the first elastic member 5 and the second elastic member 6 to compressive deformation between the main body portion 510 and the movement restriction portion 509.

When the main body portion 510 of the first movable member 523 moves in the removal direction A, the insertion spring 505a as the first elastic member 5 undergoes compressive deformation while sliding on the outer wall of the bar-like portion 528 of the bar-like member 554. That is, the deforming directions of the first elastic member 5 are limited by the bar-like portion 528 to the removal direction A and the insertion direction B. In addition, the return spring 506a as the second elastic member 6 has the end portion oriented in the removal direction A and fitted onto the circular cylindrical receiving portion 531b of the second movable member 531 and has the end portion oriented in the insertion direction B and fitted onto the receiving portion 510b of the main body portion 510. Accordingly, the deforming directions of the return spring 506a are limited to the removal direction A and the insertion direction B. Further, the main body portion 510 of the first movable member 523 and the second movable member 531 move while sliding on the inner wall of the housing 502 and are guided by the inner wall of the housing 502 such that the moving directions are the removal direction A and the insertion direction B. That is, in the sensor insertion device 501, the deforming directions of the first elastic member 5 and the second elastic member 6 and the moving directions of the first movable member 523 and the second movable member 531 are limited to the removal direction A and the insertion direction B.

According to the elastic energy variable mechanism 507 of the sensor insertion device 501 as described above, moving the operation portion 529 in the removal direction A makes it possible to subject the first elastic member 5 and the second elastic member 6 to compressive deformation to charge the first elastic member 5 and the second elastic member 6. That is, moving the operation portion 529 in the removal direction A makes it possible to bring the sensor insertion device 501 into the energy accumulated state.

Further, as in the elastic energy variable mechanism 507 of the sensor insertion device 501, it is preferable that the first elastic member 5 and the second elastic member 6 can be subjected to compressive deformation and can be charged at the same time by moving the operation portion 529 in the removal direction A. According to this configuration, the energy accumulated state can be achieved by a smaller number of operations.

[First Holding Mechanism 508a]

The first holding mechanism 508a includes the retaining portion 560 that retains the main body portion 510 of the first movable member 523 in the energy accumulated state as illustrated in FIGS. 20 to 23. Specifically, the retaining portion 560 of the first holding mechanism 508a is formed from a projection that protrudes from the inner wall of the housing 502 and engages with the claw portion 510c of the main body portion 510. As described above, the retaining portion 560 of the first holding mechanism 508a and the claw portion 510c of the main body portion 510 can be disengaged from each other by rotating the operation member 503 around the distal end portion of the arm portion 503a, engaging the engagement projection 503b with the claw portion 510c, and elastically deforming the claw portion 510c as described above.

[Second Holding Mechanism 508b]

The second holding mechanism 508b is formed from the first movable member 523 and the second movable member 531. More specifically, the second holding mechanism 508b of the sensor insertion device 501 is formed from the main body member and the bar-like member 554 constituting the main body portion 510 of the first movable member 523 and the second movable member 531 that is sandwiched between the movement restriction portion 509 and the second elastic member 6 and is movable along the bar-like member 554 with respect to the movement restriction portion 509, the main body member, and the bar-like member 554.

The second movable member 531 includes a foundation portion 531a, a circular cylindrical receiving portion 531b that protrudes from the foundation portion 531a in the insertion direction B, and a lock portion 536 that protrudes from the outer edge portion of the foundation portion 531a in the insertion direction B. The foundation portion 531a has a second sandwich portion 547 (see FIG. 23A) that sandwiches the needle member 102 of the replacement part 100.

The second holding mechanism 508b of the sensor insertion device 501 is different in configuration from the sensor insertion device 1 and the sensor insertion device 401 mainly in that the second movable member 531 itself has the lock portion 536 to fix the position of the second movable member 531 with respect to the main body portion 510 while the second movable member 531 is biased by the second elastic member 6 in the removal direction A.

More specifically, the lock portion 536 is a claw portion that protrudes from the foundation portion 531a of the second movable member 531. The claw portion as the lock portion 536 gets caught on the outer edge of the foundation portion 510a of the main body portion 510 while predetermined elastic energy is accumulated in the second elastic member 6 having undergone compressive deformation between the main body portion 510 of the first movable member 523 and the second movable member 531. Accordingly, the second movable member 531 can get caught on the main body member constituting the main body portion 510.

In the sensor insertion device 501, the top surface 525a of the support base portion 525 has a projection portion 525c protruding in the removal direction A. The projection portion 525c can engage with the lock portion 536 to disengage the lock portion 536 and the main body portion 510 from each other. Specifically, the distal end surface of the projection portion 525c has a tapered portion 525c1, and the distal end surface of the lock portion 536 has a tapered portion 536a corresponding to the tapered portion 525c1 of the projection portion 525c. These tapered portions 525c1 and 536a slide on each other when the needle member 102 reaches the insertion position (see FIGS. 21A and 21B), and the tapered portion 525c1 exerts force on the lock portion 536 in the direction perpendicular to the removal direction A to elastically deform the lock portion 536 in that direction. Accordingly, the lock portion 536 and the main body portion 510 can be disengaged from each other, and the needle member 102 can be moved to the removal position by the elastic energy accumulated in the second elastic member 6 (see FIGS. 22A and 22B).

As described above, the sensor insertion device 501 includes a switch mechanism that, when the needle member 102 reaches the insertion position (see FIGS. 21A and 21B), can switch alternatively from the movement of the needle member 102 in the insertion direction B by the biasing force of the first elastic member 5 (the resilience of the insertion springs 505a having undergone compressive deformation in the sensor insertion device 501) to the movement of the needle member 102 in the removal direction A by the biasing force of the second elastic member 6 (the resilience of the return spring 506a having undergone compressive deformation in the sensor insertion device 501). The alternative switching means the same thing as described above in relation to the sensor insertion device 1.

According to the sensor insertion devices 401 and 501 as modification examples of the sensor insertion device 1, it is possible to realize the more stable insertion and removal of the needle member 102 and achieve the smaller-sized devices as compared to the sensor insertion device 1.

The insertion of the sensor 101 and the needle member 102 by the sensor insertion device assembly in which the replacement part 100 is attached to the sensor insertion device 401 and the sensor insertion device 501 and the removal of the needle member 102 by the sensor insertion device assembly are the same as those by the sensor insertion device assembly 300 in which the replacement part 100 is attached to the sensor insertion device 1 as illustrated in FIGS. 14 to 17 and 20 to 23, and descriptions thereof are omitted here.

The embodiments described herein relate to a sensor insertion device for inserting a sensor capable of detecting biological information on a living body of a patient or the like, and a replacement part attachable to the sensor insertion device.

REFERENCE NUMERAL LIST

1 Sensor insertion device
2 Housing
3 Operation member
4 Side wall opening
5 First elastic member
5a, 5b Insertion spring
6 Second elastic member
6a Return spring
7 Elastic energy variable mechanism
8a First holding mechanism
8b Second holding mechanism
9 Movement restriction portion
9a Bottom surface
10 Main body portion
10a Top surface
10b Bottom surface
11 Retaining plate portion
14 Side wall portion
15 Top wall portion
16 Open portion
17 Shaft support portion
18 Opening
19 Top wall opening
20 Main body portion
21 Rotation shaft portion
22 Fixed member
23 Movable member (first movable member)
24 Guide portion
25 Support base portion
25a Top surface
25b Bottom surface
27a First guide hole
27b Second guide hole
28 Bar-like protrusion portion
29 Operation portion
30 Guide portion
31 Movable member (second movable member)
31a Top surface
32 Retaining member (retaining portion)
33 Claw portion of retaining member
34 Engagement plate portion
35 Coupling plate portion
36 Lock member (lock portion)
37 Main body portion
38 Protrusion portion
39 Claw portion of lock member
40 Claw portion of lock member
41 Disengagement member (disengagement portion)
42 Tapered portion of disengagement member
43 Tapered portion of claw portion of lock member
44 Tapered portion of claw portion of lock member
45 Attachment portion
46 First sandwich portion
47 Second sandwich portion
100 Replacement part
101 Sensor
102 Needle member
103 Sensor housing
104 Hollow member
105 Sheet member
106 Insertion hole in sensor housing
107 Straight portion of optical fiber
108 Distal end portion of optical fiber
109 Curve portion of optical fiber
110 Proximal end portion of optical fiber
111 Needle portion
112 Connection portion
113 Needle support portion
113a Flange portion
114 Annular groove portion
115 Trunk portion
116 Base portion
117 Fitting groove
118 Guide path
121 Hollow portion
122 Side wall portion
123 Bottom wall portion
124 Top wall portion
125 Claw portion (one-way lock portion)
125a Retaining surface
126 Insertion hole in top wall portion
127 Insertion hole in bottom wall portion
150 Optical fiber (light guiding member)
151 Detection portion
200 Processing device 201 Light emission portion
202 Light receiving portion
203 Optical detection portion
204 Processing portion
205 Connection opening
300 Sensor insertion device assembly
401, 501 Sensor insertion device
402, 502 Housing
404, 504 Side wall opening
405a, 405b, 505a Insertion spring
406a, 506a Return spring
407, 507 Elastic energy variable mechanism
408a, 508a First holding mechanism
408b, 508b Second holding mechanism
409, 509 Movement restriction portion
410, 510 Main body portion
410a Top surface of main body portion
410b Bottom surface of main body portion
411 Retaining plate portion
414, 514 Side wall portion
415, 515 Top wall portion
418, 518 Opening
419, 519 Top wall opening
422, 522 Fixed member
423, 523 First movable member
424 Guide portion
425, 525 Support base portion
427 Guide hole
428, 528 Bar-like portion
429, 529 Operation portion
430 Guide portion
431, 531 Second movable member
432 Retaining member
433 Claw portion
434 Engagement plate portion
435 Coupling plate portion
436 Lock member (lock portion)
445 Attachment portion
446, 546 First sandwich portion
447 Second sandwich portion
448a, 448b Movement piece
449a, 449b Biasing member
450 Reinforcement plate portion
451 Abutting portion
452 Plate piece
453a, 453b Recess portion
454, 554 Bar-like member
455, 555 Flange portion
470 Spring member
503 Operation member
503a Arm portion
503b Engagement projection
509a Bottom surface of movement restriction portion
510a Foundation portion of main body portion
510b Receiving portion of main body portion
531a Foundation portion of second movable member
531b Receiving portion of second movable member
536 Lock portion
536a Tapered portion
516 Open portion
525a Top surface of support base portion
525b Bottom surface of support base portion
525c Projection portion of support base portion
525c1 Tapered portion
525d Fitting projection
560 Retaining portion A Removal direction of needle member
B Insertion direction of needle member

What is claimed is:

1. A sensor insertion device for inserting a needle member, together with a sensor configured to detect biological information, into a living body, and for removing the needle member from the living body after leaving a distal end side of the sensor in the living body, the sensor insertion device comprising:
a first elastic member configured to accumulate first elastic energy to move the sensor and the needle member in an insertion direction to an insertion position where the sensor and the needle member are inserted into the living body;
a second elastic member configured to accumulate second elastic energy to move the needle member in a removal direction from the insertion position to a removal position where the needle member is removed from the living body;
an elastic energy variable mechanism configured to elastically deform the first elastic member and the second elastic member to achieve an energy accumulated state in which the first elastic energy is accumulated in the first elastic member and the second elastic energy is accumulated in the second elastic member, wherein the elastic energy variable mechanism comprises:
a fixed member comprising a movement restriction portion that is positioned on a removal direction side of the needle member with respect to the first elastic member and the second elastic member, and
a movable member that is movable with respect to the fixed member, the movable member comprising a main body portion that is positioned in an insertion direction side of the needle member with respect to the first elastic member and the second elastic member,
wherein the fixed member and the movable member sandwich the first elastic member and the second elastic member therebetween, and
wherein the main body portion is movable in the removal direction to elastically deform the first elastic member and the second elastic member at the same time between the main body portion and the movement restriction portion, to thereby achieve the energy accumulated state;
a first holding mechanism configured to hold a position of the first elastic member in the energy accumulated state; and
a second holding mechanism configured to hold a position of the second elastic member in the energy accumulated state and for a period of time during which, after the release of the first elastic member from the first holding mechanism in the energy accumulated state, the needle member is moved to the insertion position by the first elastic energy.

2. The sensor insertion device according to claim 1, wherein the first holding mechanism comprises a retaining portion configured to retain the movable member in the energy accumulated state.

3. The sensor insertion device according to claim 1, wherein:
the sensor insertion device comprises a plurality of first elastic members, including the first elastic member recited in claim 1, and
the second elastic member is disposed between the plurality of first elastic members.

4. The sensor insertion device according to claim 1, wherein:

the second elastic member defines a hollow portion,
the movable member comprises a bar-like portion that is connected to an operation portion configured to be operated from an outside of the sensor insertion device, and
the bar-like portion extends in the hollow portion of the second elastic member.

5. The sensor insertion device according to claim 1, wherein:
one of the first elastic member and the second elastic member defines a first hollow portion, and
the other of the first elastic member and the second elastic member extends in the first hollow portion of the one elastic member.

6. The sensor insertion device according to claim 5, wherein
the other elastic member defines a second hollow portion,
the movable member comprises a bar-like portion that is connected to an operation portion configured to be operated from an outside of the sensor insertion device, and
the bar-like portion extends in the second hollow portion of the other elastic member.

7. The sensor insertion device according to claim 1, wherein:
the movable member is a first movable member,
the second holding mechanism comprises:
a second movable member that is sandwiched between the fixed member and the second elastic member and is movable with respect to the fixed member and the first movable member, and
a lock portion configured to engage with the second movable member biased by the second elastic member toward the fixed member while the second elastic energy is accumulated in the second elastic member, to fix the position of the second movable member with respect to the first movable member.

8. The sensor insertion device according to claim 7, further comprising a disengagement portion configured to disengage the lock portion from the second movable member when the needle member reaches the insertion position.

9. The sensor insertion device according to claim 1, further comprising an attachment portion to which a replacement part comprising the sensor and the needle member is attachable from an outside of the sensor insertion device while the sensor insertion device is in the energy accumulated state.

10. A replacement part for use with the sensor insertion device recited in claim 9, the replacement part comprising:
the sensor; and
the needle member;
wherein the replacement part is attachable to the sensor insertion device according to claim 9.

11. The replacement part according to claim 10, further comprising:
a sensor housing that defines an insertion hole in which the needle member is movable by the sensor insertion device from the insertion position to the removal position,
wherein the sensor comprises a portion that extends outward from a slit formed in the needle member in the sensor housing.

12. The replacement part according to claim 11, wherein:
the sensor comprises:
a light guiding member that has a distal end configured to be left in a living body and a proximal end configured to extend outside of the living body, and a detection portion that is located at the distal end of the light guiding member and is configured to detect biological information; and
the light guiding member comprises a curve portion that extends outward from the slit in the needle member.

13. The replacement part according to claim 10, further comprising:
a hollow member that accommodates the needle member when the needle member moves to the removal position;
wherein the hollow member includes a one-way lock portion that, after movement of the needle member from the insertion position to the removal position, restricts movement of the needle member back to the insertion position.

14. A sensor insertion device assembly comprising:
a sensor insertion device; and
a replacement part comprising:
a sensor configured to detect biological information, and
a needle member configured to be inserted together with the sensor into a living body, and to be removed from the living body after a distal end side of the sensor is left in the living body,
wherein the sensor insertion device comprises:
a first elastic member configured to accumulate first elastic energy to move the sensor and the needle member in an insertion direction to an insertion position where the sensor and the needle member are inserted into the living body,
a second elastic member configured to accumulate second elastic energy to move the needle member from the insertion position to a removal position where the needle member is removed from the living body,
an elastic energy variable mechanism configured to elastically deform the first elastic member and the second elastic member to achieve an energy accumulated state in which the first elastic energy is accumulated in the first elastic member and the second elastic energy is accumulated in the second elastic member, wherein the elastic energy variable mechanism comprises:
a fixed member comprising a movement restriction portion that is positioned on a removal direction side of the needle member with respect to the first elastic member and the second elastic member, and
a movable member that is movable with respect to the fixed member, the movable member comprising a main body portion that is positioned in an insertion direction side of the needle member with respect to the first elastic member and the second elastic member,
wherein the fixed member and the movable member sandwich the first elastic member and the second elastic member therebetween, and
wherein the main body portion is movable in the removal direction to elastically deform the first elastic member and the second elastic member at the same time between the main body portion and the movement restriction portion, to thereby achieve the energy accumulated state, and
an attachment portion to which the replacement part is detachably attached, and
wherein the sensor and the needle member are separable from each other after insertion of the sensor.

15. A sensor insertion method for inserting a needle member, together with a sensor configured to detect biological information, into a living body, and for removing the needle member from the living body after leaving a distal end side of the sensor in the living body, the method comprising:

providing a sensor insertion device comprising:
- a first elastic member configured to accumulate first elastic energy to move the sensor and the needle member in an insertion direction to an insertion position where the sensor and the needle member are inserted into the living body,
- a second elastic member configured to accumulate second elastic energy to move the needle member in a removal direction from the insertion position to a removal position where the needle member is removed from the living body;
- an elastic energy variable mechanism configured to elastically deform the first elastic member and the second elastic member to achieve an energy accumulated state in which the first elastic energy is accumulated in the first elastic member and the second elastic energy is accumulated in the second elastic member, wherein the elastic energy variable mechanism comprises:
  - a fixed member comprising a movement restriction portion that is positioned on a removal direction side of the needle member with respect to the first elastic member and the second elastic member, and
  - a first movable member that is movable with respect to the fixed member, the first movable member comprising a main body portion that is positioned in an insertion direction side of the needle member with respect to the first elastic member and the second elastic member,
  - wherein the fixed member and the first movable member sandwich the first elastic member and the second elastic member therebetween, and
  - wherein the main body portion is movable in the removal direction to elastically deform the first elastic member and the second elastic member at the same time between the main body portion and the movement restriction portion, to thereby achieve the energy accumulated state,
- a first holding mechanism configured to hold a position of the first elastic member in the energy accumulated state, and
- a second holding mechanism configured to hold a position of the second elastic member in the energy accumulated state and for a period of time during which, after the release of the first elastic member from the first holding mechanism in the energy accumulated state, the needle member is moved to the insertion position by the first elastic energy, wherein the second holding mechanism comprises a second movable member that is sandwiched between the fixed member and the second elastic member and is movable with respect to the fixed member and the first movable member; and a replacement part comprising:
- the sensor configured to detect biological information, and
- the needle member that is insertable together with the sensor into a living body and is removable from the living body after a distal end side of the sensor is left in the living body, accumulating first elastic energy in the first elastic member;

accumulating second elastic energy in the second elastic member;

attaching the replacement part to the sensor insertion device;

pressing one end defining the open portion against a surface of the living body;

moving the first movable member and the second movable member in an insertion direction by releasing the first elastic energy; and moving the second movable member in a removal direction with respect to the first movable member by releasing the second elastic energy.

* * * * *